United States Patent
Brown

(10) Patent No.: US 8,436,162 B2
(45) Date of Patent: May 7, 2013

(54) ARABIDOPSIS DERIVED PROMOTERS FOR REGULATION OF PLANT EXPRESSION

(75) Inventor: Devon L. Brown, Wake Forest, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 13/551,661

(22) Filed: Jul. 18, 2012

(65) Prior Publication Data

US 2012/0284881 A1    Nov. 8, 2012

Related U.S. Application Data

(60) Division of application No. 12/565,807, filed on Sep. 24, 2009, now abandoned, which is a division of application No. 11/334,085, filed on Jan. 18, 2006, now Pat. No. 7,615,624, which is a continuation-in-part of application No. 09/887,567, filed on Jun. 22, 2001, now abandoned.

(60) Provisional application No. 60/214,087, filed on Jun. 23, 2000, provisional application No. 60/213,848, filed on Jun. 23, 2000, provisional application No. 60/258,692, filed on Dec. 29, 2000.

(51) Int. Cl.
  *C07H 21/04* (2006.01)
  *C12N 15/82* (2006.01)
  *A01H 5/00* (2006.01)

(52) U.S. Cl.
  USPC .......... 536/24.1; 800/278; 800/279; 800/281; 800/295; 800/298; 435/419

(58) Field of Classification Search .................. None
See application file for complete search history.

(56) References Cited

U.S. PATENT DOCUMENTS

| 6,705,817 B2 | 3/2004 | Wittenstein et al. |
| 7,109,033 B2 | 9/2006 | Harper et al. |
| 2008/0113342 A1 | 5/2008 | Cao et al. |

FOREIGN PATENT DOCUMENTS

| WO | 0198480 | 12/2001 |
| WO | WO 01/98480 | * 12/2001 |

OTHER PUBLICATIONS

EU *Arabidopsis* sequencing project. *Arabidopsis thaliana* DNA chromosome 4, contig fragment No. 43. (2000) GenBank Accession AL161543; pp. 1-71.*
Donald et al., The EMBO Journal, 1990, 9 pp. 1717-1726 Kim et al. PMB. 1994, 24. pp. 105-117.
Budworth et al., File History for U.S. Appl. No. 7,615,624 issued Nov. 10, 2009.

* cited by examiner

*Primary Examiner* — Cathy Kingdon Worley
(74) *Attorney, Agent, or Firm* — S. Matthew Edwards

(57) ABSTRACT

The instant invention is directed to a constitutive promoter for use in plants. The plant genus from which the promoter is derived is *Arabidopsis*. The invention encompasses the isolated promoter, expression cassettes comprising said promoter and a heterologous nucleic acid segment, and monocot and dicot plants and plant cells transformed with said expression cassettes.

10 Claims, No Drawings

ARABIDOPSIS DERIVED PROMOTERS FOR REGULATION OF PLANT EXPRESSION

CROSS REFERENCE TO RELATED APPLICATIONS

This application is a divisional of U.S. patent application Ser. No. 12/565,807 filed Sep. 24, 2009 now abandoned which is a divisional of U.S. patent application Ser. No. 11/334,085 filed Jan. 18, 2006, issued as U.S. Pat. No. 7,615,624, which is a continuation-in-part of Ser. No. 09/887,567 filed Jun. 22, 2001, now abandoned, which claims the benefit of U.S. Provisional Application Ser. No. 60/214,087 filed Jun. 23, 2000, U.S. Provisional Application Ser. No. 60/213,848 filed Jun. 23, 2000, and U.S. Provisional Application Ser. No. 60/258,692, filed Dec. 29, 2000 under 35 U.S.C. §119(e), the entire disclosures of which are incorporated by reference herein.

FIELD OF INVENTION

The present invention relates generally to the field of plant molecular biology. More specifically, it relates to the regulation of gene expression in plants.

BACKGROUND OF INVENTION

Manipulation of crop plants to alter and/or improve phenotypic characteristics (such as productivity or quality) requires the expression of heterologous genes in plant tissues. Such genetic manipulation relies on the availability of a means to drive and to control gene expression as required. For example, genetic manipulation relies on the availability and use of suitable promoters which are effective in plants and which regulate gene expression so as to give the desired effect(s) in the transgenic plant. It is advantageous to have the choice of a variety of different promoters so that the most suitable promoter may be selected for a particular gene, construct, cell, tissue, plant or environment. Moreover, the increasing interest in cotransforming plants with multiple plant transcription units (PTU) and the potential problems associated with using common regulatory sequences for these purposes merit having a variety of promoter sequences available.

Promoters (and other regulatory components) from bacteria, viruses, fungi and plants have been used to control gene expression in plant cells. Numerous plant transformation experiments using DNA constructs comprising various promoter sequences fused to various foreign genes (for example, bacterial marker genes) have led to the identification of useful promoter sequences. It has been demonstrated that sequences up to 500-1000 bases in most instances are sufficient to allow for the regulated expression of foreign genes. However, it has also been shown that sequences much longer than 1000 bases may have useful features which permit desirable, e.g., high, levels of gene expression in transgenic plants.

One desirable source for promoters which have different expression profiles is plant genomic DNA. Plant development is precisely coordinated and regulated through transcription and translation of different gene products in each cell. The expression level for each gene present in a cell not only reflects the physiological status of the cell, but also determines the range of different functions the cell can perform. Identification of genes expressed constitutively, in a specific cell type or tissue, or at a specific developmental stage, and the analysis of the abundance of the corresponding gene product can provide valuable insights into basic molecular processes and identity promoters with desirable properties.

cDNA and high density oligonucleotide array technology allows analysis of mRNA transcripts of hundreds to thousands of genes in parallel (Schena et al., 1995; Chee et al., 1996; Lockhart et al., 1996; DeRisi et al., 1997; Lashkari et al., 1997). In some organisms with completed genome sequences, such as yeast, global gene expression profiling at the mRNA level becomes possible (DeRisi et al., 1997). Genome scale transcription profiling enables not only parallel monitoring of gene expression, but also a more subjective approach for gene discovery because objective selection of gene probes to be put on microarrays is not required (Lockhart and Winzeler, 2000).

Microarray technology has been successfully developed for studying gene expression in plants (Schena et al., 1995; Desprez et al., 1998; Yuan et al., 1998; Giege et al., 1998; Kehoe et al., 1999). The microarrays used in those studies were cDNA microarrays on glass slides or filter membranes (Duggan et al. 1999; Southern et al. 1999). The DNA probes often consist of DNA fragments of expression sequence tags (ESTs) from various *Arabidopsis* EST projects (i.e., Newman et al., 1994, Richmond et al., 2000, Schaffer et al., 2000). Microarrays with selected subsets of gene probes (usually in the hundreds) has been used to examine differences in gene expression during organ development (Yuan et al., 1998; Aharoni et al., 2000), and has revealed genes that are correlated or responsible for the defense response (Reymond et al., 2000).

There is, therefore, a great need in the art for the identification of novel sequences that can be used for expression of selected transgenes in economically important plants. More specifically, there is a need for the systematic identification of genes that are expressed in a particular manner, e.g., using microarray technology.

SUMMARY OF INVENTION

The present invention provides an isolated nucleic acid molecule (polynucleotide) having a plant nucleotide sequence that directs transcription of a linked nucleic acid segment in a plant or plant cell, e.g., a linked plant DNA comprising an open reading frame for a structural or regulatory gene. The nucleotide sequence preferably is obtained or isolatable from plant genomic DNA.

The present invention also provides an isolated nucleic acid molecule having a plant nucleotide sequence that directs constitutive transcription of a linked nucleic acid segment in a host cell, e.g., a plant cell. The nucleotide sequence preferably is obtained or isolatable from plant genomic DNA. In particular, the nucleotide sequence is obtained or isolatable from an *Arabidopsis* gene which directs constitutive transcription of a linked nucleic acid segment.

The present invention further provides an isolated nucleic acid molecule which comprises a plant nucleotide sequence that directs leaf-specific (i.e., preferential) transcription of a linked nucleic acid segment in a plant.

Thus, the presently disclosed subject matter provides in some embodiments isolated polynucleotides comprising a plant nucleotide sequence that directs transcription of an operatively linked nucleic acid segment in a plant cell. In some embodiments, the plant nucleotide sequences hybridize under high stringency conditions to a complement of a sequence selected from the group consisting of SEQ ID NO:1-26. In some embodiments, the plant nucleotide sequence hybridizes under very high stringency conditions to the complement of SEQ ID NO: 1-26. In some embodiments, the plant nucleotide sequence is a functional fragment from 25 to 2000 nucleotides in length.

The presently disclosed subject matter also provides expression cassettes comprising the disclosed polynucleotides operatively linked to an open reading frame. In some embodiments, the open reading frame comprises a gene which, when transcribed at the direction of the polynucleotide, imparts a phenotype selected from the group consisting of insect resistance, disease resistance, herbicide resistance, abiotic stress resistance, a modified enzyme expression profile, a modified oil content, and a modified nutrient content.

The presently disclosed subject matter further provides transformed plants, the genome of which is augmented with one or more of the disclosed expression cassettes. In some embodiments, the transformed plant is a monocot or a dicot plant. In some embodiments, the transformed plant is a cereal plant. In some embodiments, the cereal plant is selected from the group consisting of maize, wheat, rice, sorghum, and barley. In some embodiments, the transformed dicot plant of claim 8 wherein the dicot is selected from the group consisting of soybean, cotton, canola, and sugarbeet The presently disclosed subject matter also provides cells of the disclosed transformed plants, which are characterized as having in their genomic DNAs the disclosed expression cassettes.

As described herein, GENECHIP® technology was utilized to discover genes that are preferentially (or exclusively) expressed in various tissues including root and leaf, as well as those that are constitutively expressed, using labeled cRNA probes, determining expression levels by laser scanning and generally selecting for expression levels that were >2 fold over the control. The *Arabidopsis* oligonucleotide probe array consists of probes from about 8,100 unique *Arabidopsis* genes, which covers approximately one third of the genome. This genome array permits a broader, more complete and less biased analysis of gene expression. Using this approach, 51 genes were identified, the expression of which was altered, e.g., elevated, in root tissues, and 92 genes were identified, the expression of which was altered at least 4-fold in leaf tissue. Similarly, 288 genes were identified that were constitutively expressed.

Generally, the promoters of the invention may be employed to express an open reading frame from an insect resistance gene, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a gene affecting plant agronomic characteristics, or an environment or stress resistance gene, i.e., one or more genes that confer herbicide resistance or tolerance, insect resistance or tolerance, disease resistance or tolerance (viral, bacterial, fungal, oomycete, or nematode), stress tolerance or resistance (as exemplified by resistance or tolerance to drought, heat, chilling, freezing, excessive moisture, salt stress, or oxidative stress), increased yields, food content and makeup, physical appearance, male sterility, drydown, standability, prolificacy, starch properties or quantity, oil quantity and quality, amino acid or protein composition, and the like. By "resistant" is meant a plant which exhibits substantially no phenotypic changes as a consequence of agent administration, infection with a pathogen, or exposure to stress. By "tolerant" is meant a plant which, although it may exhibit some phenotypic changes as a consequence of infection, does not have a substantially decreased reproductive capacity or substantially altered metabolism.

In particular, root-specific promoters may be useful for expressing defense-related genes, including those conferring insecticidal resistance and stress tolerance genes, e.g., salt, cold or drought tolerance, and genes for altering nutrient uptake, and leaf-specific promoters may be useful for producing large quantities of protein, for expressing oils or proteins of interest, genes for increasing the nutritional value of a plant, and for expressing defense-related genes (e.g., against pathogens such as a virus or fungus), including genes encoding insecticidal polypeptides. Constitutive promoters are useful for expressing a wide variety of genes including those which alter metabolic pathways, confer disease resistance, for protein production, e.g., antibody production, or to improve nutrient uptake. Constitutive promoters may be modified so as to be regulatable, e.g., inducible.

The genes and promoters described hereinabove can be used to identify orthologous genes and their promoters which are also likely expressed in a particular tissue and/or development manner. Moreover, the orthologous promoters are useful to express linked open reading frames. In addition, by aligning the promoters of these orthologs, novel cis elements can be identified that are useful to generate synthetic promoters. Hence, the isolated nucleic acid molecules of the invention include the orthologs of the *Arabidopsis* sequences disclosed herein, i.e., the corresponding nucleotide sequences in organisms other than *Arabidopsis*, including, but not limited to, plants other than *Arabidopsis*, preferably cereal plants, e.g., corn, wheat, rye, turfgrass, sorghum, millet, sugarcane, soybean, barley, alfalfa, sunflower, canola, soybean, cotton, peanut, tobacco, sugarbeet, or rice. An orthologous gene is a gene from a different species that encodes a product having the same or similar function, e.g., catalyzing the same reaction as a product encoded by a gene from a reference organism. Thus, an ortholog includes polypeptides having less than, e.g., 65% amino acid sequence identity, but which ortholog encodes a polypeptide having the same or similar function. Databases such GENBANK® may be employed to identify sequences related to the *Arabidopsis* sequences, e.g., orthologs in cereal crops such as rice, wheat, sunflower or alfalfa.

Preferably, the promoters of the invention include a consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NOs:1-26, or the promoter orthologs thereof, which include the minimal promoter region.

In a particular embodiment of the invention said consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, has at least 75%, preferably 80%, more preferably 90% and most preferably 95% sequence identity with a corresponding consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NOs:1-26, or the promoter orthologs thereof, which include the minimal promoter region.

In a preferred embodiment of the invention said consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, has at least 75%, preferably 80%, more preferably 90% and most preferably 95% sequence identity with a corresponding consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NOs: 1-26, or the promoter orthologs thereof, which include the minimal promoter region.

Preferably, the nucleotide sequence that includes the promoter region includes at least one copy of a TATA box and, for leaf-specific expression, preferably a light responsive element. Thus, the invention provides plant promoters, including orthologs of Arabidopsis promoters corresponding to any one of SEQ ID NOs: 1-26 and orthologs thereof. The present invention further provides a composition, an expression cassette or a recombinant vector (e.g., a plasmid, phagemid, cosmid, virus, F-factor or phage) containing the nucleic acid molecule of the invention, and host cells, e.g., a plant cell, comprising the expression cassette or vector, e.g., comprising a plasmid. In particular, the present invention provides an expression cassette or a recombinant vector comprising a promoter of the invention linked to a nucleic acid segment which, when present in a plant, plant cell or plant tissue, results in transcription of the linked nucleic acid segment.

In its broadest sense, the term "substantially similar" when used herein with respect to a nucleotide sequence means that the nucleotide sequence is part of a gene which encodes a polypeptide having substantially the same structure and function as a polypeptide encoded by a gene for the reference nucleotide sequence, e.g., the nucleotide sequence comprises a promoter from a gene that is the ortholog of the gene corresponding to the reference nucleotide sequence, as well as promoter sequences that are structurally related the promoter sequences particularly exemplified herein, i.e., the substantially similar promoter sequences hybridize to the complement of the promoter sequences exemplified herein under high or very high stringency conditions. The term "substantially similar" thus includes nucleotide sequences wherein the sequence has been modified, for example, to optimize expression in particular cells, as well as nucleotide sequences encoding a variant polypeptide having one or more amino acid substitutions relative to the (unmodified) polypeptide encoded by the reference sequence, which substitution(s) does not alter the activity of the variant polypeptide relative to the unmodified polypeptide. In its broadest sense, the term "substantially similar" when used herein with respect to polypeptide means that the polypeptide has substantially the same structure and function as the reference polypeptide. The percentage of amino acid sequence identity between the substantially similar and the reference polypeptide is at least 65%, 66%, 67%, 68%, 69%, 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99%, wherein the reference polypeptide is an Arabidopsis polypeptide encoded by a gene with a promoter having any one of SEQ ID NOs:1-26. One indication that two polypeptides are substantially similar to each other, besides having substantially the same function, is that an agent, e.g., an antibody, which specifically binds to one of the polypeptides, specifically binds to the other.

Sequence comparisons maybe carried out using a Smith-Waterman sequence alignment algorithm (see e.g., Waterman (1995)). The localS program, version 1.16, is preferably used with following parameters: match: 1, mismatch penalty: 0.33, open-gap penalty: 2, extended-gap penalty: 2. Further, a nucleotide sequence that is "substantially similar" to a reference nucleotide sequence hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C.

In one embodiment, the invention provides an expression cassette or vector containing an isolated nucleic acid molecule having a nucleotide sequence that directs root-specific, constitutive, or leaf-specific transcription of a linked nucleic acid segment in a cell, which nucleotide sequence comprises one or more of SEQ ID NOs: 1-26. This expression cassette or vector may be contained in a host cell. The expression cassette or vector may augment the genome of a transformed plant or may be maintained extrachromosomally. The expression cassette may be operatively linked to a structural gene, the open reading frame thereof, or a portion thereof. The expression cassette may further comprise a Ti plasmid and be contained in an Agrobacterium tumefaciens cell; it may be carried on a microparticle, wherein the microparticle is suitable for ballistic transformation of a plant cell; or it may be contained in a plant cell or protoplast. Further, the expression cassette or vector can be contained in a transformed plant or cells thereof, and the plant may be a dicot or a monocot. In particular, the plant may be a cereal plant.

The present invention further provides a method of augmenting a plant genome by contacting plant cells with a nucleic acid molecule of the invention, e.g., one having a nucleotide sequence that directs root-specific, constitutive or leaf-specific transcription of a linked nucleic acid segment, so as to yield transformed plant cells; and regenerating the transformed plant cells to provide a differentiated transformed plant, wherein the differentiated transformed plant expresses the nucleic acid molecule in the cells of the plant. The nucleic acid molecule may be present in the nucleus, chloroplast, mitochondria and/or plastid of the cells of the plant. The present invention also provides a transgenic plant prepared by this method, a seed from such a plant and progeny plants from such a plant including hybrids and inbreds. Preferred transgenic plants are transgenic maize, soybean, barley, alfalfa, sunflower, canola, soybean, cotton, peanut, sorghum, tobacco, sugarbeet, rice, wheat, rye, turfgrass, millet, sugarcane, tomato, or potato.

A transformed (transgenic) plant of the invention includes plants, for example, a plant having transformed plant cells which cells contain an expression cassette having a polynucleotide of the invention, or the genome of which is augmented by a nucleic acid molecule of the invention, or in which the corresponding gene has been disrupted, e.g., to result in a loss, a decrease or an alteration, in the function of the product encoded by the gene, which plant may also have increased yields and/or produce a better-quality product than the corresponding wild-type plant. The nucleic acid molecules of the invention are thus useful for targeted gene disruption, as well as markers and probes.

The invention also provides a method of plant breeding, e.g., to prepare a crossed fertile transgenic plant. The method comprises crossing a fertile transgenic plant comprising a particular nucleic acid molecule of the invention with itself or with a second plant, e.g., one lacking the particular nucleic acid molecule, to prepare the seed of a crossed fertile transgenic plant comprising the particular nucleic acid molecule.

The seed is then planted to obtain a crossed fertile transgenic plant. The plant may be a monocot or a dicot. In a particular embodiment, the plant is a cereal plant.

The crossed fertile transgenic plant may have the particular nucleic acid molecule inherited through a female parent or through a male parent. The second plant may be an inbred plant. The crossed fertile transgenic may be a hybrid. Also included within the present invention are seeds of any of these crossed fertile transgenic plants.

The various breeding steps are characterized by well-defined human intervention such as selecting the lines to be crossed, directing pollination of the parental lines, or selecting appropriate progeny plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic plants according to the invention can be used for the breeding of improved plant lines that for example increase the effectiveness of conventional methods such as herbicide or pesticide treatment or allow to dispense with said methods due to their modified genetic properties. Alternatively new crops with improved stress tolerance can be obtained that, due to their optimized genetic "equipment", yield harvested product of better quality than products that were not able to tolerate comparable adverse developmental conditions.

The present invention also provides a method to identify a nucleotide sequence that directs root-specific transcription of linked nucleic acid in the genome of a plant cell by contacting a probe of plant nucleic acid, e.g., cRNA, isolated from root as well as other tissues of a plant, with a plurality of isolated nucleic acid samples on one or more, i.e., a plurality of, solid substrates so as to form a complex between at least a portion of the probe and a nucleic acid sample(s) having sequences that are structurally related to the sequences in the probe. Each sample comprises one or a plurality of oligonucleotides corresponding to at least a portion of a plant gene. Then complex formation is compared between samples contacted with the root-specific probe and samples contacted with a non-root specific probe so as to determine which RNAs are expressed in root tissues of the plant. The probe and/or samples may be nucleic acid from a dicot or from a monocot.

The present invention also provides a method to identify a nucleotide sequence that directs constitutive transcription of nucleic acid in the genome of a plant cell by contacting a probe of plant nucleic acid, e.g., cRNA, isolated from various tissues of a plant and at various developmental stages with a plurality of isolated nucleic acid samples on one or more, i.e., a plurality of, solid substrates so as to form a complex between at least a portion of the probe and a nucleic acid sample(s) having sequences that are structurally related to the sequences in the probe. Each sample comprises one or a plurality of oligonucleotides corresponding to at least a portion of a plant gene. Complex formation is then compared to determine which RNAs are present in a majority of, preferably in substantially all, tissues, in a majority of, preferably at substantially all, developmental stages of the plant. The probe and/or samples may be nucleic acid from a dicot or from a monocot.

The present invention also provides a method to identify a nucleotide sequence that directs transcription of nucleic acid in the genome of a plant cell in leaf tissue, by contacting a probe of plant nucleic acid, e.g., cRNA, isolated from leaf as well as other tissues of a plant with a plurality of isolated nucleic acid samples on one or more, i.e., a plurality of, solid substrates, so as to form a complex between at least a portion of the probe and a nucleic acid sample(s) having sequences that are structurally related to the sequences in the probe. Each sample comprises one or a plurality of, oligonucleotides corresponding to at least a portion of a plant gene. Then complex formation is determined or detected to identify which samples represent genes that are expressed in leaf. The probe and/or samples may be nucleic acid from a dicot or from a monocot.

The invention further includes a nucleotide sequence which is complementary to one (hereinafter "test" sequence) which hybridizes under stringent conditions with a nucleic acid molecule of the invention as well as RNA which is transcribed from the nucleic acid molecule. When the hybridization is performed under stringent conditions, either the test or nucleic acid molecule of invention is preferably supported, e.g., on a membrane or DNA chip. Thus, either a denatured test or nucleic acid molecule of the invention is preferably first bound to a support and hybridization is effected for a specified period of time at a temperature of, e.g., between 55 and 70° C., in double strength citrate buffered saline (SC) containing 0.1% SDS followed by rinsing of the support at the same temperature but with a buffer having a reduced SC concentration. Depending upon the degree of stringency required such reduced concentration buffers are typically single strength SC containing 0.1% SDS, half strength SC containing 0.1% SDS and one-tenth strength SC containing 0.1% SDS.

A computer readable medium, e.g., a magnetic tape, optical disk, CD-ROM, random access memory, volatile memory, non-volatile memory, or bubble memory, containing one or more of the nucleotide sequences of the invention as well as methods of use for the computer readable medium are provided. This medium allows a nucleotide sequence corresponding to at least one of SEQ ID NOs:1-26, or, e.g., a nucleic acid molecule that has at least 70% nucleic acid sequence identity to at least one of SEQ ID NOs:1-26 or the complement thereof, to be used as a reference sequence to search against a database. This medium also allows for computer-based manipulation of a nucleotide sequence corresponding to at least one of SEQ ID NOs: 1-26.

DETAILED DESCRIPTION OF THE INVENTION

In accordance with the present invention, nucleic acid constructs are provided that allow initiation of transcription in a "root-specific" or "leaf-specific" manner. Constructs of the invention comprise regulated transcription initiation regions associated with protein translation elongation, and the compositions of the present invention are drawn to novel nucleotide sequences for root-specific as well as leaf-specific expression. The present invention thus provides for isolated nucleic acid molecules comprising a plant nucleotide sequence that directs transcription of a linked nucleic acid fragment in a plant cell. Thus, these nucleotide sequences exhibit promoter activity in, for example, root or leaf tissues. Promoters may be obtained from other plant species by using the *Arabidopsis* promoter sequences described herein as probes to screen for homologous promoters in other plants by hybridization under low, moderate or stringent hybridization conditions. Regions of the promoter sequences of the present invention which are conserved among species could also be used as PCR primers to amplify a segment from a species other than *Arabidopsis*, and that segment used as a hybridization probe (the latter approach permitting higher stringency screening) or in a transcriptional assay to determine promoter activity. Moreover, the promoter sequences could be employed to identify structurally related sequences in a database using computer algorithms.

These promoters are capable of driving the expression of a coding sequence in a target cell, particularly in a plant cell. The promoter sequences and methods disclosed herein are useful in regulating in some embodiments tissue-specific expression of any heterologous nucleotide sequence in a host plant in order to vary the phenotype of that plant. These promoters can be used with combinations of enhancer, upstream elements, and/or activating sequences from the 5' flanking regions of plant expressible structural genes. Similarly the upstream element can be used in combination with various plant promoter sequences.

Also in accordance with the present invention, nucleic acid constructs are provided that allow initiation of transcription in a "tissue-independent," "tissue general," or "constitutive" manner. Constructs of this embodiment invention comprise regulated transcription initiation regions associated with protein translation elongation and the compositions of this embodiment of the present invention are drawn to novel nucleotide sequences for tissue-independent, tissue-general, or constitutive plant promoters. By "tissue-independent," "tissue-general," or "constitutive" is intended expression in the cells throughout a plant at most times and in most tissues. As with other promoters classified as "constitutive" (e.g., ubiquitin), some variation in absolute levels of expression can exist among different tissues or stages.

The present invention thus provides for isolated nucleic acid molecules comprising a plant nucleotide sequence that directs constitutive transcription of a linked nucleic acid fragment in a plant cell. Preferably, the nucleotide sequence is obtained from plant genomic DNA. Constitutive promoter sequences may be obtained from other plant species by using the constitutive *Arabidopsis* promoter sequences described herein as probes to screen for homologous structural genes in other plants by hybridization under low, moderate or stringent hybridization conditions. Regions of the constitutive promoter sequences of the present invention which are conserved among species could also be used as PCR primers to amplify a segment from a species other than *Arabidopsis*, and that segment used as a hybridization probe (the latter approach permitting higher stringency screening) or in a transcription assay to determine promoter activity. Moreover, the constitutive promoter sequences could be employed to identify structurally related sequences in a database using computer algorithms.

These constitutive promoters are capable of driving the expression of a coding sequence in a target cell, particularly in a plant cell. The promoter sequences and methods disclosed herein are useful in regulating constitutive expression of any heterologous nucleotide sequence in a host plant in order to vary the phenotype of that plant. These promoters can be used with combinations of enhancer, upstream elements, and/or activating sequences from the 5' flanking regions of plant expressible structural genes. Similarly the upstream element can be used in combination with various plant promoter sequences. In one embodiment the promoter and upstream element are used together to obtain at least 10-fold higher expression of an introduced gene in monocot transgenic plants than is obtained with the maize ubiquitin 1 promoter.

In particular, all of the promoters of the invention are useful to modify the phenotype of a plant. Various changes in the phenotype of a transgenic plant are desirable, i.e., modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in an alteration in the phenotype of the transformed plant.

I. Definitions

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA or functional RNA, or encodes a specific protein, and which includes regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The term "native" or "wild type" gene refers to a gene that is present in the genome of an untransformed cell, i.e., a cell not having a known mutation.

A "marker gene" encodes a selectable or screenable trait.

The term "chimeric gene" refers to any gene that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

An "oligonucleotide" corresponding to a nucleotide sequence of the invention, e.g., for use in probing or amplification reactions, may be about 30 or fewer nucleotides in length (e.g., 9, 12, 15, 18, 20, 21 or 24, or any number between 9 and 30). Generally specific primers are upwards of 14 nucleotides in length. For optimum specificity and cost effectiveness, primers of 16 to 24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

The terms "protein," "peptide" and "polypeptide" are used interchangeably herein.

The nucleotide sequences of the invention can be introduced into any plant. The genes to be introduced can be conveniently used in expression cassettes for introduction and expression in any plant of interest. Such expression cassettes will comprise the transcriptional initiation region of the invention linked to a nucleotide sequence of interest. Preferred promoters include constitutive, tissue-specific, developmental-specific, inducible and/or viral promoters. Such an expression cassette is provided with a plurality of restriction sites for insertion of the gene of interest to be under the transcriptional regulation of the regulatory regions. The expression cassette may additionally contain selectable marker genes. The cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al., 1991; Proudfoot, 1991; Sanfacon et al., 1991; Mogen et al., 1990; Munroe et al., 1990; Ballas et al., 1989; Joshi et al., 1987.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complimentary copy of the DNA sequence, it is referred to as the primary transcript or it may be a RNA sequence derived from post-transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences. As is noted above, the term "suitable regulatory sequences" is not limited to promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., 1995).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., 1989.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

The term "intracellular localization sequence" refers to a nucleotide sequence that encodes an intracellular targeting signal. An "intracellular targeting signal" is an amino acid sequence that is translated in conjunction with a protein and directs it to a particular sub-cellular compartment. "Endoplasmic reticulum (ER) stop transit signal" refers to a carboxy-terminal extension of a polypeptide, which is translated in conjunction with the polypeptide and causes a protein that enters the secretory pathway to be retained in the ER. "ER stop transit sequence" refers to a nucleotide sequence that encodes the ER targeting signal. Other intracellular targeting sequences encode targeting signals active in seeds and/or leaves and vacuolar targeting signals.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Constitutive promoter" refers to a promoter that is able to express the open reading frame (ORF) that it controls in all or nearly all of the plant tissues during all or nearly all developmental stages of the plant. Each of the transcription-activating elements do not exhibit an absolute tissue-specificity, but mediate transcriptional activation in most plant parts at a level of $\geq 1\%$ of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysome-inducible systems.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Inducible promoter" refers to those regulated promoters that can be turned on in one or more cell types by an external stimulus, such as a chemical, light, hormone, stress, or a pathogen.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Specific expression" is the expression of gene products which is limited to one or a few plant tissues (spatial limitation) and/or to one or a few plant developmental stages (temporal limitation). It is acknowledged that hardly a true specificity exists: promoters seem to be preferably switch on in some tissues, while in other tissues there can be no or only little activity. This phenomenon is known as leaky expression. However, with specific expression in this invention is meant preferable expression in one or a few plant tissues.

The "expression pattern" of a promoter (with or without enhancer) is the pattern of expression levels which shows where in the plant and in what developmental stage transcription is initiated by said promoter. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore, the steady state level is the product of synthesis rates and degradation rates.

The rate of degradation can however be considered to proceed at a fixed rate when the transcribed sequences are identical, and thus this value can serve as a measure of synthesis rates. When promoters are compared in this way techniques available to those skilled in the art are hybridization S1-RNAse analysis, northern blots and competitive RT-PCR. This list of techniques in no way represents all available techniques, but rather describes commonly used procedures used to analyze transcription activity and expression levels of mRNA.

The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to suboptimal levels of transcription.

A commonly used procedure to analyze expression patterns and levels is through determination of the 'steady state' level of protein accumulation in a cell. Commonly used candidates for the reporter gene, known to those skilled in the art are β-glucuronidase (GUS), chloramphenicol acetyl transferase (CAT) and proteins with fluorescent properties, such as green fluorescent protein (GFP) from *Aequora victoria*. In principle, however, many more proteins are suitable for this purpose, provided the protein does not interfere with essential plant functions. For quantification and determination of localization a number of tools are suited. Detection systems can readily be created or are available which are based on, e.g., immunochemical, enzymatic, fluorescent detection and quantification. Protein levels can be determined in plant tissue extracts or in intact tissue using in situ analysis of protein expression.

Generally, individual transformed lines with one chimeric promoter reporter construct will vary in their levels of expression of the reporter gene. Also frequently observed is the phenomenon that such transformants do not express any detectable product (RNA or protein). The variability in expression is commonly ascribed to 'position effects', although the molecular mechanisms underlying this inactivity are usually not clear.

The term "average expression" is used here as the average level of expression found in all lines that do express detectable amounts of reporter gene, so leaving out of the analysis plants that do not express any detectable reporter mRNA or protein.

"Root expression level" indicates the expression level found in protein extracts of complete plant roots. Likewise, leaf, and stem expression levels, are determined using whole extracts from leaves and stems. It is acknowledged however, that within each of the plant parts just described, cells with variable functions may exist, in which promoter activity may vary.

"Non-specific expression" refers to constitutive expression or low level, basal ('leaky') expression in nondesired cells or tissues from a 'regulated promoter'.

"Altered levels" refers to the level of expression in transgenic organisms that differs from that of normal or untransformed organisms.

"Overexpression" refers to the level of expression in transgenic cells or organisms that exceeds levels of expression in normal or untransformed (nontransgenic) cells or organisms.

"Antisense inhibition" refers to the production of antisense RNA transcripts capable of suppressing the expression of protein from an endogenous gene or a transgene.

"Co-suppression" and "transwitch" each refer to the production of sense RNA transcripts capable of suppressing the expression of identical or substantially similar transgene or endogenous genes (U.S. Pat. No. 5,231,020).

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes (English et al., 1996). Gene silencing includes virus-induced gene silencing (Ruiz et al. 1998).

"Silencing suppressor" gene refers to a gene whose expression leads to counteracting gene silencing and enhanced expression of silenced genes. Silencing suppressor genes may be of plant, non-plant, or viral origin. Examples include, but are not limited to HC-Pro, P1-HC-Pro, and 2b proteins. Other examples include one or more genes in TGMV-B genome.

The terms "heterologous DNA sequence," "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

"Homologous to" in the context of nucleotide sequence identity refers to the similarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (as described in Haines and Higgins (eds.), Nucleic Acid Hybridization, IRL Press, Oxford, U.K.), or by the comparison of sequence similarity between two nucleic acids or proteins.

The term "substantially similar" refers to nucleotide and amino acid sequences that represent functional and/or structural equivalents of *Arabidopsis* sequences disclosed herein. For example, altered nucleotide sequences which simply reflect the degeneracy of the genetic code but nonetheless encode amino acid sequences that are identical to a particular amino acid sequence are substantially similar to the particular sequences. In addition, amino acid sequences that are substantially similar to a particular sequence are those wherein overall amino acid identity is at least 65% or greater to the instant sequences. Modifications that result in equivalent nucleotide or amino acid sequences are well within the routine skill in the art. Moreover, the skilled artisan recognizes that equivalent nucleotide sequences encompassed by this invention can also be defined by their ability to hybridize, under low, moderate and/or stringent conditions (e.g., 0.1× SSC, 0.1% SDS, 65° C.), with the nucleotide sequences that are within the literal scope of the instant claims.

"Target gene" refers to a gene on the replicon that expresses the desired target coding sequence, functional RNA, or protein. The target gene is not essential for replicon replication. Additionally, target genes may comprise native non-viral genes inserted into a non-native organism, or chimeric genes, and will be under the control of suitable regulatory sequences. Thus, the regulatory sequences in the target gene may come from any source, including the virus. Target genes may include coding sequences that are either heterologous or homologous to the genes of a particular plant to be transformed. However, target genes do not include native viral genes. Typical target genes include, but are not limited to genes encoding a structural protein, a seed storage protein, a protein that conveys herbicide resistance, and a protein that conveys insect resistance. Proteins encoded by target genes are known as "foreign proteins". The expression of a target gene in a plant will typically produce an altered plant trait.

The term "altered plant trait" means any phenotypic or genotypic change in a transgenic plant relative to the wild-type or non-transgenic plant host.

"Transcription Stop Fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Replication gene" refers to a gene encoding a viral replication protein. In addition to the ORF of the replication protein, the replication gene may also contain other overlapping or non-overlapping ORF(s), as are found in viral sequences in nature. While not essential for replication, these additional ORFs may enhance replication and/or viral DNA accumulation. Examples of such additional ORFs are AC3 and AL3 in ACMV and TGMV geminiviruses, respectively.

"Chimeric trans-acting replication gene" refers either to a replication gene in which the coding sequence of a replication protein is under the control of a regulated plant promoter other than that in the native viral replication gene, or a modified native viral replication gene, for example, in which a site specific sequence(s) is inserted in the 5' transcribed but untranslated region. Such chimeric genes also include insertion of the known sites of replication protein binding between the promoter and the transcription start site that attenuate transcription of viral replication protein gene.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

"Production tissue" refers to mature, harvestable tissue consisting of non-dividing, terminally-differentiated cells. It excludes young, growing tissue consisting of germline, meristematic, and not-fully-differentiated cells.

"Germline cells" refer to cells that are destined to be gametes and whose genetic material is heritable.

"Trans-activation" refers to switching on of gene expression or replicon replication by the expression of another (regulatory) gene in trans.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms". Examples of methods of transformation of plants and plant cells include Agrobacterium-mediated transformation (De Blaere et al., 1987) and particle bombardment technology (Klein et al. 1987; U.S. Pat. No. 4,945,050). Whole plants may be regenerated from transgenic cells by methods well known to the skilled artisan (see, for example, Fromm et al., 1990).

"Transformed," "transgenic," and "recombinant" refer to a host organism such as a bacterium or a plant into which a heterologous nucleic acid molecule has been introduced. The nucleic acid molecule can be stably integrated into the genome generally known in the art and are disclosed in Sambrook et al., 1989. See also Innis et al., 1995 and Gelfand, 1995; and Innis and Gelfand, 1999. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" plants or calli have been through the transformation process and contain a foreign gne integrated into their chromosome. The term "untransformed" refers to normal plants that have not been through the transformation process.

"Transiently transformed" refers to cells in which transgenes and foreign DNA have been introduced (for example, by such methods as Agrobacterium-mediated transformation or biolistic bombardment), but not selected for stable maintenance.

"Stably transformed" refers to cells that have been selected and regenerated on a selection media following transformation.

"Transient expression" refers to expression in cells in which a virus or a transgene is introduced by viral infection or by such methods as Agrobacterium-mediated transformation, electroporation, or biolistic bombardment, but not selected for its stable maintenance.

"Genetically stable" and "heritable" refer to chromosomally-integrated genetic elements that are stably maintained in the plant and stably inherited by progeny through successive generations.

"Primary transformant" and "T0 generation" refer to transgenic plants that are of the same genetic generation as the tissue which was initially transformed (i.e., not having gone through meiosis and fertilization since transformation).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Wild-type" refers to a virus or organism found in nature without any known mutation.

"Genome" refers to the complete genetic material of an organism.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991; Ohtsuka et al., 1985; Rossolini et al. 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals.

The nucleotide sequences of the invention include both the naturally occurring sequences as well as mutant (variant) forms. Such variants will continue to possess the desired activity, i.e., either promoter activity or the activity of the product encoded by the open reading frame of the non-variant nucleotide sequence.

Thus, by "variants" is intended substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

The nucleic acid molecules of the invention can be "optimized" for enhanced expression in plants of interest. See, for example, EPA 035472; WO 91/16432; Perlak et al., 1991; and Murray et al., 1989. In this manner, the open reading frames in genes or gene fragments can be synthesized utilizing plant-preferred codons. See, for example, Campbell and Gowri, 1990 for a discussion of host-preferred codon usage. Thus, the nucleotide sequences can be optimized for expression in any plant. It is recognized that all or any part of the gene sequence may be optimized or synthetic. That is, synthetic or partially optimized sequences may also be used. Variant nucleotide sequences and proteins also encompass sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer, 1994; Stemmer, 1994; Crameri et al., 1997; Moore et al., 1997; Zhang et al., 1997; Crameri et al., 1998; and U.S. Pat. Nos. 5,605,793 and 5,837,458.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, 1985; Kunkel et al., 1987; U.S. Pat. No. 4,873,192; Walker and Gaastra, 1983 and the references cited therein. Guidance as to appropriate amino acid substitutions that do not affect biological activity of the protein of interest may be found in the model of Dayhoff et al. (1978). Conservative substitutions, such as exchanging one amino acid with another having similar properties, are preferred.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine I, Lysine (K), Histidine (H); Acidic: Aspartic acid (D), Glutamic acid (E), Asparagine (N), Glutamine (Q). See also, Creighton, 1984. In addition, individual substitutions, deletions or additions which alter, add or delete a single amino acid or a small percentage of amino acids in an encoded sequence are also "conservatively modified variations."

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

"Vector" is defined to include, inter alia, any plasmid, cosmid, phage or *Agrobacterium* binary vector in double or single stranded linear or circular form which may or may not be self transmissible or mobilizable, and which can transform a prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

A "transgenic plant" is a plant having one or more plant cells that contain an expression vector.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. 1988; Higgins et al. 1989; Corpet et al. 1988; Huang et al. 1992; and Pearson et al. 1994. The ALIGN program is based on the algorithm of Myers and Miller, supra. The BLAST programs of Altschul et al., 1990, are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984; $T_m$ 81.5° C.+16.6 (log M)+0.41 (% GC)− 0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1.times. to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C.

"DNA shuffling" is a method to introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA preferably encodes a variant polypeptide modified with respect to the polypeptide encoded by the template DNA, and may have an altered biological activity with respect to the polypeptide encoded by the template DNA.

"Recombinant DNA molecule" is a combination of DNA sequences that are joined together using recombinant DNA technology and procedures used to join together DNA sequences as described, for example, in Sambrook et al., 1989.

The word "plant" refers to any plant, particularly to seed plant, and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ.

"Significant increase" is an increase that is larger than the margin of error inherent in the measurement technique, preferably an increase by about 2-fold or greater.

"Significantly less" means that the decrease is larger than the margin of error inherent in the measurement technique, preferably a decrease by about 2-fold or greater.

II. DNA Sequences for Transformation

Virtually any DNA composition may be used for delivery to recipient plant cells, e.g., monocotyledonous cells, to ultimately produce fertile transgenic plants in accordance with the present invention. For example, DNA segments in the form of vectors and plasmids, or linear DNA fragments, in some instances containing only the DNA element to be expressed in the plant, and the like, may be employed. The construction of vectors which may be employed in conjunction with the present invention will be known to those of skill of the art in light of the present disclosure (see, e.g., Sambrook et al., 1989; Gelvin et al., 1990).

Vectors, plasmids, cosmids, YACs (yeast artificial chromosomes), BACs (bacterial artificial chromosomes) and DNA segments for use in transforming such cells will, of course, generally comprise the cDNA, gene or genes which one desires to introduce into the cells. These DNA constructs can further include structures such as promoters, enhancers, polylinkers, or even regulatory genes as desired. The DNA segment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes.

In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki et al., 1991). These vectors are capable of autonomous replication in maize cells as well as E. coli, and as such may provide increased sensitivity for detecting DNA delivered to transgenic cells. A replicating vector may also be useful for delivery of genes flanked by DNA sequences from transposable elements such as Ac, Ds, or Mu. It has been proposed (Laufs et al., 1990) that transposition of these elements within the maize genome requires DNA replication. It is also contemplated that transposable elements would be useful for introducing DNA fragments lacking elements necessary for selection and maintenance of the plasmid vector in bacteria, e.g., antibiotic resistance genes and origins of DNA replication. It is also proposed that use of a transposable element such as Ac, Ds, or Mu would actively promote integration of the desired DNA and hence increase the frequency of stably transformed cells. The use of a transposable element such as Ac, Ds, or Mu may actively promote integration of the DNA of interest and hence increase the frequency of stably transformed cells. Transposable elements may be useful to allow separation of genes of interest from elements necessary for selection and maintenance of a plasmid vector in bacteria or selection of a transformant. By use of a transposable element, desirable and undesirable DNA sequences may be transposed apart from each other in the genome, such that through genetic segregation in progeny, one may identify plants with either the desirable or the undesirable DNA sequences.

DNA useful for introduction into plant cells includes that which has been derived or isolated from any source, that may be subsequently characterized as to structure, size and/or function, chemically altered, and later introduced into plants. An example of DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering. Such DNA is commonly referred to as "recombinant DNA."

Therefore useful DNA includes completely synthetic DNA, semi-synthetic DNA, DNA isolated from biological sources, and DNA derived from introduced RNA. Generally, the introduced DNA is not originally resident in the plant genotype which is the recipient of the DNA, but it is within the scope of the invention to isolate a gene from a given plant genotype, and to subsequently introduce multiple copies of the gene into the same genotype, e.g., to enhance production of a given gene product such as a storage protein or a protein that confers tolerance or resistance to water deficit.

The introduced DNA includes but is not limited to, DNA from plant genes, and non-plant genes such as those from bacteria, yeasts, animals or viruses. The introduced DNA can include modified genes, portions of genes, or chimeric genes, including genes from the same or different maize genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of untransformed plant.

The introduced DNA used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the resultant plant. For example, the DNA may itself comprise or consist of a promoter that is active in a plant which is derived from a source other than that plant, or may utilize a promoter already present in a plant genotype that is the transformation target.

Generally, the introduced DNA will be relatively small, i.e., less than about 30 kb to minimize any susceptibility to physical, chemical, or enzymatic degradation which is known to increase as the size of the DNA increases. As noted above, the number of proteins, RNA transcripts or mixtures thereof which is introduced into the plant genome is preferably preselected and defined, e.g., from one to about 5-10 such products of the introduced DNA may be formed.

Two principal methods for the control of expression are known, viz.: overexpression and underexpression. Overexpression can be achieved by insertion of one or more than one extra copy of the selected gene. It is, however, not unknown for plants or their progeny, originally transformed with one or more than one extra copy of a nucleotide sequence, to exhibit the effects of underexpression as well as overexpression. For underexpression there are two principle methods which are commonly referred to in the art as "antisense downregulation" and "sense downregulation" (sense downregulation is also referred to as "cosuppression"). Generically these processes are referred to as "gene silencing". Both of these methods lead to an inhibition of expression of the target gene.

Obtaining sufficient levels of transgene expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed.

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters.

Promoters which are useful for plant transgene expression include those that are inducible, viral, synthetic, constitutive (Odell et al., 1985), temporally regulated, spatially regulated, tissue-specific, and spatio-temporally regulated.

Where expression in specific tissues or organs is desired, tissue-specific promoters may be used. In contrast, where gene expression in response to a stimulus is desired, inducible promoters are the regulatory elements of choice. Where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

A. Transcription Regulatory Sequences

1. Promoters

The choice of promoter will vary depending on the temporal and spatial requirements for expression, and also depending on the target species. In some cases, expression in multiple tissues is desirable. While in others, tissue-specific, e.g., leaf-specific, expression is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

These promoters include, but are not limited to, constitutive, inducible, temporally regulated, developmentally regulated, spatially-regulated, chemically regulated, stress-responsive, tissue-specific, viral and synthetic promoters. Promoter sequences are known to be strong or weak. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. A bacterial promoter such as the $P_{tac}$ promoter can be induced to varying levels of gene expression depending on the level of isothiopropylgalactoside added to the transformed bacterial cells. An isolated promoter sequence that is a strong promoter for heterologous nucleic acid is advantageous because it provides for a sufficient level of gene expression to allow for easy detection and selection of transformed cells and provides for a high level of gene expression when desired.

Within a plant promoter region there are several domains that are necessary for full function of the promoter. The first of these domains lies immediately upstream of the structural gene and forms the "core promoter region" containing consensus sequences, normally 70 base pairs immediately upstream of the gene. The core promoter region contains the characteristic CAAT and TATA boxes plus surrounding sequences, and represents a transcription initiation sequence that defines the transcription start point for the structural gene.

The presence of the core promoter region defines a sequence as being a promoter: if the region is absent, the promoter is non-functional. Furthermore, the core promoter region is insufficient to provide full promoter activity. A series of regulatory sequences upstream of the core constitute the remainder of the promoter. The regulatory sequences determine expression level, the spatial and temporal pattern of expression and, for an important subset of promoters, expression under inductive conditions (regulation by external factors such as light, temperature, chemicals, hormones).

A range of naturally-occurring promoters are known to be operative in plants and have been used to drive the expression of heterologous (both foreign and endogenous) genes in plants: for example, the constitutive 35S cauliflower mosaic virus (CaMV) promoter, the ripening-enhanced tomato polygalacturonase promoter (Bird et al., 1988), the E8 promoter (Diekman & Fischer, 1988) and the fruit specific 2A1 promoter (Pear et al., 1989) and many others, e.g., U2 and U5 snRNA promoters from maize, the promoter from alcohol dehydrogenase, the Z4 promoter from a gene encoding the Z4 22 kD zein protein, the Z10 promoter from a gene encoding a 10 kD zein protein, a Z27 promoter from a gene encoding a 27 kD zein protein, the A20 promoter from the gene encoding a 19 kD-zein protein, inducible promoters, such as the light inducible promoter derived from the pea rbcS gene and the actin promoter from rice, e.g., the actin 2 promoter (WO 00/70067); seed specific promoters, such as the phaseolin promoter from beans, may also be used. The nucleotide sequences of this invention can also be expressed under the regulation of promoters that are chemically regulated. This enables the nucleic acid sequence or encoded polypeptide to be synthesized only when the crop plants are treated with the inducing chemicals. Chemical induction of gene expression is detailed in EP 0 332 104 (to Ciba-Geigy) and U.S. Pat. No. 5,614,395. A preferred promoter for chemical induction is the tobacco PR-1a promoter.

Examples of some constitutive promoters which have been described include the rice actin 1 (Wang et al., 1992; U.S. Pat. No. 5,641,876), CaMV 35S (Odell et al., 1985), CaMV 19S (Lawton et al., 1987), nos, Adh, sucrose synthase; and the ubiquitin promoters.

Examples of tissue specific promoters which have been described include the lectin (Vodkin, 1983; Lindstrom et al., 1990) corn alcohol dehydrogenase 1 (Vogel et al., 1989; Dennis et al., 1984), corn light harvesting complex (Simpson, 1986; Bansal et al., 1992), corn heat shock protein (Odell et al., 1985), pea small subunit RuBP carboxylase (Poulsen et al., 1986), Ti plasmid mannopine synthase (Langridge et al., 1989), Ti plasmid nopaline synthase (Langridge et al., 1989), petunia chalcone isomerase (vanTunen et al., 1988), bean glycine rich protein 1 (Keller et al., 1989), truncated CaMV 35S (Odell et al., 1985), potato patatin (Wenzler et al., 1989), root cell (Yamamoto et al., 1990), maize zein (Reina et al., 1990; Kriz et al., 1987; Wandelt et al., 1989; Langridge et al., 1983; Reina et al., 1990), globulin-1 (Belanger et al., 1991), α-tubulin, cab (Sullivan et al., 1989), PEPCase (Hudspeth & Grula, 1989), R gene complex-associated promoters (Chandler et al., 1989), histone, and chalcone synthase promoters (Franken et al., 1991). Tissue specific enhancers are described in Fromm et al. (1989).

Inducible promoters that have been described include the ABA- and turgor-inducible promoters, the promoter of the auxin-binding protein gene (Schwob et al., 1993), the UDP glucose flavonoid glycosyl-transferase gene promoter (Ralston et al., 1988), the MPI proteinase inhibitor promoter (Cordero et al., 1994), and the glyceraldehyde-3-phosphate dehydrogenase gene promoter (Kohler et al., 1995; Quigley et al., 1989; Martinez et al., 1989).

Several other tissue-specific regulated genes and/or promoters have been reported in plants. These include genes encoding the seed storage proteins (such as napin, cruciferin, beta-conglycinin, and phaseolin) zein or oil body proteins (such as oleosin), or genes involved in fatty acid biosynthesis (including acyl carrier protein, stearoyl-ACP desaturase. And fatty acid desaturases (fad 2-1)), and other genes expressed during embryo development (such as Bce4, see, for example, EP 255378 and Kridl et al., 1991). Particularly useful for seed-specific expression is the pea vicilin promoter (Czako et al., 1992). (See also U.S. Pat. No. 5,625,136, herein incorporated by reference). Other useful promoters for expression in mature leaves are those that are switched on at the onset of senescence, such as the SAG promoter from *Arabidopsis* (Gan et al., 1995).

A class of fruit-specific promoters expressed at or during antithesis through fruit development, at least until the beginning of ripening, is discussed in U.S. Pat. No. 4,943,674. cDNA clones that are preferentially expressed in cotton fiber have been isolated (John et al., 1992). cDNA clones from tomato displaying differential expression during fruit development have been isolated and characterized (Mansson et al., 1985, Slater et al., 1985). The promoter for polygalacturonase gene is active in fruit ripening. The polygalacturonase gene is described in U.S. Pat. No. 4,535,060, U.S. Pat. No. 4,769,061, U.S. Pat. No. 4,801,590, and U.S. Pat. No. 5,107,065, which disclosures are incorporated herein by reference.

Other examples of tissue-specific promoters include those that direct expression in leaf cells following damage to the leaf (for example, from chewing insects), in tubers (for example, patatin gene promoter), and in fiber cells (an example of a developmentally-regulated fiber cell protein is E6 (John et al., 1992). The E6 gene is most active in fiber, although low levels of transcripts are found in leaf, ovule and flower.

The tissue-specificity of some "tissue-specific" promoters may not be absolute and may be tested by one skilled in the art using the diphtheria toxin sequence. One can also achieve tissue-specific expression with "leaky" expression by a combination of different tissue-specific promoters (Beals et al., 1997). Other tissue-specific promoters can be isolated by one skilled in the art (see U.S. Pat. No. 5,589,379). Several inducible promoters ("gene switches") have been reported. Many are described in the review by Gatz (1996) and Gatz (1997). These include tetracycline repressor system, Lac repressor system, copper-inducible systems, salicylate-inducible systems (such as the PR1a system), glucocorticoid—(Aoyama et al., 1997) and ecdysome-inducible systems. Also included are the benzene sulphonamide—(U.S. Pat. No. 5,364,780) and alcohol-(WO 97/06269 and WO 97/06268) inducible systems and glutathione S-transferase promoters. Other studies have focused on genes inducibly regulated in response to environmental stress or stimuli such as increased salinity. Drought, pathogen and wounding. (Graham et al., 1985; Graham et al., 1985, Smith et al., 1986). Accumulation of metallocarboxypeptidase-inhibitor protein has been reported in leaves of wounded potato plants (Graham et al., 1981). Other plant genes have been reported to be induced methyl jasmonate, elicitors, heat-shock, anaerobic stress, or herbicide safeners.

Regulated expression of the chimeric transacting viral replication protein can be further regulated by other genetic strategies. For example, Cre-mediated gene activation as described by Odell et al. 1990. Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the trans-acting replication gene. In this case, the chimeric Cre gene, the chimeric trans-acting replication gene, or both can be under the control of tissue- and developmental-specific or inducible promoters. An alternate genetic strategy is the use of tRNA suppressor gene. For example, the regulated expression of a tRNA suppressor gene can conditionally control expression of a trans-acting replication protein coding sequence containing an appropriate termination codon as described by Ulmasov et al. 1997. Again, either the chimeric tRNA suppressor gene, the chimeric transacting replication gene, or both can be under the control of tissue- and developmental-specific or inducible promoters.

Frequently it is desirable to have continuous or inducible expression of a DNA sequence throughout the cells of an organism in a tissue-independent manner. For example, increased resistance of a plant to infection by soil- and air-borne-pathogens might be accomplished by genetic manipulation of the plant's genome to comprise a continuous promoter operably linked to a heterologous pathogen-resistance gene such that pathogen-resistance proteins are continuously expressed throughout the plant's tissues.

Alternatively, it might be desirable to inhibit expression of a native DNA sequence within a plant's tissues to achieve a desired phenotype. In this case, such inhibition might be accomplished with transformation of the plant to comprise a constitutive, tissue-independent promoter operably linked to an antisense nucleotide sequence, such that constitutive expression of the antisense sequence produces an RNA transcript that interferes with translation of the mRNA of the native DNA sequence.

To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins which are easily measured, including, but not limited to, chloramphenicol acetyl transferase (CAT), beta-glucuronidase (GUS), green fluorescent protein (GFP), beta-galactosidase (beta-GAL), and luciferase.

The construct containing the reporter gene under the control of the promoter is then introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography.

The level of enzyme activity corresponds to the amount of enzyme that was made, which in turn reveals the level of expression from the promoter of interest. This level of expression can be compared to other promoters to determine the relative strength of the promoter under study. In order to be sure that the level of expression is determined by the promoter, rather than by the stability of the mRNA, the level of the reporter mRNA can be measured directly, such as by Northern blot analysis.

Once activity is detected, mutational and/or deletional analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then introduced to cells and their activity determined.

In one embodiment, the promoter may be a gamma zein promoter, an oleosin ole16 promoter, a globulinI promoter, an actin I promoter, an actin cI promoter, a sucrose synthetase promoter, an INOPS promoter, an EXM5 promoter, a globulinI promoter, a b-32, ADPG-pyrophosphorylase promoter, an LtpI promoter, an Ltp2 promoter, an oleosin ole17 promoter, an oleosin ole18 promoter, an actin 2 promoter, a pollen-specific protein promoter, a pollen-specific pectate lyase promoter, an anther-specific protein promoter, an anther-specific gene RTS2 promoter, a pollen-specific gene promoter, a tapeturn-specific gene promoter, tapetum-specific gene RAB24 promoter, a anthranilate synthase alpha subunit promoter, an alpha zein promoter, an anthranilate synthase beta subunit promoter, a dihydrodipicolinate synthase promoter, a ThiI promoter, an alcohol dehydrogenase promoter, a cab binding protein promoter, an H3C4 promoter, a RUBISCO SS starch branching enzyme promoter, an ACCase promoter, an actin3 promoter, an actin7 promoter, a regulatory protein GF14-12 promoter, a ribosomal protein L9 promoter, a cellulose biosynthetic enzyme promoter, an S-adenosyl-L-homocysteine hydrolase promoter, a superoxide dismutase promoter, a C-kinase receptor promoter, a phosphoglycerate mutase promoter, a root-specific RCc3 mRNA promoter, a glucose-6 phosphate isomerase promoter, a pyrophosphate-fructose 6-phosphatelphosphotransferase promoter, an ubiquitin promoter, a beta-ketoacyl-ACP synthase promoter, a 33 kDa photosystem 11 promoter, an oxygen evolving protein promoter, a 69 kDa vacuolar ATPase subunit promoter, a metallothionein-like protein promoter, a glyceraldehyde-3-phosphate dehydrogenase promoter, an ABA- and ripening-inducible-like protein promoter, a phenylalanine ammonia lyase promoter, an adenosine triphosphatase S-adenosyl-L-homocysteine hydrolase promoter, an a-tubulin promoter, a cab promoter, a PEPCase promoter, an R gene promoter, a lectin promoter, a light harvesting complex promoter, a heat shock protein promoter, a chalcone synthase promoter, a zein promoter, a globulin-1 promoter, an ABA promoter, an auxin-binding protein promoter, a UDP glucose flavonoid glycosyl-transferase gene promoter, an NTI promoter, an actin promoter, an opaque 2 promoter, a b70 promoter, an oleosin promoter, a CaMV 35S promoter, a CaMV 19S promoter, a histone promoter, a turgor-inducible promoter, a pea small subunit RuBP carboxylase promoter, a Ti plasmid mannopine synthase promoter, Ti plasmid nopaline synthase promoter, a petunia chalcone isomerase promoter, a bean glycine rich protein I promoter, a CaMV 35S transcript promoter, a potato patatin promoter, or a S-E9 small subunit RuBP carboxylase promoter.

In some embodiments, a promoter has a nucleic acid sequence as set forth in one of SEQ ID NOs: 1-26.

2. Other Regulatory Elements

In addition to promoters, a variety of 5' and 3' transcriptional regulatory sequences are also available for use in the present invention. Transcriptional terminators are responsible for the termination of transcription and correct mRNA polyadenylation. The 3' nontranslated regulatory DNA sequence preferably includes from about 50 to about 1,000, more preferably about 100 to about 1,000, nucleotide base pairs and contains plant transcriptional and translational termination sequences. Appropriate transcriptional terminators and those which are known to function in plants include the CaMV35S terminator, the tmI terminator, the nopaline synthase terminator, the pea rbcS E9 terminator, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. Alternatively, one also could use a gamma coixin, oleosin 3 or other terminator from the genus *Coix*.

Preferred 3' elements include those from the nopaline synthase gene of *Agrobacterium tumefaciens* (Bevan et al., 1983), the terminator for the T7 transcript from the octopine synthase gene of *Agrobacterium tumefaciens*, and the 3' end of the protease inhibitor I or II genes from potato or tomato.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will be most preferred.

Other sequences that have been found to enhance gene expression in transgenic plants include intron sequences (e.g., from Adh1, bronze1, actin1, actin 2 (WO 00/760067), or the sucrose synthase intron) and viral leader sequences (e.g., from TMV, MCMV and AMV). For example, a number of non-translated leader sequences derived from viruses are known to enhance expression. Specifically, leader sequences from Tobacco Mosaic Virus (TMV), Maize Chlorotic Mottle Virus (MCMV), and Alfalfa Mosaic Virus (AMV) have been shown to be effective in enhancing expression (e.g., Gallie et al., 1987; Skuzeski et al., 1990). Other leaders known in the art include but are not limited to: Picornavirus leaders, for example, EMCV leader (Encephalomyocarditis 5 noncoding region) (Elroy-Stein et al., 1989); Potyvirus leaders, for example, TEV leader (Tobacco Etch Virus); MDMV leader (Maize Dwarf Mosaic Virus); Human immunoglobulin heavy-chain binding protein (BiP) leader, (Macejak et al., 1991); Untranslated leader from the coat protein mRNA of alfalfa mosaic virus (AMV RNA 4), (Jobling et al., 1987; Tobacco mosaic virus leader (TMV), (Gallie et al., 1989; and Maize Chlorotic Mottle Virus leader (MCMV) (Lommel et al., 1991. See also, Della-Cioppa et al., 1987.

Regulatory elements such as Adh intron 1 (Callis et al., 1987), sucrose synthase intron (Vasil et al., 1989) or TMV omega element (Gallie, et al., 1989), may further be included where desired.

Examples of enhancers include elements from the CaMV 35S promoter, octopine synthase genes (Ellis et al., 1987), the rice actin I gene, the maize alcohol dehydrogenase gene (Callis et al., 1987), the maize shrunken I gene (Vasil et al., 1989), TMV Omega element (Gallie et al., 1989) and promoters from non-plant eukaryotes (e.g. yeast; Ma et al., 1988).

Vectors for use in accordance with the present invention may be constructed to include the ocs enhancer element. This element was first identified as a 16 bp palindromic enhancer from the octopine synthase (ocs) gene of ultilane (Ellis et al., 1987), and is present in at least 10 other promoters (Bouchez et al., 1989). The use of an enhancer element, such as the ocs element and particularly multiple copies of the element, will act to increase the level of transcription from adjacent promoters when applied in the context of monocot transformation.

Ultimately, the most desirable DNA segments for introduction into for example a monocot genome may be homologous genes or gene families which encode a desired trait (e.g., increased yield per acre) and which are introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the targeting of a gene in a constitutive manner or a root-specific manner. For example, insect resistant genes may be expressed specifically in the whorl and collar/sheath tissues which are targets for the first and second broods, respectively, of ECB. Likewise, genes encoding proteins with particular activity against rootworm may be targeted directly to root tissues.

Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, an alpha-tubulin gene that directs expression in roots and promoters derived from zein storage protein genes which direct expression in endosperm. It is particularly contemplated that one may advantageously use the 16 bp ocs enhancer element from the octopine synthase (ocs) gene (Ellis et al., 1987; Bouchez et al., 1989), especially when present in multiple copies, to achieve enhanced expression in roots.

Tissue specific expression may be functionally accomplished by introducing a constitutively expressed gene (all tissues) in combination with an antisense gene that is expressed only in those tissues where the gene product is not desired. For example, a gene coding for the crystal toxin protein from *B. thuringiensis* (Bt) may be introduced such that it is expressed in all tissues using the 35S promoter from Cauliflower Mosaic Virus. Expression of an antisense transcript of the Bt gene in a maize kernel, using for example a zein promoter, would prevent accumulation of the Bt protein in seed. Hence the protein encoded by the introduced gene would be present in all tissues except the kernel.

Expression of some genes in transgenic plants will be desired only under specified conditions. For example, it is proposed that expression of certain genes that confer resistance to environmental stress factors such as drought will be desired only under actual stress conditions. It is contemplated that expression of such genes throughout a plants development may have detrimental effects. It is known that a large number of genes exist that respond to the environment. For example, expression of some genes such as rbcS, encoding the small subunit of ribulose bisphosphate carboxylase, is regulated by light as mediated through phytochrome. Other genes are induced by secondary stimuli. For example, synthesis of abscisic acid (ABA) is induced by certain environmental factors, including but not limited to water stress. A number of genes have been shown to be induced by ABA (Skriver and Mundy, 1990). It is also anticipated that expression of genes conferring resistance to insect predation would be desired only under conditions of actual insect infestation. Therefore, for some desired traits inducible expression of genes in transgenic plants will be desired.

Expression of a gene in a transgenic plant will be desired only in a certain time period during the development of the plant. Developmental timing is frequently correlated with tissue specific gene expression. For example, expression of zein storage proteins is initiated in the endosperm about 15 days after pollination.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A particular example of such a use concerns the direction of a herbicide resistance gene, such as the EPSPS gene, to a particular organelle such as the chloroplast rather than to the cytoplasm. This is exemplified by the use of the rbcs transit peptide which confers plastid-specific targeting of proteins. In addition, it is proposed that it may be desirable to target certain genes responsible for male sterility to the mitochondria, or to target certain genes for resistance to phytopathogenic organisms to the extracellular spaces, or to target proteins to the vacuole.

By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. Targeting of certain proteins may be desirable in order to enhance the stability of the protein (U.S. Pat. No. 5,545,818).

It may be useful to target DNA itself within a cell. For example, it may be useful to target introduced DNA to the nucleus as this may increase the frequency of transformation. Within the nucleus itself it would be useful to target a gene in order to achieve site specific integration. For example, it would be useful to have an gene introduced through transformation replace an existing gene in the cell.

Other elements include those that can be regulated by endogenous or exogenous agents, e.g., by zinc finger proteins, including naturally occurring zinc finger proteins or chimeric zinc finger proteins (see, e.g., U.S. Pat. No. 5,789, 538, WO 99/48909; WO 99/45132; WO 98/53060; WO 98/53057; WO 98/53058; WO 00/23464; WO 95/19431; and WO 98/54311) or myb-like transcription factors. For example, a chimeric zinc finger protein may include amino acid sequences which bind to a specific DNA sequence (the zinc finger) and amino acid sequences that activate (e.g., GAL 4 sequences) or repress the transcription of the sequences linked to the specific DNA sequence.

3. Preferred Nucleic Acid Molecules of the Invention

The invention relates to an isolated plant, e.g., *Arabidopsis* and rice, nucleic acid molecule, which directs the expression of linked nucleic acid fragment in a plant, e.g., in root or leaf or constitutively, as well as the corresponding open reading frame and encoded product. The nucleic acid molecule, e.g., one which comprises a promoter can be used to overexpress a linked nucleic acid fragment so as to express a product in a constitutive or tissue-specific manner, or to alter the expression of the product, e.g., via the use of antisense vectors or by "knocking out" the expression of at least one genomic copy of the gene.

Preferred sources from which the nucleic acid molecules of the invention can be obtained or isolated include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (Ipomoea batatus), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (Persea ultilane), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, duckweed (Lemna), barley, vegetables, ornamentals, and conifers.

Duckweed (Lemna, see WO 00/07210) includes members of the family Lemnaceae. There are known four genera and 34 species of duckweed as follows: genus Lemna (*L. aequinoctialis, L. disperma, L. ecuadoriensis, L. gibba, L. japonica, L. minor, L. miniscula, L. obscura, L. perpusilli, L. tenera, L. trisulca, L. turionifera, L. valdiviana*); genus Spirodela (*S. intermedia, S. polyrrhiza, S. punctata*); genus Woffia (*Wa. Angusta, Wa. Arrhiza, Wa. Australina, Wa. Borealis, Wa. Brasiliensis, Wa. Columbiana, Wa. Elongata, Wa. Globosa, Wa. Microscopica, Wa. Neglecta*) and genus Wofiella (W1. ultila, W1. ultilane n, W1. gladiata, W1. ultila, W1. lingulata, W1. repunda, W1. rotunda, and W1. neotropica). Any other genera or species of Lemnaceae, if they exist, are also aspects of the present invention. Lemna gibba, Lemna minor, and Lemna miniscula are preferred, with Lemna minor and Lemna miniscula being most preferred. Lemna species can be classified using the taxonomic scheme described by Landolt, Biosystematic Investigation on the Family of Duckweeds: The family of Lemnaceae—A Monograph Study. Geobatanischen Institut ETH, Stiftung Rubel, Zurich (1986)).

Vegetables from which to obtain or isolate the nucleic acid molecules of the invention include, but are not limited to, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals from which to obtain or isolate the nucleic acid molecules of the invention include, but are not limited to, azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga ultilane*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Leguminous plants from which the nucleic acid molecules of the invention can be isolated or obtained include, but are not limited to, beans and peas. Beans include guar, locust bean, fenugreek, soybean, garden beans, cowpea, mungbean, lima bean, fava bean, lentils, chickpea, and the like. Legumes include, but are not limited to, *Arachis*, e.g., peanuts, *Vicia*, e.g., crown vetch, hairy vetch, adzuki bean, mung bean, and chickpea, Lupinus, e.g., lupine, *trifolium, Phaseolus*, e.g., common bean and lima bean, *Pisum*, e.g., field bean, Melilotus, e.g., clover, *Medicago*, e.g., alfalfa, *Lotus*, e.g., trefoil, lens, e.g., lentil, and false indigo. Preferred forage and turf grass from which the nucleic acid molecules of the invention can be isolated or obtained for use in the methods of the invention include, but are not limited to, alfalfa, orchard grass, tall fescue, perennial ryegrass, creeping bent grass, and redtop.

Other preferred sources of the nucleic acid molecules of the invention include *Acacia*, aneth, artichoke, arugula, blackberry, canola, cilantro, clementines, escarole, eucalyptus, fennel, grapefruit, honey dew, jicama, kiwifruit, lemon, lime, mushroom, nut, okra, orange, parsley, persimmon, plantain, pomegranate, poplar, radiata pine, radicchio, Southern pine, sweetgum, tangerine, triticale, vine, yams, apple, pear, quince, cherry, apricot, melon, hemp, buckwheat, grape, raspberry, *chenopodium*, blueberry, nectarine, peach, plum, strawberry, watermelon, eggplant, pepper, cauliflower, *Brassica*, e.g., broccoli, cabbage, ultilan sprouts, onion, carrot, leek, beet, broad bean, celery, radish, pumpkin, endive, gourd, garlic, snapbean, spinach, squash, turnip, ultilane, and zucchini.

Yet other sources of nucleic acid molecules are ornamental plants including, but not limited to, impatiens, Begonia, Pelargonium, Viola, Cyclamen, Verbena, Vinca, Tagetes, Primula, Saint Paulia, Agertum, *Amaranthus, Antihirrhinum, Aquilegia, Cineraria, Clover, Cosmo, Cowpea, Dahlia, Datura, Delphinium, Gerbera, Gladiolus, Gloxinia, Hippeastrum, Mesembryanthemum, Salpiglossos,* and *Zinnia,* and plants such as those shown in Table 1.

TABLE 1

| FAMILY | LATIN NAME | COMMON NAME | MAP REFERENCES RESOURCES |
|---|---|---|---|
| Cucurbitaceae | Cucumis sativus | Cucumber | |
| | Cucumis melo | Melon | |
| | Citrullus lanatus | Watermelon | |
| | Cucurbita pepo | Squash - summer | |
| | Cucurbita maxima | Squash - winter | |
| | Cucurbita moschata | Pumpkin/butternut | |
| Solanaceae | Lycopersicon esculentum | Tomato | 15x BAC on variety Heinz 1706 order from Clemson Genome center 11.6x BAC of L. cheesmanii (originates from J. Giovannoni) available from Clemson genome center EST collection from TIGR EST collection from Clemsom Genome Center TAG 99: 254-271, 1999 (esculentum x pennelli) TAG 89: 1007-1013, 1994 (eruvianum) Plant Cell Reports 12: 293-297, 1993 (RAPDs) Genetics 132: 1141-1160, 1992 (potato x tomato) Genetics 120: 1095-1105, 1988 (RFLP potato and tomato) Genetics 115: 387-393, 1986 (esculentum x pennelli isozyme and cDNAs) |
| | Capsicum annuum | Pepper | |
| | Capsicum frutescens | Chile pepper | |
| | Solanum melongena | Eggplant | |
| | (Nicotiana tabacum) | (Tobacco) | |
| | (Solanum tuberosum) | (Potato) | |
| | (Petunia x hybrida hort. Ex E. Vilm.) | (Petunia) | 4x BAC of Petunia hybrida 7984 available from Clemson genome center |
| Brassicaceae | Brassica oleracea L. var. italica | Broccoli | |
| | Brassica oleracea L. var. capitata | Cabbage | |
| | Brassica rapa | Chinese Cabbage | |
| | Brassica oleracea L. var. botrytis | Cauliflower | |
| | Raphanus sativus var. niger | Daikon | |
| | (Brassica napus) | (Oilseed rape) | |
| | Arabidopsis | | 12x and 6x BACs on Columbia strain available from Clemson genome center |
| Umbelliferae | Daucus carota | Carrot | |
| Compositae | Lactuca sativa | Lettuce | |
| | Helianthus annuus | (Sunflower) | |
| Chenopodiaceae | Spinacia oleracea | Spinach | |
| | (Beta vulgaris) | (Sugar Beet) | |
| Leguminosae | Phaseolus vulgaris | Bean | 4.3x BAC available from Clemson genome center |
| | Pisum sativum | Pea | |
| | (Glycine max) | (Soybean) | 7.5x and 7.9x BACs available from Clemson genome center |
| Gramineae | Zea mays | Sweet Corn | Novartis BACs for Mo17 and B73 have been donated to Clemson Genome Center |
| | (Zea mays) | (Field Corn) | |
| Liliaceae | Allium cepa | Onion Leek (Garlic) (Asparagus) | |

Preferred forage and turf grass nucleic acid sources for the nucleic acid molecules of the invention include, but are not limited to, alfalfa, orchard grass, tall fescue, perennial ryegrass, creeping bent grass, and redtop. Yet other preferred sources include, but are not limited to, crop plants and in particular cereals (for example, corn, alfalfa, sunflower, rice, Brassica, canola, soybean, barley, soybean, sugarbeet, cotton, safflower, peanut, sorghum, wheat, millet, tobacco, and the like), and even more preferably corn, rice and soybean.

Based on the Arabidopsis nucleic acid sequence of the present invention, orthologs may be identified or isolated from the genome of any desired organism, preferably from another plant, according to well known techniques based on their sequence similarity to the Arabidopsis nucleic acid sequences, e.g., hybridization, PCR or computer generated sequence comparisons. For example, all or a portion of a particular Arabidopsis nucleic acid sequence is used as a probe that selectively hybridizes to other gene sequences present in a population of cloned genomic DNA fragments or cDNA fragments (i.e., genomic or cDNA libraries) from a chosen source organism. Further, suitable genomic and cDNA libraries may be prepared from any cell or tissue of an organism. Such techniques include hybridization screening of plated DNA libraries (either plaques or colonies; see, e.g., Sambrook et al., 1989) and amplification by PCR using oligonucleotide primers preferably corresponding to sequence domains conserved among related polypeptide or subsequences of the nucleotide sequences provided herein (see, e.g., Innis et al., 1990). These methods are particularly well suited to the isolation of gene sequences from organisms closely related to the organism from which the probe sequence is derived. The application of these methods using the Arabidopsis sequences as probes is well suited for the isolation of gene sequences from any source organism, preferably other plant species. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the sequence of the invention. Methods for preparation of probes for hybridization and for construction of cDNA and genomic libraries are generally known in the art and are disclosed in Sambrook et al. (1989). In general, sequences that hybridize to the sequences disclosed herein will have at least 40% to 50%, about 60% to 70% and even about 80% 85%, 90%, 95% to 98% or more identity with the disclosed sequences. That is, the sequence similarity of sequences may range, sharing at least about 40% to 50%, about 60% to 70%, and even about 80%, 85%, 90%, 95% to 98% sequence similarity.

The nucleic acid molecules of the invention can also be identified by, for example, a search of known databases for genes encoding polypeptides having a specified amino acid sequence identity or DNA having a specified nucleotide sequence identity. Methods of alignment of sequences for comparison are well known in the art and are described herein.

For example, to identify orthologs of the sequences described herein, similarity searches were carried out in databases using a BLAST (see above) algorithm followed by analysis using SCAN (the Sequence Comparison Analysis, program version 1.0 k licensed from the Los Almos National Laboratories) software with added filters.

4. Methods for Mutagenizing Regulatory Elements

It is specifically contemplated by the inventors that one could mutagenize a promoter to, for example, potentially improve the utility of the elements for the expression of transgenes in plants. The mutagenesis of these elements can be carried out at random and the mutagenized promoter sequences screened for activity in a trial-by-error procedure.

Alternatively, particular sequences which provide the promoter with desirable expression characteristics, or the promoter with expression enhancement activity, could be identified and these or similar sequences introduced into the sequences via mutation. It is further contemplated that one could mutagenize these sequences in order to enhance their expression of transgenes in a particular species.

The means for mutagenizing a DNA segment encoding a promoter sequence of the current invention are well-known to those of skill in the art. As indicated, modifications to promoter or other regulatory element may be made by random, or site-specific mutagenesis procedures. The promoter and other regulatory element may be modified by altering their structure through the addition or deletion of one or more nucleotides from the sequence which encodes the corresponding unmodified sequences.

Mutagenesis may be performed in accordance with any of the techniques known in the art, such as, and not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art.

Double stranded plasmids also are routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the promoter. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation.

This heteroduplex vector is then used to transform or transfect appropriate cells, such as E. coli cells, and cells are selected which include recombinant vectors bearing the mutated sequence arrangement. Vector DNA can then be isolated from these cells and used for plant transformation. A genetic selection scheme was devised by Kunkel et al. (1987) to enrich for clones incorporating mutagenic oligonucleotides. Alternatively, the use of PCR with commercially available thermostable enzymes such as Taq polymerase may be used to incorporate a mutagenic oligonucleotide primer into an amplified DNA fragment that can then be cloned into an appropriate cloning or expression vector. The PCR-mediated mutagenesis procedures of Tomic et al. (1990) and Upender et al. (1995) provide two examples of such protocols. A PCR employing a thermostable ligase in addition to a thermostable polymerase also may be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected promoter-encoding DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

In addition, an unmodified or modified nucleotide sequence of the present invention can be varied by shuffling the sequence of the invention. To test for a function of variant DNA sequences according to the invention, the sequence of interest is operably linked to a selectable or screenable marker gene and expression of the marker gene is tested in transient expression assays with protoplasts or in stably transformed plants. It is known to the skilled artisan that DNA sequences capable of driving expression of an associated nucleotide sequence are build in a modular way. Accordingly, expression levels from shorter DNA fragments may be different than the one from the longest fragment and may be different from each other. For example, deletion of a down-regulating upstream element will lead to an increase in the expression levels of the associated nucleotide sequence while deletion of an up-regulating element will decrease the expression levels of the associated nucleotide sequence. It is also known to the skilled artisan that deletion of development-specific or a tissue-specific element will lead to a temporally or spatially altered expression profile of the associated nucleotide sequence.

Embraced by the present invention are also functional equivalents of the promoters of the present invention, i.e. nucleotide sequences that hybridize under stringent conditions to the reverse-complement of any one of SEQ ID NOs: 1-26, or the promoter orthologs thereof.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson and Rarnstad, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224. A number of template dependent processes are available to amplify the target sequences of interest present in a sample, such methods being well known in the art and specifically disclosed herein below.

Where a clone comprising a promoter has been isolated in accordance with the instant invention, one may wish to delimit the essential promoter regions within the clone. One efficient, targeted means for preparing mutagenizing promoters relies upon the identification of putative regulatory elements within the promoter sequence. This can be initiated by comparison with promoter sequences known to be expressed in similar tissue-specific or developmentally unique manner. Sequences which are shared among promoters with similar expression patterns are likely candidates for the binding of transcription factors and are thus likely elements which confer expression patterns. Confirmation of these putative regulatory elements can be achieved by deletion analysis of each putative regulatory region followed by functional analysis of each deletion construct by assay of a reporter gene which is functionally attached to each construct. As such, once a starting promoter sequence is provided, any of a number of different deletion mutants of the starting promoter could be readily prepared.

As indicated above, deletion mutants, deletion mutants of the promoter of the invention also could be randomly prepared and then assayed. With this strategy, a series of constructs are prepared, each containing a different portion of the clone (a subclone), and these constructs are then screened for activity. A suitable means for screening for activity is to attach a deleted promoter or intron construct which contains a deleted segment to a selectable or screenable marker, and to isolate only those cells expressing the marker gene. In this way, a number of different, deleted promoter constructs are identified which still retain the desired, or even enhanced, activity. The smallest segment which is required for activity is thereby identified through comparison of the selected constructs. This segment may then be used for the construction of vectors for the expression of exogenous genes.

B. Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait, the green fluorescent protein (GFP)). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., alpha-amylase, beta-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). For example, the maize HPRG (Steifel et al., 1990) molecule is well characterized in terms of molecular biology, expression and protein structure. However, any one of a variety of ultilane and/or glycine-rich wall proteins (Keller et al., 1989) could be modified by the addition of an antigenic site to create a screenable marker.

One exemplary embodiment of a secretable screenable marker concerns the use of a maize sequence encoding the wall protein HPRG, modified to include a 15 residue epitope from the pro-region of murine interleukin, however, virtually any detectable epitope may be employed in such embodiments, as selected from the extremely wide variety of antigen-antibody combinations known to those of skill in the art. The unique extracellular epitope can then be straightforwardly detected using antibody labeling in conjunction with chromogenic or fluorescent adjuncts.

Elements of the present disclosure may be exemplified in detail through the use of the bar and/or GUS genes, and also through the use of various other markers. Of course, in light of this disclosure, numerous other possible selectable and/or screenable marker genes will be apparent to those of skill in the art in addition to the one set forth hereinbelow. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant.

1. Selectable Markers

Possible selectable markers for use in connection with the present invention include, but are not limited to, a neo gene (Potrykus et al., 1985) which codes for kanamycin resistance and can be selected for using kanamycin, G418, paromomycin, and the like; a bar gene which codes for bialaphos or phosphinothricin resistance; a gene which encodes an altered EPSP synthase protein (Hinchee et al., 1988) thus conferring glyphosate resistance; a nitrilase gene such as bxn from *Klebsiella ozaenae* which confers resistance to bromoxynil (Stalker et al., 1988); a mutant acetolactate synthase gene (ALS) which confers resistance to imidazolinone, sulfonylurea or other ALS-inhibiting chemicals (European Patent Application 154,204, 1985); a methotrexate-resistant DHFR gene (Thillet et al., 1988); a dalapon dehalogenase gene that confers resistance to the herbicide dalapon; a mutated anthranilate synthase gene that confers resistance to 5-methyl tryptophan. Preferred selectable marker genes encode phosphinothricin acetyltransferase; glyphosate resistant EPSPS, aminoglycoside phosphotransferase; hygromycin phosphotransferase, or neomycin phosphotransferase. Where a mutant EPSP synthase gene is employed, additional benefit may be realized through the incorporation of a suitable chloroplast transit peptide, CTP (European Patent Application 0,218,571, 1987).

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces* viridochromogenes. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death. The success in using this selective system in conjunction with monocots was particularly surprising because of the major difficulties which have been reported in transformation of cereals (Potrykus, 1989).

Where one desires to employ a bialaphos resistance gene in the practice of the invention, a particularly useful gene for this purpose is the bar or pat genes obtainable from species of *Streptomyces* (e.g., ATCC No. 21,705). The cloning of the bar gene has been described (Murakami et al., 1986; Thompson et al., 1987) as has the use of the bar gene in the context of plants other than monocots (De Block et al., 1987; De Block et al., 1989).

Selection markers resulting in positive selection, such as a phosphomannose isomerase gene, as described in patent application WO 93/05163, may also be used. Alternative genes to be used for positive selection are described in WO 94/20627 and encode xyloisomerases and phosphomannoisomerases such as mannose-6-phosphate isomerase and mannose-1-phosphate isomerase; phosphomanno mutase; mannose epimerases such as those which convert carbohydrates to mannose or mannose to carbohydrates such as glucose or galactose; phosphatases such as mannose or xylose phosphatase, mannose-6-phosphatase and mannose-1-phosphatase, and permeases which are involved in the transport of mannose, or a derivative, or a precursor thereof into the cell. Transformed cells are identified without damaging or killing the non-transformed cells in the population and without co-introduction of antibiotic or herbicide resistance genes. As described in WO 93/05163, in addition to the fact that the need for antibiotic or herbicide resistance genes is eliminated, it has been shown that the positive selection method is often far more efficient than traditional negative selection.

2. Screenable Markers

Screenable markers that may be employed include, but are not limited to, a beta-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a beta-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (lkuta et al., 1990); a tyrosinase gene (Katz et al., 1983) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995).

Genes from the maize R gene complex are contemplated to be particularly useful as screenable markers. The R gene complex in maize encodes a protein that acts to regulate the production of anthocyanin pigments in most seed and plant tissue. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe et al., 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening. Where use of a screenable marker gene such as lux or GFP is desired, benefit may be realized by creating a gene fusion between the screenable marker gene and a selectable marker gene, for example, a GFP—NPTII gene fusion. This could allow, for example, selection of transformed cells followed by screening of transgenic plants or seeds.

C. Exogenous Genes for Modification of Plant Phenotypes

Genes of interest are reflective of the commercial markets and interests of those involved in the development of the crop. Crops and markets of interest changes, and as developing nations open up world markets, new crops and technologies will also emerge. In addition, as the understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in starch, oil, carbohydrate, or nutrient metabolism, as well as those affecting kernel size, sucrose loading, zinc finger proteins, see, e.g., U.S. Pat. No. 5,789,538, WO 99/48909; WO 99/45132; WO 98/53060; WO 98/53057; WO 98/53058; WO 00/23464; WO 95/19431; and WO 98/54311, and the like.

One skilled in the art recognizes that the expression level and regulation of a transgene in a plant can vary significantly from line to line. Thus, one has to test several lines to find one with the desired expression level and regulation. Once a line is identified with the desired regulation specificity of a chimeric Cre transgene, it can be crossed with lines carrying different inactive replicons or inactive transgene for activation.

Other sequences which may be linked to the gene of interest which encodes a polypeptide are those which can target to a specific organelle, e.g., to the mitochondria, nucleus, or plastid, within the plant cell. Targeting can be achieved by providing the polypeptide with an appropriate targeting peptide sequence, such as a secretory signal peptide (for secretion or cell wall or membrane targeting, a plastid transit peptide, a chloroplast transit peptide, e.g., the chlorophyll a/b binding protein, a mitochondrial target peptide, a vacuole targeting peptide, or a nuclear targeting peptide, and the like. For example, the small subunit of ribulose bisphosphate carboxylase transit peptide, the EPSPS transit peptide or the dihydrodipicolinic acid synthase transit peptide may be used. For examples of plastid organelle targeting sequences (see WO 00/12732). Plastids are a class of plant organelles derived from proplastids and include chloroplasts, leucoplasts, aravloplasts, and chromoplasts. The plastids are major sites of biosynthesis in plants. In addition to photosynthesis in the chloroplast, plastids are also sites of lipid biosynthesis, nitrate reduction to ammonium, and starch storage. And while plastids contain their own circular genome, most of the proteins localized to the plastids are encoded by the nuclear genome and are imported into the organelle from the cytoplasm.

Transgenes used with the present invention will often be genes that direct the expression of a particular protein or polypeptide product, but they may also be non-expressible DNA segments, e.g., transposons such as Ds that do no direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch properties; oil quantity and quality; and the like. One may desire to incorporate one or more genes conferring any such desirable trait or traits, such as, for example, a gene or genes encoding pathogen resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

1. Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate). However, genes are known that encode glyphosate-resistant EPSP Synthase enzymes.

These genes are particularly contemplated for use in monocot transformation. The deh gene encodes the enzyme dalapon dehalogenase and confers resistance to the herbicide dalapon. The bxn gene codes for a specific nitrilase enzyme that converts bromoxynil to a non-herbicidal degradation product.

2. Insect Resistance

An important aspect of the present invention concerns the introduction of insect resistance-conferring genes into plants. Potential insect resistance genes which can be introduced include *Bacillus thuringiensis* crystal toxin genes or Bt genes (Watrud et al., 1985). Bt genes may provide resistance to lepidopteran or coleopteran pests such as European Corn Borer (ECB) and corn rootworm (CRW). Preferred Bt toxin genes for use in such embodiments include the CryIA(b) and CryIA(c) genes. Endotoxin genes from other species of *B. thuringiensis* which affect insect growth or development may also be employed in this regard.

The poor expression of Bt toxin genes in plants is a well-documented phenomenon, and the use of different promoters, fusion proteins, and leader sequences has not led to significant increases in Bt protein expression (Vaeck et al., 1989; Barton et al., 1987). It is therefore contemplated that the most advantageous Bt genes for use in the transformation protocols disclosed herein will be those in which the coding sequence has been modified to effect increased expression in plants, and more particularly, those in which maize preferred codons have been used. Examples of such modified Bt toxin genes include the variant Bt CryIA(b) gene termed lab6 (Perlak et al., 1991) and the synthetic CryIA(c) genes termed 1800a and 1800b.

Protease inhibitors may also provide insect resistance (Johnson et al., 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered by the present inventors to produce synergistic insecticidal activity. Other genes which encode inhibitors of the insects' digestive system, or those that encode enzymes or co-factors that facilitate the production of inhibitors, may also be useful. This group may be exemplified by oryzacystatin and amylase inhibitors, such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock et al., 1990; Czapla and Lang, 1990). Lectin genes contemplated to be useful include, for example, barley and wheat germ agglutinin (WGA) and rice lectins (Gatehouse et al., 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, may also result in insecticidal activity, or perhaps cause cessation of metamorphosis (Hammock et al., 1990).

Transgenic plants expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

The present invention also provides methods and compositions by which to achieve qualitative or quantitative changes in plant secondary metabolites. One example concerns transforming plants to produce DIMBOA which, it is contemplated, will confer resistance to European corn borer, rootworm and several other maize insect pests. Candidate genes that are particularly considered for use in this regard include those genes at the bx locus known to be involved in the synthetic DIMBOA pathway (Dunn et al., 1981). The introduction of genes that can regulate the production of maysin, and genes involved in the production of dhurrin in sorghum, is also contemplated to be of use in facilitating resistance to earworm and rootworm, respectively.

*Tripsacum* dactyloides is a species of grass that is resistant to certain insects, including corn root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson and Guss, 1972).

Further genes encoding proteins characterized as having potential insecticidal activity may also be used as transgenes in accordance herewith. Such genes include, for example, the cowpea trypsin inhibitor (CpTI; Hilder et al., 1987) which may be used as a rootworm deterrent; genes encoding avermectin (Campbell, 1989; Ikeda et al., 1987) which may prove particularly useful as a corn rootworm deterrent; ribosome inactivating protein genes; and even genes that regulate plant structures. Transgenic maize including anti-insect antibody genes and genes that code for enzymes that can covert a non-toxic insecticide (pro-insecticide) applied to the outside of the plant into an insecticide inside the plant are also contemplated.

3. Environment or Stress Resistance

Improvement of a plant's ability to tolerate various environmental stresses such as, but not limited to, drought, excess moisture, chilling, freezing, high temperature, salt, and oxidative stress, can also be effected through expression of heterologous, or overexpression of homologous genes. Benefits may be realized in terms of increased resistance to freezing temperatures through the introduction of an "antifreeze" protein such as that of the Winter Flounder (Cutler et al., 1989) or synthetic gene derivatives thereof. Improved chilling tolerance may also be conferred through increased expression of glycerol-3-phosphate acetyltransferase in chloroplasts (Murata et al., 1992; Wolter et al., 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., 1992). Such strategies may allow for tolerance to freezing in newly emerged fields as well as extending later maturity higher yielding varieties to earlier relative maturity zones.

Expression of novel genes that favorably effect plant water content, total water potential, osmotic potential, and turgor can enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of a gene encoding the biosynthesis of osmotically-active solutes can impart protection against drought. Within this class of genes are DNAs encoding mannitol dehydrogenase (Lee and Saier, 1982) and trehalose-6-phosphate synthase (Kaasen et al., 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., cited supra (1992), 1993).

Similarly, the efficacy of other metabolites in protecting either enzyme function (e.g. alanopine or propionic acid) or membrane integrity (e.g., alanopine) has been documented (Loomis et al., 1989), and therefore expression of gene encoding the biosynthesis of these compounds can confer drought resistance in a manner similar to or complimentary to mannitol. Other examples of naturally occurring metabolites that are osmotically active and/or provide some direct protective effect during drought and/or desiccation include sugars and sugar derivatives such as fructose, erythritol (Coxson et al., 1992), sorbitol, dulcitol (Karsten et al., 1992), glucosylglycerol (Reed et al., 1984; Erdmann et al., 1992), sucrose, stachyose (Koster and Leopold, 1988; Blackman et al., 1992), ononitol and pinitol (Vernon and Bohnert, 1992), and raffinose (Bernal-Lugo and Leopold, 1992). Other osmotically active solutes which are not sugars include, but are not limited to, proline and glycine-betaine (Wyn-Jones and Storey, 1981). Continued canopy growth and increased reproductive fitness during times of stress can be augmented by introduction and expression of genes such as those controlling the osmotically active compounds discussed above and other such compounds, as represented in one exemplary embodiment by the enzyme myoinositol O-methyltransferase.

It is contemplated that the expression of specific proteins may also increase drought tolerance. Three classes of Late Embryogenic Proteins have been assigned based on structural similarities (see Dure et al., 1989). All three classes of these proteins have been demonstrated in maturing (i.e., desiccating) seeds. Within these 3 types of proteins, the Type-II (dehydrin-type) have generally been implicated in drought and/or desiccation tolerance in vegetative plant parts (i.e. Mundy and Chua, 1988; Piatkowski et al., 1990; Yamaguchi-Shinozaki et al., 1992). Recently, expression of a Type-III LEA (HVA-1) in tobacco was found to influence plant height, maturity and drought tolerance (Fitzpatrick, 1993). Expression of structural genes from all three groups may therefore confer drought tolerance. Other types of proteins induced during water stress include thiol proteases, aldolases and transmembrane transporters (Guerrero et al., 1990), which may confer various protective and/or repair-type functions during drought stress. The expression of a gene that effects lipid biosynthesis and hence membrane composition can also be useful in conferring drought resistance on the plant.

Many genes that improve drought resistance have complementary modes of action. Thus, combinations of these genes might have additive and/or synergistic effects in improving drought resistance in plants. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al. 1990 and Shagan et al., 1993). Spatial and temporal expression patterns of these genes may enable maize to better withstand stress.

Expression of genes that are involved with specific morphological traits that allow for increased water extractions from drying soil would be of benefit. For example, introduction and expression of genes that alter root characteristics may enhance water uptake. Expression of genes that enhance reproductive fitness during times of stress would be of significant value. For example, expression of DNAs that improve the synchrony of pollen shed and receptiveness of the female flower parts, i.e., silks, would be of benefit. In addition, expression of genes that minimize kernel abortion during times of stress would increase the amount of grain to be harvested and hence be of value. Regulation of cytokinin levels in monocots, such as maize, by introduction and expression of an isopentenyl transferase gene with appropriate regulatory sequences can improve monocot stress resistance and yield (Gan et al., Science, 270:1986 (1995)).

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

4. Disease Resistance

It is proposed that increased resistance to diseases may be realized through introduction of genes into plants period. It is possible to produce resistance to diseases caused by viruses, bacteria, fungi, root pathogens, insects and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo et al., 1988, Hemenway et al., 1988, Abel et al., 1986). It is contemplated that expression of antisense genes targeted at essential viral functions may impart resistance to said virus. For example, an antisense gene targeted at the gene responsible for replication of viral nucleic acid may inhibit said replication and lead to resistance to the virus. It is believed that interference with other viral functions through the use of antisense genes may also increase resistance to viruses. Further it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in plants may be useful in conferring resistance to bacterial disease. These genes are induced following pathogen attack on a host plant and have been divided into at least five classes of proteins (Bol et al., 1990). Included amongst the PR proteins are beta-1,3-glucanases, chitinases, and osmotin and other proteins that are believed to function in plant resistance to disease organisms. Other genes have been identified that have antifungal properties, e.g., UDA (stinging nettle lectin) and hevein (Broakgert et al., 1989; Barkai-Golan et al., 1978). It is known that certain plant diseases are caused by the production of phytotoxins. Resistance to these diseases could be achieved through expression of a novel gene that encodes an enzyme capable of degrading or otherwise inactivating the phytotoxin. Expression novel genes that alter the interactions between the host plant and pathogen may be useful in reducing the ability the disease organism to invade the tissues of the host plant, e.g., an increase in the waxiness of the leaf cuticle or other morphological characteristics.

Plant parasitic nematodes are a cause of disease in many plants. It is proposed that it would be possible to make the plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins.

5. Mycotoxin Reduction/Elimination

Production of mycotoxins, including aflatoxin and fumonisin, by fungi associated with plants is a significant factor in rendering the grain not useful. These fungal organisms do not cause disease symptoms and/or interfere with the growth of the plant, but they produce chemicals (mycotoxins) that are toxic to animals. Inhibition of the growth of these fungi would reduce the synthesis of these toxic substances and, therefore, reduce grain losses due to mycotoxin contamination. Novel genes may be introduced into plants that would inhibit synthesis of the mycotoxin without interfering with fungal growth. Expression of a novel gene which encodes an enzyme capable of rendering the mycotoxin nontoxic would be useful in order to achieve reduced mycotoxin contamination of grain. The result of any of the above mechanisms would be a reduced presence of mycotoxins on grain.

6. Grain Composition or Quality

Genes may be introduced into plants, particularly commercially important cereals such as maize, wheat or rice, to improve the grain for which the cereal is primarily grown. A wide range of novel transgenic plants produced in this manner may be envisioned depending on the particular end use of the grain.

For example, the largest use of maize grain is for feed or food. Introduction of genes that alter the composition of the grain may greatly enhance the feed or food value. The primary components of maize grain are starch, protein, and oil. Each of these primary components of maize grain may be improved by altering its level or composition. Several examples may be mentioned for illustrative purposes but in no way provide an exhaustive list of possibilities.

The protein of many cereal grains is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after the grain is supplemented with other inputs for feed formulations. For example, when the grain is supplemented with soybean meal to meet lysine requirements, methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway which are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyse steps in the catabolic pathways such as the enzyme lysine-ketoglutarate reductase.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. DNA may be introduced that decreases the expression of members of the zein family of storage proteins. This DNA may encode ribozymes or antisense sequences directed to impairing expression of zein proteins or expression of regulators of zein expression such as the opaque-2 gene product. The protein composition of the grain may be modified through the phenomenon of cosuppression, i.e., inhibition of expression of an endogenous gene through the expression of an identical structural gene or gene fragment introduced through transformation (Goring et al., 1991). Additionally, the introduced DNA may encode enzymes which degrade seines. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD zein of maize and a promoter or other regulatory sequence designed to elevate expression of said protein. The coding sequence of said gene may include additional or replacement codons for essential amino acids. Further, a coding sequence obtained from another species, or, a partially or completely synthetic sequence encoding a completely unique peptide sequence designed to enhance the amino acid composition of the seed may be employed.

The introduction of genes that alter the oil content of the grain may be of value. Increases in oil content may result in increases in metabolizable energy content and density of the seeds for uses in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, beta-ketoacyl-ACP synthase, plus other well known fatty acid biosynthetic activities. Other possibilities are genes that encode proteins that do not possess enzymatic activity such as acyl carrier protein. Additional examples include 2-acetyltransferase, oleosin pyruvate dehydrogenase complex, acetyl CoA synthetase, ATP citrate lyase, ADP-glucose pyrophosphorylase and genes of the carnitine-CoA-acetyl-CoA shuttles. It is anticipated that expression of genes related to oil biosynthesis will be targeted to the plastid, using a plastid transit peptide sequence and preferably expressed in the seed embryo. Genes may be introduced that alter the balance of fatty acids present in the oil providing a more healthful or nutritive feedstuff. The introduced DNA may also encode sequences that block expression of enzymes involved in fatty acid biosynthesis, altering the proportions of fatty acids present in the grain such as described below.

Genes may be introduced that enhance the nutritive value of the starch component of the grain, for example by increasing the degree of branching, resulting in improved utilization of the starch in cows by delaying its metabolism.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA which blocks or eliminates steps in pigment production pathways.

Feed or food comprising some cereal grains possesses insufficient quantities of vitamins and must be supplemented to provide adequate nutritive value. Introduction of genes that enhance vitamin biosynthesis in seeds may be envisioned including, for example, vitamins A, E, B.sub.12, choline, and the like. For example, maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase which enhances phytic acid breakdown. These genes would increase levels of available phosphate in the diet, reducing the need for supplementation with mineral phosphate.

Numerous other examples of improvement of cereals for feed and food purposes might be described. The improvements may not even necessarily involve the grain, but may, for example, improve the value of the grain for silage. Introduction of DNA to accomplish this might include sequences that alter lignin production such as those that result in the "brown midrib" phenotype associated with superior feed value for cattle.

In addition to direct improvements in feed or food value, genes may also be introduced which improve the processing of grain and improve the value of the products resulting from the processing. The primary method of processing certain grains such as maize is via wetmilling. Maize may be improved though the expression of novel genes that increase the efficiency and reduce the cost of processing such as by decreasing steeping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, Theological properties, and the like. To accomplish these changes in properties, genes that encode granule-bound or soluble starch synthase activity or branching enzyme activity may be introduced alone or combination. DNA such as antisense constructs may also be used to decrease levels of endogenous activity of these enzymes. The introduced genes or constructs may possess regulatory sequences that time their expression to specific intervals in starch biosynthesis and starch granule development. Furthermore, it may be advisable to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups which provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn and other grains, the value of which may be improved by introduction and expression of genes. The quantity of oil that can be extracted by wetmilling may be elevated by approaches as described for feed and food above. Oil properties may also be altered to improve its performance in the production and use of cooking oil, shortenings, lubricants or other oil-derived products or improvement of its health attributes when used in the food-related applications. Novel fatty acids may also be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids.

Improvements in the other major cereal wetmilling products, gluten meal and gluten feed, may also be achieved by the introduction of genes to obtain novel plants. Representative possibilities include but are not limited to those described above for improvement of food and feed value.

In addition it may further be considered that the plant be used for the production or manufacturing of useful biological compounds that were either not produced at all, or not produced at the same level, in the plant previously. The novel plants producing these compounds are made possible by the introduction and expression of genes by transformation methods. The possibilities include, but are not limited to, any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance gamma-zein synthesis, popcorn with improved popping quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes which affect flavor such as the shrunken gene (encoding sucrose synthase) for sweet corn.

7. Plant Agronomic Characteristics

Two of the factors determining where plants can be grown are the average daily temperature during the growing season and the length of time between frosts. Within the areas where it is possible to grow a particular plant, there are varying limitations on the maximal time it is allowed to grow to maturity and be harvested. The plant to be grown in a particular area is selected for its ability to mature and dry down to harvestable moisture content within the required period of time with maximum possible yield. Therefore, plant of varying maturities are developed for different growing locations. Apart from the need to dry down sufficiently to permit harvest is the desirability of having maximal drying take place in the field to minimize the amount of energy required for additional drying post-harvest. Also the more readily the grain can dry down, the more time there is available for growth and kernel fill. Genes that influence maturity and/or dry down can be identified and introduced into plant lines using transformation techniques to create new varieties adapted to different growing locations or the same growing location but having improved yield to moisture ratio at harvest. Expression of genes that are involved in regulation of plant development may be especially useful, e.g., the liguleless and rough sheath genes that have been identified in plants.

Genes may be introduced into plants that would improve standability and other plant growth characteristics. For example, expression of novel genes which confer stronger stalks, improved root systems, or prevent or reduce ear droppage would be of great value to the corn farmer. Introduction and expression of genes that increase the total amount of photoassimilate available by, for example, increasing light distribution and/or interception would be advantageous. In addition the expression of genes that increase the efficiency of photosynthesis and/or the leaf canopy would further increase gains in productivity. Such approaches would allow for increased plant populations in the field.

Delay of late season vegetative senescence would increase the flow of assimilate into the grain and thus increase yield. Overexpression of genes within plants that are associated with "stay green" or the expression of any gene that delays senescence would achieve be advantageous. For example, a non-yellowing mutant has been identified in *Festuca* pratensis (Davies et al., 1990). Expression of this gene as well as others may prevent premature breakdown of chlorophyll and thus maintain canopy function.

8. Nutrient Utilization

The ability to utilize available nutrients and minerals may be a limiting factor in growth of many plants. It is proposed that it would be possible to alter nutrient uptake, tolerate pH extremes, mobilization through the plant, storage pools, and availability for metabolic activities by the introduction of novel genes. These modifications would allow a plant to more efficiently utilize available nutrients. It is contemplated that an increase in the activity of, for example, an enzyme that is normally present in the plant and involved in nutrient utilization would increase the availability of a nutrient. An example of such an enzyme would be phytase. It is also contemplated that expression of a novel gene may make a nutrient source available that was previously not accessible, e.g., an enzyme that releases a component of nutrient value from a more complex molecule, perhaps a macromolecule.

9. Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani et al, 1990).

For example, a number of mutations were discovered in maize that confer cytoplasmic male sterility. One mutation in particular, referred to as T cytoplasm, also correlates with sensitivity to Southern corn leaf blight. A DNA sequence, designated TURF-13 (Levings, 1990), was identified that correlates with T cytoplasm. It would be possible through the introduction of TURF-13 via transformation to separate male sterility from disease sensitivity. As it is necessary to be able to restore male fertility for breeding purposes and for grain production, it is proposed that genes encoding restoration of male fertility may also be introduced.

10. Negative Selectable Markers

Introduction of genes encoding traits that can be selected against may be useful for eliminating undesirable linked genes. When two or more genes are introduced together by cotransformation, the genes will be linked together on the host chromosome. For example, a gene encoding a Bt gene that confers insect resistance on the plant may be introduced into a plant together with a bar gene that is useful as a selectable marker and confers resistance to the herbicide Ignite® on the plant. However, it may not be desirable to have an insect resistant plant that is also resistant to the herbicide Ignite®. It is proposed that one could also introduce an antisense bar gene that is expressed in those tissues where one does not want expression of the bar gene, e.g., in whole plant parts. Hence, although the bar gene is expressed and is useful as a selectable marker, it is not useful to confer herbicide resistance on the whole plant. The bar antisense gene is a negative selectable marker.

Negative selection is necessary in order to screen a population of transformants for rare homologous recombinants generated through gene targeting. For example, a homologous recombinant may be identified through the inactivation of a gene that was previously expressed in that cell. The antisense gene to neomycin phosphotransferase II (nptII) has been investigated as a negative selectable marker in tobacco (*Nicotiana tabacum*) and *Arabidopsis thaliana* (Xiang and Guerra, 1993). In this example both sense and antisense nptII genes are introduced into a plant through transformation and the resultant plants are sensitive to the antibiotic kanamycin. An introduced gene that integrates into the host cell chromosome at the site of the antisense nptII gene, and inactivates the antisense gene, will make the plant resistant to kanamycin and other aminoglycoside antibiotics. Therefore, rare site specific recombinants may be identified by screening for antibiotic resistance. Similarly, any gene, native to the plant or introduced through transformation, that when inactivated confers resistance to a compound, may be useful as a negative selectable marker.

It is contemplated that negative selectable markers may also be useful in other ways. One application is to construct transgenic lines in which one could select for transposition to unlinked sites. In the process of tagging it is most common for the transposable element to move to a genetically linked site on the same chromosome. A selectable marker for recovery of rare plants in which transposition has occurred to an unlinked locus would be useful. For example, the enzyme cytosine deaminase may be useful for this purpose (Stougaard, 1993). In the presence of this enzyme the compound 5-fluorocytosine is converted to 5-fluoruracil which is toxic to plant and animal cells. If a transposable element is linked to the gene for the enzyme cytosine deaminase, one may select for transposition to unlinked sites by selecting for transposition events in which the resultant plant is now resistant to 5-fluorocytosine. The parental plants and plants containing transpositions to linked sites will remain sensitive to 5-fluorocytosine. Resistance to 5-fluorocytosine is due to loss of the cytosine deaminase gene through genetic segregation of the transposable element and the cytosine deaminase gene. Other genes that encode proteins that render the plant sensitive to a certain compound will also be useful in this context. For example, T-DNA gene 2 from *Agrobacterium tumefaciens* encodes a protein that catalyzes the conversion of alpha-naphthalene acetamide (NAM) to alpha-napthalene acetic acid (NAA) renders plant cells sensitive to high concentrations of NAM (Depicker et al., 1988).

It is also contemplated that negative selectable markers may be useful in the construction of transposon tagging lines. For example, by marking an autonomous transposable element such as Ac, Master Mu, or En/Spn with a negative selectable marker, one could select for transformants in which the autonomous element is not stably integrated into the genome. This would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

11. Non-Protein-Expressing Sequences a. RNA-Expressing

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes.

Genes may be constructed or isolated, which when transcribed, produce antisense RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

Genes may also be constructed or isolated, which when transcribed produce RNA enzymes, or ribozymes, which can act as endoribonucleases and catalyze the cleavage of RNA molecules with selected sequences. The cleavage of selected messenger RNA's can result in the reduced production of their encoded polypeptide products. These genes may be used to prepare novel transgenic plants which possess them. The transgenic plants may possess reduced levels of polypeptides including but not limited to the polypeptides cited above that may be affected by antisense RNA.

It is also possible that genes may be introduced to produce novel transgenic plants which have reduced expression of a native gene product by a mechanism of cosuppression. It has been demonstrated in tobacco, tomato, and petunia (Goring et al, 1991; Smith et al., 1990; Napoli et al., 1990; van der Krol et al., 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

b. Non-RNA-Expressing

For example, DNA elements including those of transposable elements such as Ds, Ac, or Mu, may be inserted into a gene and cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta et al., 1988). Once identified, the entire gene(s) for the particular trait, including control or regulatory regions where desired may be isolated, cloned and manipulated as desired. The utility of DNA elements introduced into an organism for purposed of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element which may be introduced is a matrix attachment region element (MAR), such as the chicken lysozyme A element (Stief et al., 1989), which can be positioned around an expressible gene of interest to effect an increase in overall expression of the gene and diminish position dependant effects upon incorporation into the plant genome (Stief et al., 1989; Phi-Van et al., 1990).

III. Transformed (Transgenic) Plants of the Invention and Methods of Preparation Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and ultilane meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

Thus, the present invention provides a transformed (transgenic) plant cell, in planta or ex planta, including a transformed plastid or other organelle, e.g., nucleus, mitochondria or chloroplast. The present invention may be used for transformation of any plant species, including, but not limited to, cells from corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (Persea ultilane), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, duckweed (Lemna), barley, vegetables, ornamentals, and conifers.

Duckweed (Lemna, see WO 00/07210) includes members of the family Lemnaceae. There are known four genera and 34 species of duckweed as follows: genus Lemna (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus Spirodela (*S. intermedia, S. polyrrhiza, S. punctata*); genus Woffia (*Wa. Angusta, Wa. Arrhiza, Wa. Australina, Wa. Borealis, Wa. Brasiliensis, Wa. Columbiana, Wa. Elongata, Wa. Globosa, Wa. Microscopica, Wa. Neglecta*) and genus Wofiella (W1. ultila, W1. ultilanen, W1. gladiata, W1. ultila, W1. lingulata, W1. repunda, W1. rotunda, and W1. neotropica). Any other genera or species of Lemnaceae, if they exist, are also aspects of the present invention. Lemna gibba, Lemna minor, and Lemna miniscula are preferred, with Lemna minor and Lemna miniscula being most preferred. Lemna species can be classified using the taxonomic scheme described by Landolt, Biosystematic Investigation on the Family of Duckweeds: The family of Lemnaceae—A Monograph Study. Geobatanischen Institut ETH, Stiftung Rubel, Zurich (1986)).

Vegetables within the scope of the invention include tomatoes (*Lycopersicon esculentum*), lettuce (e.g., *Lactuca* sativa), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (Tsuga ultilane); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Leguminous plants include beans and peas. Beans include guar, locust bean, fenugreek, soybean, garden beans, cowpea, mungbean, lima bean, fava bean, lentils, chickpea, etc. Legumes include, but are not limited to, *Arachis*, e.g., peanuts, *Vicia*, e.g., crown vetch, hairy vetch, adzuki bean, mung bean, and chickpea, Lupinus, e.g., lupine, *trifolium, Phaseolus*, e.g., common bean and lima bean, *Pisum*, e.g., field bean, Melilotus, e.g., clover, *Medicago*, e.g., alfalfa, *Lotus*, e.g., trefoil, lens, e.g., lentil, and false indigo. Preferred forage and turf grass for use in the methods of the invention include alfalfa, orchard grass, tall fescue, perennial ryegrass, creeping bent grass, and redtop.

Other plants within the scope of the invention include *Acacia*, aneth, artichoke, arugula, blackberry, canola, cilantro, clementines, escarole, eucalyptus, fennel, grapefruit, honey dew, jicama, kiwifruit, lemon, lime, mushroom, nut, okra, orange, parsley, persimmon, plantain, pomegranate, poplar, radiata pine, radicchio, Southern pine, sweetgum, tangerine, triticale, vine, yams, apple, pear, quince, cherry, apricot, melon, hemp, buckwheat, grape, raspberry, *chenopodium*, blueberry, nectarine, peach, plum, strawberry, watermelon, eggplant, pepper, cauliflower, *Brassica*, e.g., broccoli, cabbage, ultilan sprouts, onion, carrot, leek, beet, broad bean, celery, radish, pumpkin, endive, gourd, garlic, snapbean, spinach, squash, turnip, ultilane, and zucchini.

Ornamental plants within the scope of the invention include impatiens, Begonia, Pelargonium, Viola, Cyclamen, Verbena, Vinca, Tagetes, Primula, Saint Paulia, Agertum, *Amaranthus, Antihirrhinum, Aquilegia, Cineraria, Clover, Cosmo, Cowpea, Dahlia, Datura, Delphinium, Gerbera, Gladiolus, Gloxinia, Hippeastrum, Mesembryanthemum, Salpiglossos*, and *Zinnia. Other plants within the scope of the invention are shown in Table* 1 (above).

Preferably, transgenic plants of the present invention are crop plants and in particular cereals (for example, corn, alfalfa, sunflower, rice, *Brassica*, canola, soybean, barley, soybean, sugarbeet, cotton, safflower, peanut, sorghum, wheat, millet, tobacco, etc.), and even more preferably corn, rice and soybean.

Transformation of plants can be undertaken with a single DNA molecule or multiple DNA molecules (i.e., co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing *A. tumefaciens* or *A. rhizogenes* as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with the expression cassettes of the invention. The general descriptions of plant expression vectors and reporter genes, and *Agrobacterium* and *Agrobacterium*-mediated gene transfer, can be found in Gruber et al. (1993).

Expression vectors containing genomic or synthetic fragments can be introduced into protoplasts or into intact tissues or isolated cells. Preferably expression vectors are introduced into intact tissue. General methods of culturing plant tissues are provided for example by Maki et al., (1993); and by Phillips et al. (1988). Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues, (Lindsey et al., 1993; Auch & Reth et al.).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti et al., 1985: Byrne et al., 1987; Sukhapinda et al., 1987; Park et al., 1985: Hiei et al., 1994). The use of T-DNA to transform plant cells has received extensive study and is amply described (EP 120516; Hoekema, 1985; Knauf, et al., 1983; and An et al., 1985). For introduction into plants, the chimeric genes of the invention can be inserted into binary vectors as described in the examples.

Other transformation methods are available to those skilled in the art, such as direct uptake of foreign DNA constructs (see EP 295959), techniques of electroporation (Fromm et al., 1986) or high velocity ballistic bombardment with metal particles coated with the nucleic acid constructs (Kline et al., 1987, and U.S. Pat. No. 4,945,050). Once transformed, the cells can be regenerated by those skilled in the art. Of particular relevance are the recently described methods to transform foreign genes into commercially important crops, such as rapeseed (De Block et al., 1989), sunflower (Everett et al., 1987), soybean (McCabe et al., 1988; Hinchee et al., 1988; Chee et al., 1989; Christou et al., 1989; EP 301749), rice (Hiei et al., 1994), and corn (Gordon Kamm et al., 1990; Fromm et al., 1990).

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway et al., 1986), electroporation (Riggs et al., 1986), *Agrobacterium*-mediated transformation (Hinchee et al., 1988), direct gene transfer (Paszkowski et al., 1984), and ballistic particle acceleration using devices available from Agracetus, Inc., Madison, Wis. And BioRad, Hercules, Calif. (see, for example, Sanford et al., U.S. Pat. No. 4,945,050; and McCabe et al., 1988). Also see, Weissinger et al., 1988; Sanford et al., 1987 (onion); Christou et al., 1988 (soybean); McCabe et al., 1988 (soybean); Datta et al., 1990 (rice); Klein et al., 1988 (maize); Klein et al., 1988 (maize); Klein et al., 1988 (maize); Fromm et al., 1990 (maize); and Gordon-Kamm et al., 1990 (maize); Svab et al., 1990 (tobacco chloroplast); Koziel et al., 1993 (maize); Shimamoto et al., 1989 (rice); Christou et al., 1991 (rice); European Patent Application EP 0 332 581 (orchardgrass and other Pooideae); Vasil et al., 1993 (wheat); Weeks et al., 1993 (wheat). In one embodiment, the protoplast transformation method for maize is employed (European Patent Application EP 0 292 435, U.S. Pat. No. 5,350,689).

In another embodiment, a nucleotide sequence of the present invention is directly transformed into the plastid genome. Plastid transformation technology is extensively described in U.S. Pat. Nos. 5,451,513, 5,545,817, and 5,545,818, in PCT application no. WO 95/16783, and in McBride et al., 1994. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate orthologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al., 1990; Staub et al., 1992). This resulted in stable homoplasmic transformants at a frequency of approximately one per 100 bombardments of target leaves. The presence of cloning sites between these markers allowed creation of a plastid targeting vector for introduction of foreign genes (Staub et al., 1993). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab et al., 1993). Other selectable markers useful for plastid transformation are known in the art and encompassed within the scope of the invention. Typically, approximately 15-20 cell division cycles following transformation are required to reach a homoplastidic state. Plastid expression, in which genes are inserted by orthologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

*Agrobacterium tumefaciens* cells containing a vector comprising an expression cassette of the present invention, wherein the vector comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous *Agrobacterium* vector systems useful in carrying out the present invention are known.

For example, vectors are available for transformation using *Agrobacterium tumefaciens*. These typically carry at least one T-DNA border sequence and include vectors such as pBIN19 (Bevan, 1984). In one preferred embodiment, the expression cassettes of the present invention may be inserted into either of the binary vectors pCIB200 and pCIB2001 for use with *Agrobacterium*. These vector cassettes for *Agrobacterium*-mediated transformation wear constructed in the following manner. PTJS75kan was created by NarI digestion of pTJS75 (Schmidhauser & Helinski, 1985) allowing excision of the tetracycline-resistance gene, followed by insertion of an AccI fragment from pUC4K carrying an NPTII (Messing & Vierra, 1982; Bevan et al., 1983; McBride et al., 1990). XhoI linkers were ligated to the EcoRV fragment of pCIB7 which contains the left and right T-DNA borders, a plant selectable nos/nptII chimeric gene and the pUC polylinker (Rothstein et al., 1987), and the XhoI-digested fragment was cloned into SalI-digested pTJS75kan to create pCIB200 (see also EP 0 332 104, example 19). PCIB200 contains the following unique polylinker restriction sites: EcoRI, SstI, KpnI, BglII, XbaI, and SalI. The plasmid pCIB2001 is a derivative of pCIB200 which was created by the insertion into the polylinker of additional restriction sites. Unique restriction sites in the polylinker of pCIB2001 are EcoRI, SstI, KpnI, BglII, XbaI, SalI, MluI, AvrII, ApaI, HpaI, and StuI. PCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

An additional vector useful for *Agrobacterium*-mediated transformation is the binary vector pCIB 10, which contains a gene encoding kanamycin resistance for selection in plants, T-DNA right and left border sequences and incorporates sequences from the wide host-range plasmid pRK252 allowing it to replicate in both *E. coli* and *Agrobacterium*. Its construction is described by Rothstein et al., 1987. Various derivatives of pCIB 10 have been constructed which incorporate the gene for hygromycin B phosphotransferase described by Gritz et al., 1983. These derivatives enable selection of transgenic plant cells on hygromycin only (pCIB743), or hygromycin and kanamycin (pCIB715, pCIB717).

Methods using either a form of direct gene transfer or *Agrobacterium*-mediated transfer usually, but not necessarily, are undertaken with a selectable marker which may provide resistance to an antibiotic (e.g., kanamycin, hygromycin or methotrexate) or a herbicide (e.g., phosphinothricin). The choice of selectable marker for plant transformation is not, however, critical to the invention.

For certain plant species, different antibiotic or herbicide selection markers may be preferred. Selection markers used routinely in transformation include the nptII gene which confers resistance to kanamycin and related antibiotics (Messing & Vierra, 1982; Bevan et al., 1983), the bar gene which confers resistance to the herbicide phosphinothricin (White et al., 1990, Spencer et al., 1990), the hph gene which confers resistance to the antibiotic hygromycin (Blochinger & Diggelmann), and the dhfr gene, which confers resistance to methotrexate (Bourouis et al., 1983).

One such vector useful for direct gene transfer techniques in combination with selection by the herbicide Basta (or phosphinothricin) is pC1B3064. This vector is based on the plasmid pCIB246, which comprises the CaMV 35S promoter in operational fusion to the *E. coli* GUS gene and the CaMV 35S transcriptional terminator and is described in the PCT published application WO 93/07278, herein incorporated by reference. One gene useful for conferring resistance to phosphinothricin is the bar gene from *Streptomyces* viridochromogenes (Thompson et al., 1987). This vector is suitable for the cloning of plant expression cassettes containing their own regulatory signals.

An additional transformation vector is pSOG35 which utilizes the *E. coli* gene dihydrofolate reductase (DHFR) as a selectable marker conferring resistance to methotrexate. PCR was used to amplify the 35S promoter (about 800 bp), intron 6 from the maize Adh1 gene (about 550 bp) and 18 bp of the GUS untranslated leader sequence from pSOG10. A 250 bp fragment encoding the *E. coli* dihydrofolate reductase type II gene was also amplified by PCR and these two PCR fragments were assembled with a SacI-Psti fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus check (MCMV) generated the vector pSOG35. pSOG19 and pSOG35 carry the pUC-derived gene for ampicillin resistance and have HindIII, SphI, PstI and EcoRI sites available for the cloning of foreign sequences.

IV. Production and Characterization of Stably Transformed Plants

Transgenic plant cells are then placed in an appropriate selective medium for selection of transgenic cells which are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic, such as kanamycin, G418, bleomycin, hygromycin, chloramphenicol, herbicide, or the like). The particular marker used will allow for selection of transformed cells as compared to cells lacking the DNA which has been introduced. Components of DNA constructs including transcription cassettes of this invention may be prepared from sequences which are native (endogenous) or foreign (exogenous) to the host. By "foreign" it is meant that the sequence is not found in the wild-type host into which the construct is introduced. Heterologous constructs will contain at least one region which is not native to the gene from which the transcription-initiation-region is derived.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant, e.g., for disease or pest resistance.

DNA may be isolated from cell lines or any plant parts to determine the presence of the preselected nucleic acid segment through the use of techniques well known to those skilled in the art. Note that intact sequences will not always be present, presumably due to rearrangement or deletion of sequences in the cell.

The presence of nucleic acid elements introduced through the methods of this invention may be determined by polymerase chain reaction (PCR). Using this technique discreet fragments of nucleic acid are amplified and detected by gel electrophoresis. This type of analysis permits one to determine whether a preselected nucleic acid segment is present in a stable transformant, but does not prove integration of the introduced preselected nucleic acid segment into the host cell genome. In addition, it is not possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced preselected DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced preselected DNA segments in high molecular weight DNA, i.e., confirm that the introduced preselected DNA segment has been integrated into the host cell genome. The technique of Southern hybridization provides information that is obtained using PCR, e.g., the presence of a preselected DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a preselected DNA segment.

Both PCR and Southern hybridization techniques can be used to demonstrate transmission of a preselected DNA segment to progeny. In most instances the characteristic Southern hybridization pattern for a given transformant will segregate in progeny as one or more Mendelian genes (Spencer et al., 1992); Laursen et al., 1994) indicating stable inheritance of the gene. The nonchimeric nature of the callus and the parental transformants ($R_0$) was suggested by germline transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed.

Very frequently the expression of a gene product is determined by evaluating the phenotypic results of its expression. These assays also may take many forms including but not limited to analyzing changes in the chemical composition, morphology, or physiological properties of the plant. Morphological changes may include greater stature or thicker stalks. Most often changes in response of plants or plant parts to imposed treatments are evaluated under carefully controlled conditions termed bioassays.

V. Uses of Transgenic Plants

Once an expression cassette of the invention has been transformed into a particular plant species, it may be propagated in that species or moved into other varieties of the same species, particularly including commercial varieties, using traditional breeding techniques. Particularly preferred plants of the invention include the agronomically important crops listed above. The genetic properties engineered into the transgenic seeds and plants described above are passed on by sexual reproduction and can thus be maintained and propagated in progeny plants. The present invention also relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

Preferably, the expression cassette in the transgenic plant is sexually transmitted. In one preferred embodiment, the coding sequence is sexually transmitted through a complete normal sexual cycle of the $R_0$ plant to the $R_1$ generation. Additionally preferred, the expression cassette is expressed in the cells, tissues, seeds or plant of a transgenic plant in an amount that is different than the amount in the cells, tissues, seeds or plant of a plant which only differs in that the expression cassette is absent.

The transgenic plants produced herein are thus expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed; increased vitamin, amino acid, and antioxidant content; the production of antibodies (passive immunization) and nutriceuticals), or beneficial to the food processor (e.g., improved processing traits). In such uses, the plants are generally grown for the use of their grain in human or animal foods. Additionally, the use of root-specific promoters in transgenic plants can provide beneficial traits that are localized in the consumable (by animals and humans) roots of plants such as carrots, parsnips, and beets. However, other parts of the plants, including stalks, husks, vegetative parts, and the like, may also have utility, including use as part of animal silage or for ornamental purposes. Often, chemical constituents (e.g., oils or starches) of maize and other crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the expression cassette may be transferred, e.g., from maize cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

Thus, the transgenic plants and seeds according to the invention can be used in plant breeding which aims at the development of plants with improved properties conferred by the expression cassette, such as tolerance of drought, disease, or other stresses. The various breeding steps are characterized by well-defined human intervention such as selecting the lines to be crossed, directing pollination of the parental lines, or selecting appropriate descendant plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines which for example increase the effectiveness of conventional methods such as herbicide or pesticide treatment or allow to dispense with said methods due to their modified genetic properties. Alternatively new crops with improved stress tolerance can be obtained which, due to their optimized genetic "equipment", yield harvested product of better quality than products which were not able to tolerate comparable adverse developmental conditions.

VI. A Computer Readable Medium

The invention also provides a computer readable medium having stored thereon a data structure containing nucleic acid sequences having e.g., at least 70% sequence identity to a nucleic acid sequence selected from those listed in SEQ ID Nos: 1-26, as well as complementary, ortholog and variant sequences thereof. Storage and use of nucleic acid sequences on a computer readable medium is well known in the art. (See for example U.S. Pat. Nos. 6,023,659; 5,867,402; 5,795,716) Examples of such medium include, but are not limited to, magnetic tape, optical disk, CD-ROM, random access memory, volatile memory, non-volatile memory and bubble memory. Accordingly, the nucleic acid sequences contained on the computer readable medium may be compared through use of a module that receives the sequence information and compares it to other sequence information. Examples of other sequences to which the nucleic acid sequences of the invention may be compared include those maintained by the National Center for Biotechnology Information (NCBI) and the Swiss Protein Data Bank. A computer is an example of such a module that can read and compare nucleic acid sequence information. Accordingly, the invention also provides the method of comparing a nucleic acid sequence of the invention to another sequence. For example, a sequence of the invention may be submitted to the NCBI for a Blast search as described herein where the sequence is compared to sequence information contained within the NCBI database and a comparison is returned. The invention also provides nucleic acid sequence information in a computer readable medium that allows the encoded polypeptide to be optimized for a desired property. Examples of such properties include, but are not limited to, increased or decreased: thermal stability, chemical stability, hydrophylicity, hydrophobicity, and the like. Methods for the use of computers to model polypeptides and polynucleotides having altered activities are well known in the art and have been reviewed. (Lesyng et al., 1993; Surles et al., 1994; Koehl et al., 1996; Rossi et al., 2001).

The invention will be further described by the following non-limiting examples.

Example 1

---

GENECHIP ® Standard Protocol

Quantitation of Total RNA
    Total RNA from plant tissue is extracted and quantified.
        1. Quantify total RNA using GeneQuant 1$OD_{260}$ = 40 mg RNA/ml; $A_{260}/A_{280}$ = 1.9 to about 2.1
        2. Run gel to check the integrity and purity of the extracted RNA
Synthesis of Double-Stranded cDNA
    Gibco/BRL SuperScript Choice System for cDNA Synthesis (Cat#1B090-019) was employed to prepare cDNAs. T7-$(dT)_{24}$ oligonucleotides were prepared and purified by HPLC. (5'-GGCCAGTGAATTGTAATACGACTCACTATAGGGA GGCGG-$(dT)_{24}$-3'; SEQ ID NO: 27).
    Step 1. Primer Hybridization:
        Incubate at 70° C. for 10 minutes
        Quick spin and put on ice briefly
    Step 2. Temperature Adjustment:
        Incubate at 42° C. for 2 minutes
    Step 3. First Strand Synthesis:
        DEPC-water-1 µl
        RNA (10 µg final)-10 µl
        T7 = $(dT)_{24}$ Primer (100 pmol final)-1 µl pmol
        5 × $1^{st}$ strand cDNA buffer-4 µl
        0.1M DTT (10 mM final)-2 µl
        10 mM dNTP mix (500 µM final)-1 µl
        Superscript II RT 200 U/µl-1 µl
        Total of 20 µl
    Mix well
    Incubate at 42° C. for 1 hour
    Step 4. Second Strand Synthesis:
        Place reactions on ice, quick spin
        DEPC-water-91 µl
        5 × $2^{nd}$ strand cDNA buffer-30 µl
        10 mM dNTP mix (250 mM final)-3 µl
        E. coli DNA ligase (10 U/µl)-1 µl
        E. coli DNA polymerase 1-10 U/µl-4 µl
        RnaseH 2 U/µl-1 µl
        T4 DNA polymerase 5 U/µl-2 µl
        0.5M EDTA (0.5M final)-10 µl
        Total 162 µl
        Mix/spin down/incubate 16° C. for 2 hours
    Step 5. Completing the Reaction:
    Incubate at 16° C. for 5 minutes
Purification of Double Stranded cDNA
    1. Centrifuge PLG (Phase Lock Gel, Eppendorf 5 Prime Inc., pl-188233) at 14,000x, transfer 162 µl of cDNA to PLG
    2. Add 162 µl of Phenol:Chloroform:Isoamyl alcohol (pH 8.0), centrifuge 2 minutes
    3. Transfer the supernatant to a fresh 1.5 ml tube, add
        Glycogen (5 mg/ml)        2 µl
        0.5M $NH_4OAC$ (0.75x Vol)    120 µl
        ETOH (2.5x Vol, −20° C.)    400 µl

| GENECHIP® Standard Protocol |  |
|---|---|
| 4. Mix well and centrifuge at 14,000x for 20 minutes | |
| 5. Remove supernatant, add 0.5 ml 80% EtOH (−20° C.) | |
| 6. Centrifuge for 5 minutes, air dry or by speed vac for 5-10 minutes | |
| 7. Add 44 μl DEPC $H_2O$ | |
| Analyze of quantity and size distribution of cDNA | |
| Run a gel using 1 μl of the double-stranded synthesis product | |
| Synthesis of Biotinylated cRNA | |
| (use Enzo BioArray High Yield RNA Transcript Labeling Kit Cat#900182) | |
| Purified cDNA | 22 μl |
| 10X Hy buffer | 4 μl |
| 10X biotin ribonucleotides | 4 μl |
| 10X DTT | 4 μl |
| 10X Rnase inhibitor mix | 4 μl |
| 20X T7 RNA polymerase | 2 μl |
| Total | 40 μl |
| Centrifuge 5 seconds, and incubate for 4 hours at 37° C. | |
| Gently mix every 30-45 minutes | |
| Purification and Quantification of cRNA | |
| (use Qiagen Rneasy Mini kit Cat# 74103) | |
| cRNA | 40 μl |
| DEPC $H_2O$ | 60 μl |
| RLT buffer | 350 μl mix by vortexing |
| EtOH | 250 μl mix by pipetting |
| Total | 700 μl |
| Wait 1 minute or more for the RNA to stick | |
| Centrifuge at 2000 rpm for 5 minutes | |
| RPE buffer | 500 μl |
| Centrifuge at 10,000 rpm for 1 minute | |
| RPE buffer | 500 μl |
| Centrifuge at 10,000 rpm for 1 minute | |
| Centrifuge at 10,000 rpm for 1 minute to dry the column | |
| DEPC $H_2O$ | 30 μl |
| Wait for 1 minute, then elute cRNA from by centrifugation, 10K 1 minute | |
| DEPC $H_2O$ | 30 μl |
| Repeat previous step | |
| Determine concentration and dilute to 1 μg/μl concentration | |
| Fragmentation of cRNA | |
| cRNA (1 μg/μl) | 15 μl |
| 5X Fragmentation Buffer* | 6 μl |
| DEPC $H_2O$ | 9 μl |
|  | 30 μl |
| *5x Fragmentation Buffer | |
| 1M Tris (pH 8.1) | 4.0 ml |
| MgOAc | 0.64 g |
| KOAC | 0.98 g |
| DEPC $H_2O$ | |
| Total | 20 ml |
| Filter Sterilize | |
| Array Wash and Staining | |
| Stringent Wash Buffer** | |
| Non-Stringent Wash Buffer*** | |
| SAPE Stain**** | |
| Antibody Stain***** | |

**Stringent Buffer: 12x MES 83.3 ml, 5M NaCl 5.2 ml, 10% Tween 1.0 ml, $H_2O$ 910 ml, Filter Sterilize
***Non-Stringent Buffer: 20x SSPE 300 ml, 10% Tween 1.0 ml, $H_2O$ 698 ml, Filter Sterilize, Antifoam 1.0.
****SAPE stain: 2x Stain Buffer 600 μl, BSA 48 μl, SAPE 12 μl, $H_2O$ 540 μl.
*****Antibody Stain: 2x Stain Buffer 300 μl, H.sub.2O 266.4 μl, BSA 24 μl, Goat IgG 6 μl, Biotinylated Ab 3.6 μl
Wash on fluidics station using the appropriate antibody amplification protocol Example 2

Characterization of Gene Expression Profiles During Plant Development Using the GENECHIP®

The Arabidopsis GENECHIP® provides a method to simultaneously scan over 30% of the genome for the expression profile of each gene on chip. By using RNA extracted from different tissue and developmental stages of development, a scan of the entire Arabidopsis plant is achieved. The advantages of a gene chip in such an analysis include a global gene expression analysis, quantitative results, a highly reproducible system, and a higher sensitivity than Northern blot analyses. Moreover, a gene chip with Arabidopsis DNA has a further advantage in that the Arabidopsis genome is well characterized.

Using the recently designed Arabidopsis high density oligonucleotide probe array, a total of 8,100 Arabidopsis thaliana genes were surveyed for temporal and developmental expression profiling. The objective was to identify known and novel genes that are expressed in specific organs (spatial expression) or developmental stages (temporal expression versus constitutive expression). The represented genes included approximately 1,000 known full length cDNAs, a collection of approximately 500 ESTs or full length sequences, 3,500 annotated GENBANK® genomic sequences (the transcripts of which were confirmed by the presence of ESTs in the database) and about 3,700 annotated GENBANK® sequences with a predicted translated open reading frame with 2 or more "hits" with a protein in the protein database having a defined function.

Total RNA was isolated from 9 samples at different developmental stages for to prepare cRNA microanalysis. These samples were analyzed in 9 separate GENECHIP® (see, e.g., U.S. Pat. Nos. 5,445,934, 5,744,305, 5,700,305, 5,700,637, 5,945,334 and EP 619321 and EP 373203) experiments that included RNA from: 1) germinating seed, day 4; 2) root 2 week; 3) root adult: 4) leaf; 5) leaf adult; 6) leaf senescence; 7) stem; 8) immature siliques; and 9) flowers prior to pollen shed. The samples were hybridized to the *Arabidopsis* arrays and analyzed by laser scanning for relative expression level, fold difference, organ and developmental expression. All genes were expressed in at least one of the samples.

Seeds of wild-type plants of *Arabidopsis thaliana*, ecotype Columbia, were sterilized and germinated in soil. Plants were grown in conviron growth chambers with 12 hours of light at 22° C. 12:12 light dark cycle in metromix. Samples from leaves of 2-week, 5-week, 6-week, 8-week, and 11-week old plants, and inflorescences, flowers and siliques of the 6-week and 8-week old plants were collected (Table 2). In addition, 4-day old seedlings and roots from 2-week, 4-week, and 5-week old plants cultured in MS liquid medium were collected. Samples collected from over 30 plants were pooled and homogenized in liquid nitrogen. Total RNA was extracted using Qiagen Rneasy column (Qiagen, Chatsworth, Calif.).

TABLE 2

| germinating seedling | 4 days of development |
| --- | --- |
| germinating seedling | 4 days of development |
| leaf | 2 weeks after planting |
| leaf | 2 weeks after planting |
| leaf | 5 weeks after planting |
| leaf | 6 weeks after planting |
| leaf | 8 weeks after planting |
| leaf | 11 weeks after planting |
| root | 2 weeks after planting |
| root | 2 weeks after planting |
| root | 5 weeks after planting |
| root | 6 weeks after planting |
| flower | 5 weeks after planting |
| flower | 6 weeks after planting |
| siliques | 5 weeks after planting |
| siliques | 6 weeks after planting |
| siliques | 8-11 weeks after planting |
| inflorescence | 6 weeks after planting |
| inflorescence | 5 weeks after planting |

Total RNA (5 µg) from each sample was reverse transcribed using an oligo $dT_{(24)}$ primer containing a 5' T7 RNA polymerase promoter sequence (5'-GGCCAGTGAATT GTAATACGACTCACTATAGGGAGGCGG-$(dT)_{24}$-3'; SEQ ID NO:27) and SuperScript II reverse transcriptase (Life Technologies). Second strand of cDNA was synthesized using DNA polymerase I and DNA ligase. Biotinylated complementary RNAs (cRNAs) were in vitro transcribed by T7 RNA Polymerase (ENZO BioArray High Yield RNA Transcript Labeling Kit, Enzo). cRNAs were purified using an affinity resin (Qiagen Rneasy Spin Columns) and randomly fragmented by incubating at 94° C. for 35 minutes in a buffer containing 40 mM Tris-acetate, pH 8.1, 100 mM potassium acetate, and 30 mM magnesium acetate to produce molecules of approximately 35 to 200 bases.

The labeled samples were denatured at 99° C. for 5 minutes, equilibrated at 45° C. for 5 minutes, and hybridized to the *Arabidopsis* GENECHIP® genome array (Affymetrix) at 45° C. for 16 hours on a rotisserie at 60 rpm. The hybridized arrays were then rinsed with 1.times.STT and stained with streptavidin phycoerythrin at 25° C. for 10 minutes twice with a rinse in between. After staining, arrays were washed with 1×STT at 25° C. for 20 minutes and stained with biotinylated anti-streptavidin antibody at 25° C. for 10 minutes. The probe array was stained with SAPE at 25° C. for 10 minutes and washed with wash buffer A at 30° C. for 30 minutes. All of the wash and stain procedures were completed using a fluidic station (Affymetrix). The probe array was scanned twice and the intensities were averaged with a Hewlett-Packard Gene-Array Scanner.

Genechip Suite 3.2 (Affymetrix) was used for data normalization. The overall intensity of all probe sets of each chip was scaled to 100 so that the hybridization intensity of all arrays was equivalent. False positives are defined based on experiments in which samples are split, hybridized to GENECHIP® expression arrays and the results compared. A false positive is indicated if a probe set is scored qualitatively as an "Increase" or "Decrease" and quantitatively as changing by at least 2-fold and the average difference is greater than 25. A significant change is defined as 2-fold change or above with an expression baseline of 25, which is determined as the threshold level according to the scaling. For example, the data from each chip was loaded into GeneSpring software and analyzed for fold differences with the leaf samples. The 2-week leaf samples were used to find genes expressed 4-fold or higher in the leaf sample at 2 weeks of age versus all the other tissues. The remaining leaf samples at 5, 6, 8, and 11 weeks were not analyzed at this stage, but were analyzed independently. The leaf sample at 5 weeks was also analyzed against all other tissues except the remaining leaf samples for genes expressed 4-fold or higher in leaf tissue at 5 weeks. The other leaf samples were analyzed in a similar fashion. This allowed the selection of genes that were at least 4-fold elevated in expression in a leaf sample in at least one stage of development. When these genes were combined, there were 92 genes that were preferentially expressed in leaf tissue.

Image Analysis and Data Mining

Two text files are included in the analysis:

a. One with Absolute analysis: giving the status of each gene, either absent or present in the samples B. The other with Comparison analysis: comparing gene expression levels between two samples

*Arabidopsis* Genome Array

A high-density *Arabidopsis* oligonucleotide array was used that includes probes for 8,100 *Arabidopsis* genes and 40 probes for spiking and negative controls. For each gene, there are 16 probe pairs (probe sets) including perfect match probes and mismatch probes for non-specific binding control. The *Arabidopsis* genes are represented by known genes, predicted genes and approximately 100 clusters of ESTs. Predicted gene sequences were extracted and confirmed computationally by matching the genome sequence with ESTs and protein sequences.

The reproducibility of the array was characterized by calculation of the rate of false changes (number of genes significantly changed over the total number of genes on the array; Lipshultz, 1999). Two cDNA and subsequently cRNA (the antisense RNA synthesized by in vitro transcription using cDNAs as templates in the presence of biotinylated ribonucleotides) samples were prepared in parallel from the same total RNA samples, and hybridized to two different arrays manufactured in the same lot or different lots. Genes that showed changes of ≧2-fold and a signal threshold above the background (calculated according to the setting of the global scaling factor) were counted as false changes. Data from 15 pairs of array experiments indicated that false changes between two experiments using arrays of the same lot is 0.17% (based on 8 pairs), while the false change using arrays of two different lots is 0.22% (based on 7 pairs). Further analyses of these genes indicate that the fold change and expression levels are low and close to the threshold (Zhu and Wang, 2000).

Selected housekeeping genes are used to ensure the quality of the array experiments, because the quality of the total RNA and subsequently synthesized cDNA and cRNA samples has direct impact on the array results. Sample quality, specifically, labeled cRNA quality was monitored by comparing the ratio of the hybridization signal of 3' and 5' probe sets for GAPDH and ubiqutin11. Only data with a consistent 3'/5' ratio (Zhu and Wang, 2000) was archived in the database and used.

Specific Selection Criteria

The following criteria selection were employed to identify *Arabidopsis* genes that were constitutively expressed.

Baseline (background)=relative expression level of 50
Candidates were first selected for relative expression of ≧250 in all tissues for a given gene.
Relative expression range of the 346 genes which were expressed in all tissue=250-6,765.
Candidate genes were selected for +/−5 fold difference in expression=331 genes
Candidate genes were selected for +/−3 fold difference=276 genes
For 174 selected genes which met the above criteria
The expression for each gene was averaged:
 'low' expression=250-750; 97 genes (55.7%)
 'moderate' expression=750-2250; 70 genes (40.2%)
 'high' expression=2250-6750; 8 genes (4.6%)
genes were selected for further analysis
 'low' expression=250-750; 21 genes (44.6%)
 'moderate' expression=750-2250; 24 genes (51.0%)
 'high' expression=2250-6750; 3 genes (6.4%)

The following criteria were used to identify *Arabidopsis* genes expressed primarily in root tissue.

Baseline (background)=relative expression level of 50
Candidates were first selected for relative expression of ≧300 in all tissues for a given gene excluding the germinating seed data.
Candidate genes were sorted by fold difference. Root +/−3 other tissue <10 (10 fold lower expression)
When the germinating seed data included was included with the 64 selected genes 39 were identified with relative expression ≧150.
Thirteen were selected for further analysis.

Results

Abundance Distribution of Transcripts

Knowledge of the levels of all detectable mRNA species in *Arabidopsis* is useful for evaluating the complexity of the transcriptome and its control. The abundance of the transcript species and their expression level in 5-week-old *Arabidopsis* was analyzed by examining the mRNA transcripts present in four major organs, leaves, roots, inflorescence stems, and flowers. Among 8,300 genes analyzed, over 5,000 transcript species were detected in each organ. Comparison of the transcripts presented in these organs revealed the number and percentage of the commonly expressed and specifically expressed transcripts in each organ at this stage (Table 3).

TABLE 3

|  | Root | Inflorescence Stem | Leaf | Flower |
|---|---|---|---|---|
| Root | 6,052 | 4,928 | 4,915 | 5,243 |
| Inflorescence Stem |  | 5,399 | 4,828 | 5,036 |
| Leaf |  |  | 5,416 | 4,995 |
| Flower |  |  |  | 6,097 |
| Specific | 426 | 55 | 89 | 380 |

Expression measurements (average signal difference between perfect-match probes and mismatch probes) of the genes in each organ were examined. Data were collected and log transformed, then plotted against their frequencies. A normal distribution of the transcript abundance was revealed for all four organs. The median of the distributions is similar to the profiles of yeast, mammalian, and *E. coli* (Lockhart and Winzler, 2000). Overall, the transcription profile is more complex in flowers than in the vegetative organs. It is evidenced by the elevated frequencies in almost every level of transcription. Root has the most complex profile among the vegetative organs, while leaf and inflorescence stem have very similar and simpler profiles.

Constitutive and Organ Differential Gene Expression

The composition of the constitutively and organ differentially expressed transcripts were characterized. A total of 347 constitutive expressed genes with median or high-level transcripts were selected from the commonly expressed gene pool (Table 4). These genes are constantly expressed above median expression level (average difference greater than 500) for all organs and developmental stages examined. Functional categorization indicated that majority of the known constitutive genes are involved in metabolism (28%) and ribosomal protein synthesis (15%), followed by genes involving transcription (8%), signaling (6%), transport (5%), membrane (5%), synthases (5%), membrane (5%), and stress and defense related (7%). About 15% of the genes identified have no function assigned.

TABLE 4

Constitutively expressed *Arabidopsis* sequences and their corresponding genes.

| Gene ID | Accession # on chip | Affy # | Description |
|---|---|---|---|
| A45785.1_S_AT | A45785.1 | 19852_s_at | emb|CAA02840.1|(A45785) unnamed protein product [*Arabidopsis thaliana*] |
| AB003522.2_AT | AB003522.2 | 12381_at | dbj|BAA84392.1|(AP000423) ATPase beta subunit [*Arabidopsis thaliana*] |
| AB004872.6_S_AT | AB004872.6 | 15997_s_at | dbj|BAA23547.1|(AB004872) COR47 [*Arabidopsis thaliana*] |
| AB005560_S_AT | AB004872.6 | 15630_s_at | dbj|BAA22504.1|(AB005560) AtGDI2 [*Arabidopsis thaliana*] |

TABLE 4-continued

Constitutively expressed *Arabidopsis* sequences and their corresponding genes.

| Gene ID | Accession # on chip | Affy # | Description |
| --- | --- | --- | --- |
| AB006693.1__AT | AB006693.1 | 17438_at | dbj|BAA24536.1|(AB006693) spermidine synthase [*Arabidopsis thaliana*] |
| AB008105_S_AT | AB008105 | 17044_s_at | dbj|BAA32420.1|(AB008105) ethylene responsive element binding factor 3 [*Arabidopsis thaliana*] |
| AB008487_S_AT | AB008487 | 15127_s_at | dbj|BAA31143.1|(AB010915) responce regulator1 [*Arabidopsis thaliana*] |
| AB008854_S_AT | AB008854 | 14719_s_at | dbj|BAA25248.1|(AB008854) 3-ketoacyl-CoA thiolase [*Arabidopsis thaliana*] |
| AB010946_S_AT | AB010946 | 15200_s_at | dbj|BAA24804.1|(AB010946) AtRer1B [*Arabidopsis thaliana*] |
| AB011545_S_AT | AB011545 | 15163_s_at | dbj|BAA32735.1|(AB011545) GF14 mu [*Arabidopsis thaliana*] *thaliana*] |
| AB017643_S_AT | AB017643 | 15164_s_at | gb|AAC14411.1|(AF049236) putative acyl-coA dehydrogenase [*Arabidopsis thaliana*] |
| AB021858_S_AT | AB021858 | 16540_s_at | dbj|BAA77759.1|(AB021858) plastid heme oxygenase [*Arabidopsis thaliana*] |
| AB024282_S_AT | AB024282 | 15128_s_at | emb|CAB71074.1|(AL132962) cysteine synthase AtcysC1 [*Arabidopsis thaliana*] |
| AB027151.2_S_AT | AB027151.2 | 19179_s_at | emb|CAB43659.1|(AL050352) threonine synthase [*Arabidopsis thaliana*] |
| AC000103.25_S_AT | AC000103.25 | 20709_s_at | gb|AAB61517.1|(AC000103) F21J9.25 [*Arabidopsis thaliana*] |
| AC000104.10_R_AT | AC000104.10 | 13076_r_at | gb|AAB70426.1|(AC000104) Strong similarity to 60S ribosomal protein L17 (gb|X01694). EST gb|AA042332 comes from this gene. [*Arabidopsis thaliana*] |
| AC000104.26_AT | AC000104.26 | 12771_at | gb|AAB70434.1|(AC000104) F19P19.13 [*Arabidopsis thaliana*] |
| AC000106.13_S_AT | AC000106.13 | 17900_s_at | gb|AAB70401.1|(AC000106) Similar to Glycine SRC2 (gb|AB000130). ESTs gb|H76869, gb|T21700, gb|ATTS5089 come from this gene. [*Arabidopsis thaliana*] |
| AC000132.16_S_AT | AC000132.16 | 16531_s_at | gb|AAC33220.1|(AC003970) Putative ribosomal protein L21 [*Arabidopsis thaliana*] gb|AA395597, gb|ATTS5197 come from this gene. [*Arabidopsis thaliana*] |
| AC000132.6_AT | AC000132.6 | 16420_at | gb|AAB60721.1|(AC000132) Similar to elongation factor 1-gamma (gb|EF1G_XENLA). ESTs gb|T20564, gb|T45940, gb|T04527 come from this gene. [*Arabidopsis thaliana*] |
| AC002131.48_S_AT | AC002131.48 | 12750_s_at | gb|AAC17620.1|(AC002131) Identical to aspartic proteinase cDNA gb|U51036 from *A. thaliana*. ESTs gb|N96313, gb|T21893, gb|R30158, gb|T21482, gb|T43650, gb|R64749, gb|R65157, gb|T88269, gb|T44552, gb|T22542, gb|T76533, gb|T44350, gb|Z34591, gb|AA728734, g |
| AC002329.46_AT | AC002329.46 | 13074_at | emb|CAA54095.1|(X76651) ribosomal protein S4 [*Solanum tuberosum*] |
| AC002330.39_AT | AC002330.39 | 13574_at | gb|AAC78269.1|AAC78269 (AC002330) putative vacuolar ATPase [*Arabidopsis thaliana*] |
| AC002332.100_AT | AC002332.100 | 13105_at | gb|AAB80655.1|(AC002332) 60S ribosomal protein L23 [*Arabidopsis thaliana*] |
| AC002332.71_AT | AC002332.71 | 17435_at | gb|AAB80652.1|(AC002332) putative PRP19-like spliceosomal protein [*Arabidopsis thaliana*] |
| AC002334.110_G_AT | AC002334.110 | 16940_g_at | gb|AAC04922.1|(AC002334) putative synaptobrevin [*Arabidopsis thaliana*] |

TABLE 4-continued

Constitutively expressed *Arabidopsis* sequences and their corresponding genes.

| Gene ID | Accession # on chip | Affy # | Description |
|---|---|---|---|
| AC002336.101_G_AT | AC002336.101 | 12809_g_at | gb\|AAB87594.1\|(AC002336) 40S ribosomal protein S26 [*Arabidopsis thaliana*] |
| AC002339.51_AT | AC002339.51 | 16507_at | gb\|AAC02764.1\|(AC002339) 40S ribosomal protein S2 [*Arabidopsis thaliana*] |
| AC002343.3_AT | AC002343.3 | 16447_at | gb\|AAB63606.1\|(AC002343) HSP90 isolog [*Arabidopsis thaliana*] |
| AC002521.146_AT | AC002521.146 | 16917_at | gb\|AAC05346.1\|(AC002521) putative ubiquitin-conjugating enzyme E2 [*Arabidopsis*] |
| AC002561.51_AT | AC002561.51 | 18655_at | gb\|AAB88646.1\|(AC002561) unknown protein [*Arabidopsis thaliana*] |
| AC003672.64_S_AT | AC003672.64 | 20425_s_at | gb\|AAC27463.1\|(AC003672) putative small GTP-binding protein [*Arabidopsis thaliana*] |
| AC003981.34_S_AT | AC003981.34 | 16523_s_at | gb\|AAC14060.1\|(AC003981) F22O13.34 [*Arabidopsis thaliana*] |
| AC004077.166_S_AT | AC004077.166 | 17004_s_at | gb\|AAC26708.1\|(AC004077) 60S ribosomal protein L18A [*Arabidopsis thaliana*] |
| AC004165.105_AT | AC004165.105 | 13125_at | gb\|AAC16961.1\|(AC004165) putative ubiquitin activating enzyme (UBA1) [*Arabidopsis*] |
| AC004218.83_S_AT | AC004218.83 | 13616_s_at | gb\|AAC27837.1\|(AC004218) 60S ribosomal protein L23A [*Arabidopsis thaliana*] |
| AC004393.22_AT | AC004393.22 | 16953_at | gb\|AAC18792.1\|(AC004393) Similar to ribosomal protein L17 gb\|X62724 from Hordeum vulgare. ESTs gb\|Z34728, gb\|F19974, gb\|T75677 and gb\|Z33937 come from this gene. [*Arabidopsis thaliana*] |
| AC004401.119_AT | AC004401.119 | 13594_at | gb\|AAC17825.1\|(AC004401) unknown protein [*Arabidopsis thaliana*] |
| AC004401.140_AT | AC004401.140 | 12767_at | gb\|AAB87096.2\|(AC002391) unknown protein [*Arabidopsis thaliana*] |
| AC004450.11_AT | AC004450.11 | 18882_at | gb\|AAC64298.1\|(AC004450) 3-isopropylmalate dehydratase, small subunit [*Arabidopsis thaliana*] |
| AC004450.83_AT | AC004450.83 | 18262_at | gb\|AAC64306.1\|(AC004450) unknown protein [*Arabidopsis thaliana*] |
| AC004481.84_AT | AC004481.84 | 13102_at | gb\|AAC27401.1\|(AC004481) putative protein transport protein SEC61 alpha subunit [*Arabidopsis thaliana*] |
| AC004557.10_AT | AC004557.10 | 17436_at | gb\|AAC80610.1\|(AC004557) F17L21.10 [*Arabidopsis thaliana*] |
| AC004557.20_AT | AC004557.20 | 17374_at | gb\|AAC80620.1\|(AC004557) F17L21.20 [*Arabidopsis thaliana*] |
| AC004557.8_AT | AC004557.8 | 18874_at | gb\|AAC80608.1\|(AC004557) F17L21.8 [*Arabidopsis thaliana*] |
| AC004665.121_S_AT | AC004665.121 | 18629_s_at | gb\|AAC28542.1\|(AC004665) remorin [*Arabidopsis thaliana*] |
| AC004665.31_S_AT | AC004665.31 | 15977_s_at | gb\|AAC28529.1\|(AC004665) aquaporin (plasma membrane intrinsic protein 1B) [*Arabidopsis thaliana*] |
| AC004669.34_AT | AC004669.34 | 16430_at | gb\|AAC20720.1\|(AC004669) glutathione S-transferase [*Arabidopsis thaliana*] |
| AC004747.160_S_AT | AC004747.160 | 15506_s_at | gb\|AAC31239.1\|(AC004747) unknown protein [*Arabidopsis thaliana*] |
| AC005169.214_AT | AC005169.214 | 18221_at | gb\|AAC62141.1\|(AC005169) 40S ribosomal protein S30 [*Arabidopsis thaliana*] |
| AC005169.221_AT | AC005169.221 | 18283_at | gb\|AAC62149.1\|(AC005169) putative ribosomal protein L28 [*Arabidopsis thaliana*] |

TABLE 4-continued

Constitutively expressed *Arabidopsis* sequences and their corresponding genes.

| Gene ID | Accession # on chip | Affy # | Description |
|---|---|---|---|
| AC005287.20_S_AT | AC005287.20 | 16027_s_at | gb|AAD25605.1|AC005287_7 (AC005287) Eukaryotic Initiation Factor 4A-2 [*Arabidopsis thaliana*] |
| AC005287.52_AT | AC005287.52 | 14073_at | No hits found less than or equal to 1e−15. |
| AC005309.201_I_AT | AC005309.201 | 15570_i_at | gb|AAC63650.1|(AC005309) unknown protein [*Arabidopsis thaliana*] |
| AC005309.64_S_AT | AC005309.64 | 16009_s_at | gb|AAC63629.1|(AC005309) glutathione S-transferase (GST6) [*Arabidopsis thaliana*] |
| AC005388.6_S_AT | AC005388.6 | 12783_s_at | gb|AAC64875.1|(AC005388) Identical to gb|L14814 DNA for tissue-specific acyl carrier protein isoform 2 from *A. thaliana*. ESTs gb|AA597351, gb|T41805, gb|H36871, gb|R30210, gb|AA042549, gb|Z47650, gb|H76304 and gb|AA597348 come from this gene. [Arabidops |
| AC005397.40_S_AT | AC005397.40 | 16471_s_at | gb|AAC62877.1|(AC005397) eukaryotic translation initiation factor 3 delta subunit [*Arabidopsis thaliana*] |
| AC005662.30_S_AT | AC005662.30 | 16952_s_at | gb|AAC78532.1|(AC005662) calmodulin-like protein [*Arabidopsis thaliana*] |
| AC005679.10_S_AT | AC005679.10 | 12775_s_at | gb|AAC83021.1|(AC005679) Identical to gb|U65638 *Arabidopsis thaliana* vacuolar type ATPase subunit A mRNA. ESTs gb|N96435, gb|N96106, gb|N96189, gb|N96091, gb|AA042286, gb|F14324, gb|W43643, gb|N96027, gb|N96299, gb|R29943, gb|T43460, gb|T43544, gb|T2247 |
| AC005727.191_AT | AC005727.191 | 16901_at | gb|AAC79595.1|(AC005727) unknown protein [*Arabidopsis thaliana*] |
| AC005824.107_AT | AC005824.107 | 16527_at | gb|AAC73028.1|(AC005824) 60S acidic ribosomal protein P2 [*Arabidopsis thaliana*] |
| AC005824.114_AT | AC005824.114 | 17910_at | gb|AAC73029.1|(AC005824) 60S acidic ribosomal protein P2 [*Arabidopsis thaliana*] |
| AC005824.21_AT | AC005824.21 | 13089_at | gb|AAC73015.1|(AC005824) putative dTDP-glucose 4-6-dehydratase [*Arabidopsis thaliana*] |
| AC005896.150_S_AT | AC005896.150 | 18603_s_at | gb|AAC98060.1|(AC005896) putative protein translocase [*Arabidopsis thaliana*] |
| AC005897.156_S_AT | AC005897.156 | 13572_s_at | gb|AAC97246.1|(AC005897) 10-formyltetrahydrofolate synthetase [*Arabidopsis thaliana*] |
| AC005936.95_AT | AC005936.95 | 16416_at | gb|AAC97221.1|(AC005936) protease inhibitor II [*Arabidopsis thaliana*] |
| AC005990.10_AT | AC005990.10 | 13069_at | gb|AAC98042.1|(AC005990) Strong similarity to gb|M95166 ADP-ribosylation factor from *Arabidopsis thaliana*. ESTs gb|Z25826, gb|R90191, gb|N65697, gb|AA713150, gb|T46332, gb|AA040967, gb|AA712956, gb|T46403, gb|T46050, gb|AI100391 and gb|Z25043 come from |
| AC006068.93_AT | AC006068.93 | 18645_at | gb|AAD15447.1|(AC006068) unknown protein [*Arabidopsis thaliana*] |
| AC006085.15_AT | AC006085.15 | 20562_at | gb|AAD30634.1|AC006085_7 (AC006085) Unknown protein [*Arabidopsis thaliana*] |
| AC006200.119_AT | AC006200.119 | 13132_at | gb|AAD14525.1|(AC006200) 60S ribosomal protein L7 [*Arabidopsis thaliana*] |

TABLE 4-continued

Constitutively expressed *Arabidopsis* sequences and their corresponding genes.

| Gene ID | Accession # on chip | Affy # | Description |
|---|---|---|---|
| AC006201.107_S_AT | AC006201.107 | 16924_s_at | gb|AAD20124.1|(AC006201) 60S ribosomal protein L2 [*Arabidopsis thaliana*] |
| AC006223.65_AT | AC006223.65 | 14089_at | gb|AAD15390.1|(AC006223) putative hydrolase [*Arabidopsis thaliana*] |
| AC006234.156_AT | AC006234.156 | 14099_at | gb|AAD20913.1|(AC006234) unknown protein [*Arabidopsis thaliana*] |
| AC006260.52_AT | AC006260.52 | 12769_at | gb|AAD18142.1|(AC006260) aquaporin (plasma membrane intrinsic protein 2B) [*Arabidopsis thaliana*] |
| AC006264.30_AT | AC006264.30 | 13095_at | gb|AAD29800.1|AC006264_8 (AC006264) putative signal sequence receptor, alpha subunit |
| AC006300.112_AT | AC006300.112 | 16948_at | gb|AAD20708.1|(AC006300) putative glucose regulated repressor protein [*Arabidopsis thaliana*] |
| AC006300.70_AT | AC006300.70 | 16487_at | gb|AAD20704.1|(AC006300) putative dioxygenase [*Arabidopsis thaliana*] |
| AC006403.110_AT | AC006403.110 | 18223_at | gb|AAD18124.1|(AC006403) unknown protein [*Arabidopsis thaliana*] |
| AC006438.21_AT | AC006438.21 | 12749_at | gb|AAD41971.1|AC006438_3 (AC006438) similar to cold acclimation protein WCOR413 [*Triticum aestivum*] [*Arabidopsis thaliana*] |
| AC006526.57_AT | AC006526.57 | 14103_at | No hits found less than or equal to 1e−15. |
| AC006532.47_AT | AC006532.47 | 19940_at | gb|AAD20090.1|(AC006532) putative endosomal protein [*Arabidopsis thaliana*] |
| AC006577.32_AT | AC006577.32 | 16941_at | gb|AAD25780.1|AC006577_16 (AC006577) Similar to gb|U55861 RNA binding protein nucleolysin (TIAR) from *Mus musculus* and contains several PF|00076 RNA recognition motif domains. ESTs gb|T21032 and gb|T44127 come from this gene. [*Arabidopsis thaliana*] |
| AC006585.146_AT | AC006585.146 | 14565_at | gb|AAD23019.1|AC006585_14 (AC006585) putative steroid binding protein [*Arabidopsis thaliana*] |
| AC006586.141_AT | AC006586.141 | 17390_at | gb|AAD22696.1|AC006586_5 (AC006586) 40S ribosomal protein S16 [*Arabidopsis thaliana*] |
| AC006592.150_S_AT | AC006592.150 | 15980_s_at | emb|CAA47427.1|(X67034) Athb-6 [*Arabidopsis thaliana*] |
| AC006841.122_AT | AC006841.122 | 19650_at | gb|AAD23699.1|AC006841_15 (AC006841) coatomer alpha subunit [*Arabidopsis thaliana*] |
| AC006919.140_AT | AC006919.140 | 12742_at | gb|AAD24635.1|AC006919_15 (AC006919) enolase (2-phospho-D-glycerate hydroylase) [*Arabidopsis* |
| AC006919.171_AT | AC006919.171 | 13070_at | gb|AAD24640.1|AC006919_20 (AC006919) putative pyruvate kinase [*Arabidopsis thaliana*] |
| AC006921.52_AT | AC006921.52 | 16511_at | gb|AAD21434.1|(AC006921) unknown protein [*Arabidopsis thaliana*] |
| AC006922.106_AT | AC006922.106 | 12412_at | gb|AAD31573.1|AC006922_5 (AC006922) putative s-adenosylmethionine synthetase [*Arabidopsis thaliana*] |
| AC006922.28_S_AT | AC006922.28 | 15962_s_at | gb|AAD31569.1|AC006922_1 (AC006922) putative aquaporin (tonoplast intrinsic protein gamma) |
| AC006929.77_AT | AC006929.77 | 13150_at | gb|AAD21502.1|(AC006929) putative rubisco subunit binding-protein alpha subunit [*Arabidopsis thaliana*] |

TABLE 4-continued

Constitutively expressed *Arabidopsis* sequences and their corresponding genes.

| Gene ID | Accession # on chip | Affy # | Description |
|---|---|---|---|
| AC006951.208_S_AT | AC006951.208 | 13107_s_at | gb\|AAD25839.1\|AC006951_18 (AC006951) 40S ribosomal protein S17 [*Arabidopsis thaliana*] |
| AC007017.278_S_AT | AC007017.278 | 20024_s_at | gb\|AAD21476.1\|(AC007017) unknown protein [*Arabidopsis thaliana*] |
| AC007019.105_AT | AC007019.105 | 16022_at | gb\|AAD20405.1\|(AC007019) putative ATP synthase [*Arabidopsis thaliana*] |
| AC007070.167_AT | AC007070.167 | 13166_at | emb\|CAA64728.1\|(X95458) ribosomal protein L39 [*Zea mays*] |
| AC007071.72_AT | AC007071.72 | 16933_at | gb\|AAD24852.1\|AC007071_24 (AC007071) 40S ribosomal protein; contains C-terminal domain [*Arabidopsis thaliana*] |
| AC007119.88_AT | AC007119.88 | 13080_at | gb\|AAD23647.1\|AC007119_13 (AC007119) 40S ribosomal protein S25 [*Arabidopsis thaliana*] |
| AC007135.50_AT | AC007135.50 | 16919_at | gb\|AAD26971.1\|AC007135_8 (AC007135) 40S ribosomal protein S14 [*Arabidopsis thaliana*] |
| AC007138.25_S_AT | AC007138.25 | 12797_s_at | gb\|AAD22647.1\|AC007138_11 (AC007138) S-adenosylmethionine synthase 2 [*Arabidopsis thaliana*] |
| AC007170.48_AT | AC007170.48 | 17857_at | gb\|AAD25640.1\|AC007170_2 (AC007170) cytoplasmic aconitate hydratase [*Arabidopsis thaliana*] |
| AC007195.93_I_AT | AC007195.93 | 16969_i_at | gb\|AAA99933.1\|(L44581) vacuolar H+-pumping ATPase 16 kDa proteolipid [*Arabidopsis* [*Arabidopsis thaliana*] |
| AC007357.17_S_AT | AC007357.17 | 13104_s_at | emb\|CAA74029.1\|(Y13695) multicatalytic endopeptidase complex, proteasome precursor, beta subunit [*Arabidopsis thaliana*] |
| AC007576.5_AT | AC007576.5 | 12781_at | gb\|AAD39279.1\|AC007576_2 (AC007576) Unknown protein [*Arabidopsis thaliana*] |
| AC007659.93_R_AT | AC007659.93 | 13169_r_at | gb\|AAD32831.1\|AC007659_13 (AC007659) putative GATA-type zinc finger transcription factor [*Arabidopsis thaliana*] |
| AF000657.40_AT | AF000657.40 | 19623_at | gb\|AAB72175.1\|(AF000657) cytochrome C [*Arabidopsis thaliana*] |
| AF001394_S_AT | AF001394 | 15600_s_at | gb\|AAD00895.1\|(AF001394) fatty acid desaturase/cytochrome b5 fusion protein [*Arabidopsis thaliana*] |
| AF003096_F_AT | AF003096 | 14723_f_at | gb\|AAC49769.1\|(AF003096) AP2 domain containing protein RAP2.3 [*Arabidopsis thaliana*] |
| AF003105.1_AT | AF003105.1 | 17858_at | gb\|AAC49778.1\|(AF003105) AP2 domain containing protein RAP2.12 [*Arabidopsis thaliana*] |
| AF004216_S_AT | AF004216 | 15205_s_at | gb\|AAC49749.1\|(AF004216) ethylene-insensitive3 [*Arabidopsis thaliana*] |
| AF004393_S_AT | AF004393 | 14714_s_at | gb\|AAB62692.1\|(AF004393) salt-stress induced tonoplast intrinsic protein [*Arabidopsis thaliana*] |
| AF013294.25_S_AT | AF013294.25 | 18650_s_at | gb\|AAB62867.1\|(AF013294) AT0ZI1 gene product [*Arabidopsis thaliana*] |
| AF013294.35_AT | AF013294.35 | 18573_at | gb\|AAB62855.1\|(AF013294) similar to acidic ribosomal protein p1 [*Arabidopsis thaliana*] |
| AF013959.4_AT | AF013959.4 | 16436_at | gb\|AAB67234.1\|(AF013959) metallothionein-like protein [*Arabidopsis thaliana*] |
| AF017641_S_AT | AF017641 | 15165_s_at | gb\|AAC17844.1\|(AF017641) nucleoside diphosphate kinase type 1 [*Arabidopsis* |
| AF017991_S_AT | AF017991 | 15150_s_at | gb\|AAB97312.1\|(AF017991) salt stress inducible small GTP binding protein Ran1 |
| AF027172.3_S_AT | AF027172.3 | 16906_s_at | gb\|AAC39334.1\|(AF027172) cellulose synthase catalytic subunit [*Arabidopsis thaliana*] |

TABLE 4-continued

Constitutively expressed *Arabidopsis* sequences and their corresponding genes.

| Gene ID | Accession # on chip | Affy # | Description |
| --- | --- | --- | --- |
| AF027174_S_AT | AF027174 | 15603_s_at | gb\|AAC39336.1\|(AF027174) cellulose synthase catalytic subunit [*Arabidopsis thaliana*] |
| AF034387_S_AT | AF034387 | 14727_s_at | gb\|AAC33264.1\|(AF034387) AFT protein [*Arabidopsis thaliana*] |
| AF034694_S_AT | AF034694 | 16544_s_at | gb\|AAB87692.1\|(AF034694) ribosomal protein L23a [*Arabidopsis thaliana*] |
| AF043519_S_AT | AF043519 | 15130_s_at | gb\|AAC95161.1\|(AC005970) 20S proteasome subunit (PAA2) [*Arabidopsis thaliana*] |
| AF043528_S_AT | AF043528 | 16546_s_at | gb\|AAC32064.1\|(AF043528) 20S proteasome subunit PAG1 [*Arabidopsis thaliana*] |
| AF044265_S_AT | AF044265 | 15668_s_at | gb\|AAC00512.1\|(AF044265) nucleoside diphosphate kinase 3 [*Arabidopsis thaliana*] |
| AF044313_S_AT | AF044313 | 14717_s_at | gb\|AAC05742.1\|(AF044313) anion channel protein [*Arabidopsis thaliana*] |
| AF059294_S_AT | AF059294 | 14736_s_at | gb\|AAF26761.1\|AC007396_10 (AC007396) T4O12.15 [*Arabidopsis thaliana*] protein in budding yeast [*Arabidopsis thaliana*] |
| AF061519_S_AT | AF061519 | 15581_s_at | gb\|AAD10208.1\|(AF061519) copper/zinc superoxide dismutase [*Arabidopsis thaliana*] |
| AF062485.1_AT | AF062485.1 | 17468_at | gb\|AAC29067.1\|(AF062485) cellulose synthase [*Arabidopsis thaliana*] |
| AF063901_S_AT | AF063901 | 14737_s_at | gb\|AAC26854.1\|(AF063901) alanine:glyoxylate aminotransferase; transaminase [*Arabidopsis thaliana*] |
| AF069299.19_AT | AF069299.19 | 16925_at | gb\|AAC19305.1\|(AF069299) similar to ribosomal protein S13 (Pfam; S15.hmm, score: 78.35); identical to *Arabidopsis* 40S ribosomal protein S13 (fragment) (SW: P49203A) except the first 32 amino acids are different [*Arabidopsis thaliana*] |
| AF074375_S_AT | AF074375 | 15114_s_at | gb\|AAC83240.1\|(AF073875) endo-1,4-beta-D-glucanase KORRIGAN [*Arabidopsis thaliana*] |
| AF076484_S_AT | AF076484 | 16627_s_at | gb\|AAD04627.1\|(AF108660) CYT1 protein [*Arabidopsis thaliana*] |
| AF076641.2_AT | AF076641.2 | 16977_at | gb\|AAD46064.1\|AF076641_1 (AF076641) homeodomain leucine-zipper protein ATHB16 [*Arabidopsis thaliana*] |
| AF077528_S_AT | AF077528 | 15152_s_at | gb\|AAB72116.1\|(U69533) AtKAP alpha [*Arabidopsis thaliana*] |
| AF080120.11_S_AT | AF080120.11 | 16935_s_at | gb\|AAC35545.1\|(AF080120) similar to vacuolar ATPases [*Arabidopsis thaliana*] thaliana] |
| AF082565_S_AT | AF082565 | 15639_s_at | gb\|AAD29109.1\|AF082565_1 (AF082565) ATP dependent copper transporter [*Arabidopsis thaliana*] |
| AF083336.2_S_AT | AF083336.2 | 16932_s_at | gb\|AAD10030.1\|(AF083337) ribosomal protein S27 [*Arabidopsis thaliana*] |
| AF083337.3_S_AT | AF083337.3 | 16931_s_at | gb\|AAD10030.1\|(AF083337) ribosomal protein S27 [*Arabidopsis thaliana*] |
| AF118822_F_AT | AF118822 | 16080_f_at | gb\|AAD20612.1\|(AF118822) senescence-associated protein [*Arabidopsis thaliana*] |
| AF123253.3_I_AT | AF123253.3 | 20459_i_at | emb\|CAB43915.1\|(AL078470) AIM1 protein [*Arabidopsis thaliana*] |
| AF136152_S_AT | AF136152 | 15643_s_at | gb\|AAD39465.1\|AF136152_1 (AF136152) PUR alpha-1 [*Arabidopsis thaliana*] |
| AF144387_AT | AF144387 | 12857_at | gb\|AAD35005.1\|AF144387_1 (AF144387) thioredoxin-like 1 [*Arabidopsis thaliana*] |

TABLE 4-continued

Constitutively expressed *Arabidopsis* sequences and their corresponding genes.

| Gene ID | Accession # on chip | Affy # | Description |
|---|---|---|---|
| AF167983_S_AT | AF167983 | 15210_s_at | gb\|AAC26685.1\|(AC004077) putative pyruvate dehydrogenase E1 beta subunit [*Arabidopsis thaliana*] |
| AF181688_R_AT | AF181688 | 17994_r_at | gb\|AAF24609.1\|AC010870_2 (AC010870) vacuolar membrane ATPase subunit G (AVMA10) [*Arabidopsis thaliana*] |
| AF181966_AT | AF181966 | 17996_at | gb\|AAD55787.1\|AF181966_1 (AF181966) methylenetetrahydrofolate reductase MTHFR1 [*Arabidopsis thaliana*] |
| AF186847_S_AT | AF186847 | 18000_s_at | gb\|AAF03749.1\|AF186847_1 (AF186847) TIM17 [*Arabidopsis thaliana*] |
| AGO1_S_AT | AGO1 | 12877_s_at | gb\|AAD49755.1\|AC007932_3 (AC007932) Identical to gb\|U91995 Argonaute protein from *Arabidopsis* |
| AJ001342.2_S_AT | AJ001342.2 | 16923_s_at | emb\|CAA18846.1\|(AL023094) Putative S-phase-specific ribosomal protein [*Arabidopsis thaliana*] |
| AJ001397_S_AT | AJ001397 | 18011_s_at | dbj\|BAA22504.1\|(AB005560) AtGDI2 [*Arabidopsis thaliana*] |
| AJ006787.1_AT | AJ006787.1 | 19224_at | emb\|CAA07251.1\|(AJ006787) putative phytochelatin synthetase [*Arabidopsis thaliana*] |
| AJ010456.2_AT | AJ010456.2 | 17470_at | emb\|CAA09195.1\|(AJ010456) RNA helicase [*Arabidopsis thaliana*] |
| AJ010505_S_AT | AJ010505 | 18018_s_at | emb\|CAB54830.1\|(AJ010505) cysteine synthase [*Arabidopsis thaliana*] |
| AJ011628_I_AT | AJ011628 | 18032_i_at | emb\|CAB56580.1\|(AJ011628) squamosa promoter binding protein-like 1 [*Arabidopsis thaliana*] |
| AJ012571.2_S_AT | AJ012571.2 | 16012_s_at | emb\|CAA10060.1\|(AJ012571) glutathione transferase [*Arabidopsis thaliana*] |
| AJ131205_AT | AJ131205 | 18047_at | emb\|CAA10320.1\|(AJ131205) mitochondrial NAD-dependent malate dehydrogenase [*Arabidopsis thaliana*] |
| AL021636.178_AT | AL021636.178 | 16499_at | emb\|CAA16587.1\|(AL021636) putative protein [*Arabidopsis thaliana*] |
| AL021687.199_AT | AL021687.199 | 19677_at | emb\|CAA16709.1\|(AL021687) putative protein [*Arabidopsis thaliana*] |
| AL021712.156_AT | AL021712.156 | 20559_at | emb\|CAA16781.1\|(AL021712) putative protein [*Arabidopsis thaliana*] |
| AL021811.156_AT | AL021811.156 | 12776_at | emb\|CAA16969.1\|(AL021811) putative protein [*Arabidopsis thaliana*] |
| AL021890.14_AT | AL021890.14 | 13591_at | emb\|CAA17148.1\|(AL021890) putative protein [*Arabidopsis thaliana*] |
| AL021890.209_S_AT | AL021890.209 | 12752_s_at | emb\|CAA17163.1\|(AL021890) peroxidase prxr1 [*Arabidopsis thaliana*] |
| AL022023.145_S_AT | AL022023.145 | 16905_s_at | emb\|CAA17773.1\|(AL022023) catalase [*Arabidopsis thaliana*] |
| AL022141.10_S_AT | AL022141.10 | 16976_s_at | emb\|CAA18507.1\|(AL022373) ribosomal protein L2 [*Arabidopsis thaliana*] |
| AL022224.182_S_AT | AL022224.182 | 16021_s_at | emb\|CAA18251.1\|(AL022224) endomembrane-associated protein [*Arabidopsis thaliana*] |
| AL022224.72_AT | AL022224.72 | 13122_at | emb\|CAA18240.1\|(AL022224) putative protein [*Arabidopsis thaliana*] |
| AL022373.153_AT | AL022373.153 | 12802_at | emb\|CAA18498.1\|(AL022373) DnaJ-like protein [*Arabidopsis thaliana*] |
| AL022580.188_AT | AL022580.188 | 17878_at | emb\|CAA18628.1\|(AL022580) putative pectinacetylesterase protein [*Arabidopsis thaliana*] |

TABLE 4-continued

Constitutively expressed *Arabidopsis* sequences and their corresponding genes.

| Gene ID | Accession # on chip | Affy # | Description |
| --- | --- | --- | --- |
| AL023094.216_S_AT | AL023094.216 | 12234_s_at | emb\|CAA18841.1\|(AL023094) putative ribosomal protein S16 [*Arabidopsis thaliana*] |
| AL023094.323_S_AT | AL023094.323 | 16515_s_at | emb\|CAA18849.1\|(AL023094) putative protein [*Arabidopsis thaliana*] |
| AL031326.138_AT | AL031326.138 | 17931_at | emb\|CAA20461.1\|(AL031326) water channel-like protein [*Arabidopsis thaliana*] |
| AL034567.189_AT | AL034567.189 | 13088_at | emb\|CAA22574.1\|(AL034567) ubiquinol-cytochrome c reductase-like protein [*Arabidopsis thaliana*] |
| AL035356.123_AT | AL035356.123 | 13097_at | emb\|CAA22994.1\|(AL035356) putative protein [*Arabidopsis thaliana*] |
| AL035394.117_AT | AL035394.117 | 17384_at | emb\|CAA23029.1\|(AL035394) putative protein [*Arabidopsis thaliana*] |
| AL035440.191_S_AT | AL035440.191 | 13133_s_at | emb\|CAB36530.1\|(AL035440) ubiquitin-like protein [*Arabidopsis thaliana*] |
| AL035440.447_AT | AL035440.447 | 17011_at | emb\|CAB36546.1\|(AL035440) putative DNA binding protein [*Arabidopsis thaliana*] |
| AL035440.66_AT | AL035440.66 | 18661_at | emb\|CAB36517.1\|(AL035440) putative protein [*Arabidopsis thaliana*] |
| AL035526.101_S_AT | AL035526.101 | 13073_s_at | emb\|CAB37458.1\|(AL035526) ribosomal protein L11, cytosolic [*Arabidopsis thaliana*] |
| AL035540.348_S_AT | AL035540.348 | 19961_s_at | gb\|AAB24074.1\|(S47408) glycine-rich protein, atGRP {clone atGRP-2} [*Arabidopsis* |
| AL035540.94_AT | AL035540.94 | 12804_at | emb\|CAB37507.1\|(AL035540) probable H+-transporting ATPase [*Arabidopsis thaliana*] |
| AL035656.126_AT | AL035656.126 | 17459_at | emb\|CAB38614.1\|(AL035656) putative protein [*Arabidopsis thaliana*] |
| AL035679.13_S_AT | AL035679.13 | 16967_s_at | gb\|AAA99933.1\|(L44581) vacuolar H+-pumping ATPase 16 kDa proteolipid [*Arabidopsis* [*Arabidopsis thaliana*] |
| AL035679.232_AT | AL035679.232 | 18905_at | emb\|CAB38828.1\|(AL035679) putative proton pump [*Arabidopsis thaliana*] |
| AL035680.110_S_AT | AL035680.110 | 17429_s_at | emb\|CAB38843.1\|(AL035680) translation initiation factor [*Arabidopsis thaliana*] |
| AL035680.53_AT | AL035680.53 | 13578_at | emb\|CAB38839.1\|(AL035680) ribosomal protein L14-like protein [*Arabidopsis thaliana*] |
| AL035709.87_AT | AL035709.87 | 17389_at | emb\|CAB38931.1\|(AL035709) putative protein [*Arabidopsis thaliana*] |
| AL049171.158_AT | AL049171.158 | 20180_at | No hits found less than or equal to 1e−15. |
| AL049171.25_AT | AL049171.25 | 17005_at | emb\|CAB38952.1\|(AL049171) putative ribosomal protein [*Arabidopsis thaliana*] |
| AL049480.178_AT | AL049480.178 | 13940_at | emb\|CAB39610.1\|(AL049480) putative acidic ribosomal protein [*Arabidopsis thaliana*] |
| AL049608.184_AT | AL049608.184 | 12813_at | emb\|CAB40778.1\|(AL049608) putative protein [*Arabidopsis thaliana*] |
| AL050300.15_F_AT | AL050300.15 | 13129_f_at | emb\|CAB43405.1\|(AL050300) ubiquitin/ribosomal protein CEP52 [*Arabidopsis thaliana*] |
| AL050300.27_AT | AL050300.27 | 16920_at | emb\|CAB43407.1\|(AL050300) putative ribosomal protein S14 [*Arabidopsis thaliana*] |
| AL050398.4_AT | AL050398.4 | 19133_at | emb\|CAB43690.1\|(AL050398) H+-transporting ATPase-like protein [*Arabidopsis thaliana*] |

TABLE 4-continued

Constitutively expressed *Arabidopsis* sequences and their corresponding genes.

| Gene ID | Accession # on chip | Affy # | Description |
|---|---|---|---|
| AL078464.37_AT | AL078464.37 | 14108_at | emb\|CAB43836.1\|(AL078464) putative protein [*Arabidopsis thaliana*] |
| AL078468.11_AT | AL078468.11 | 18330_at | emb\|CAB43885.1\|(AL078468) acyl-CoA synthetase-like protein [*Arabidopsis thaliana*] |
| AL078637.47_S_AT | AL078637.47 | 12803_s_at | emb\|CAB45057.1\|(AL078637) putative protein [*Arabidopsis thaliana*] |
| AL096856.7_AT | AL096856.7 | 13093_at | emb\|CAB51061.1\|(AL096856) B12D-like protein [*Arabidopsis thaliana*] |
| AL096860.157_AT | AL096860.157 | 13079_at | emb\|CAB51209.1\|(AL096860) 40S RIBOSOMAL PROTEIN S20 homolog [*Arabidopsis thaliana*] |
| AOS_S_AT | AOS | 12881_s_at | emb\|CAA63266.1\|(X92510) allene oxide synthase [*Arabidopsis thaliana*] |
| AP000423_AT | AP000423 | 12847_at | dbj\|BAA84366.1\|(AP000423) orf within trnK intron [*Arabidopsis thaliana*] |
| APX3_S_AT | APX3 | 12885_s_at | emb\|CAA66640.1\|(X98003) ascorbate peroxidase [*Arabidopsis thaliana*] |
| ATADHIII_AT | ATADHIII | 12893_at | emb\|CAA57973.1\|(X82647) class III ADH, glutathione-dependent formaldehyde dehydrogenase. [*Arabidopsis thaliana*] |
| ATERF3_S_AT | ATERF3 | 12906_s_at | dbj\|BAA32420.1\|(AB008105) ethylene responsive element binding factor 3 [*Arabidopsis thaliana*] |
| ATHADPRFA_S_AT | ATHADPRFA | 15677_s_at | gb\|AAA32729.1\|(M95166) ADP-ribosylation factor [*Arabidopsis thaliana*] |
| ATHAVAP_S_AT | ATHAVAP | 15191_s_at | gb\|AAA99933.1\|(L44581) vacuolar H+-pumping ATPase 16 kDa proteolipid [*Arabidopsis* [*Arabidopsis thaliana*] |
| ATHAVAPA_S_AT | ATHAVAPA | 15584_s_at | gb\|AAD26493.1\|AC007195_7 (AC007195) putative vacuolar proton-ATPase 16 kDa proteolipid [*Arabidopsis thaliana*] |
| ATHAVAPC_S_AT | ATHAVAPC | 16145_s_at | gb\|AAD38803.1\|AF153677_1 (AF153677) vacuolar H+-pumping ATPase 16 kDa subunit c isoform 4 *thaliana*] |
| ATHD12AAA_S_AT | ATHD12AAA | 15134_s_at | gb\|AAA32782.1\|(L26296) delta-12 desaturase [*Arabidopsis thaliana*] |
| ATHDYNAGTP_S_AT | ATHDYNAGTP | 15585_s_at | gb\|AAB63528.1\|(L36939) dynamin-like GTP binding protein [*Arabidopsis thaliana*] |
| ATHERD13_S_AT | ATHERD13 | 15193_s_at | gb\|AAC20721.1\|(AC004669) glutathione S-transferase [*Arabidopsis thaliana*] |
| ATHERD15_S_AT | ATHERD15 | 15104_s_at | gb\|AAC23728.1\|(AC004625) dehydration-induced protein (ERD15) [*Arabidopsis thaliana*] |
| ATHGFPSIA_S_AT | ATHGFPSIA | 14734_s_at | gb\|AAA32799.1\|(L09110) GF14 psi chain [*Arabidopsis thaliana*] |
| ATHHMG1_AT | ATHHMG1 | 12920_at | gb\|AAA32814.1\|(L19261) hydroxymethylglutaryl CoA reductase [*Arabidopsis thaliana*] |
| ATHHMGCOAR_S_AT | ATHHMGCOAR | 12921_s_at | emb\|CAA33139.1\|(X15032) hydroxy methylglutaryl CoA reductase (AA 1-592) |
| ATHMERI5B_S_AT | ATHMERI5B | 15614_s_at | emb\|CAB52471.1\|(AL109796) xyloglucan endo-1,4-beta-D-glucanase precursor [*Arabidopsis thaliana*] |
| ATHMTMACP_S_AT | ATHMTMACP | 16574_s_at | gb\|AAB96840.1\|(L23574) acyl carrier protein precursor [*Arabidopsis thaliana*] |
| ATHPRPHC_S_AT | ATHPRPHC | 15119_s_at | gb\|AAD10854.1\|(U60135) serine/threonine protein phosphatase 2A-3 catalytic |
| ATHRP28A_S_AT | ATHRP28A | 16577_s_at | gb\|AAA32862.1\|(L09755) ribosomal protein S28 [*Arabidopsis thaliana*] |

TABLE 4-continued

Constitutively expressed *Arabidopsis* sequences and their corresponding genes.

| Gene ID | Accession # on chip | Affy # | Description |
| --- | --- | --- | --- |
| ATHRPCA_S_AT | ATHRPCA | 15155_s_at | gb|AAA66160.1|(M32654) ribosomal protein [*Arabidopsis thaliana*] |
| ATHSAR1_S_AT | ATHSAR1 | 15617_s_at | gb|AAA56991.1|(M90418) formerly called HAT24; synaptobrevin-related protein [*Arabidopsis thaliana*] |
| ATORNCARB_S_AT | ATORNCARB | 15213_s_at | emb|CAA04115.1|(AJ000476) Ornithine carbamoyltransferase [*Arabidopsis thaliana*] |
| ATTHIRED2_S_AT | ATTHIRED2 | 13184_s_at | gb|AAC49351.1|(U35640) thioredoxin h [*Arabidopsis thaliana*] |
| ATTHIRED3_AT | ATTHIRED3 | 13185_at | emb|CAA84612.1|(Z35475) thioredoxin [*Arabidopsis thaliana*] |
| ATU01955_S_AT | ATU01955 | 15135_s_at | gb|AAF27153.1|AC016529_16 (AC016529) putative 40S ribosomal protein SA (laminin receptor-like |
| ATU09137_S_AT | ATU09137 | 15156_s_at | gb|AAA52225.1|(U09137) pyruvate dehydrogenase E1 beta subunit [*Arabidopsis thaliana*] |
| ATU15108_S_AT | ATU15108 | 17078_s_at | gb|AAA50250.1|(U15108) metallothionein-like protein [*Arabidopsis thaliana*] |
| ATU15130_S_AT | ATU15130 | 15157_s_at | No hits found. |
| ATU18410_S_AT | ATU18410 | 16156_s_at | gb|AAD15575.1|(AC006340) auxin-regulated protein (IAA8) [*Arabidopsis thaliana*] |
| ATU18675_S_AT | ATU18675 | 15620_s_at | gb|AAD47191.1|AF106084_1 (AF106084) 4-coumarate:CoA ligase 1 [*Arabidopsis thaliana*] |
| ATU20347_S_AT | ATU20347 | 15649_s_at | gb|AAA91976.1|(U20347) mRNA corresponding to this gene accumulates in response to |
| ATU21214_S_AT | ATU21214 | 15590_s_at | gb|AAA86507.1|(U21214) pyruvate dehydrogenase E1 alpha subunit [*Arabidopsis thaliana*] |
| ATU21557_S_AT | ATU21557 | 16098_s_at | gb|AAC49255.1|(U21557) phosphoprotein phosphatase 2A, regulatory subunit A [*Arabidopsis thaliana*] |
| ATU22340_S_AT | ATU22340 | 15136_s_at | gb|AAB49030.1|(U22340) DnaJ homolog [*Arabidopsis thaliana*] |
| ATU36765_S_AT | ATU36765 | 15177_s_at | gb|AAC49079.1|(U36765) TGF-beta receptor interacting protein 1 homolog [*Arabidopsis thaliana*] |
| ATU37235_S_AT | ATU37235 | 15195_s_at | emb|CAB58515.1|(A74281) unnamed protein product [*Arabidopsis thaliana*] |
| ATU37281_F_AT | ATU37281 | 16158_f_at | gb|AAB52506.1|(U27811) actin7 [*Arabidopsis thaliana*] |
| ATU37587_S_AT | ATU37587 | 13205_s_at | gb|AAC49120.1|(U37587) cell division cycle protein [*Arabidopsis thaliana*] |
| ATU39485_S_AT | ATU39485 | 15122_s_at | gb|AAC49281.1|(U39485) delta tonoplast integral protein [*Arabidopsis thaliana*] |
| ATU43325_S_AT | ATU43325 | 15691_s_at | gb|AAB39480.1|(U43325) profilin 1 [*Arabidopsis thaliana*] |
| ATU43397_S_AT | ATU43397 | 15112_s_at | gb|AAD09837.1|(U43397) cryptochrome 2 apoprotein [*Arabidopsis thaliana*] and cryptochrome 2 apoprotein (CRY2) (gb|U43397). ESTs gb|W43661 and gb|Z25638 come from this gene. [*Arabidopsis thaliana*] |
| ATU46665_S_AT | ATU46665 | 14730_s_at | gb|AAC31617.1|(U49937) glutamate decarboxylase [*Arabidopsis thaliana*] *Arabidopsis thaliana*. ESTs gb|W43856, gb|N37724, gb|Z34642 and gb|R90491 come from this gene. |
| ATU49072_S_AT | ATU49072 | 15215_s_at | gb|AAB84353.1|(U49072) IAA16 [*Arabidopsis thaliana*] |
| ATU49259_S_AT | ATU49259 | 15652_s_at | gb|AAF26982.1|AC018363_27 (AC018363) isopentenyl diphosphate:dimethylallyl diphosphate isomerase [*Arabidopsis thaliana*] |

TABLE 4-continued

Constitutively expressed *Arabidopsis* sequences and their corresponding genes.

| Gene ID | Accession # on chip | Affy # | Description |
|---|---|---|---|
| ATU52851_S_AT | ATU52851 | 15197_s_at | gb|AAB09723.1|(U52851) arginine decarboxylase [*Arabidopsis thaliana*] |
| ATU56929_S_AT | ATU56929 | 15180_s_at | gb|AAB57799.1|(AF001535) AGAA.4 [*Arabidopsis thaliana*] |
| ATU63633_S_AT | ATU63633 | 14721_s_at | gb|AAB17665.1|(U63633) S-adenosylmethionine decarboxylase [*Arabidopsis thaliana*] |
| ATU66343_S_AT | ATU66343 | 15654_s_at | gb|AAC49695.1|(U66343) calreticulin [*Arabidopsis thaliana*] |
| ATU68545_S_AT | ATU68545 | 14722_s_at | gb|AAA74737.1|(U02565) 14-3-3-like protein 1 [*Arabidopsis thaliana*] |
| ATU75191_S_AT | ATU75191 | 15216_s_at | gb|AAB51576.1|(U75198) germin-like protein [*Arabidopsis thaliana*] |
| ATU77381_S_AT | ATU77381 | 16106_s_at | gb|AAB82647.1|(U77381) WD-40 repeat protein [*Arabidopsis thaliana*] |
| ATU78297_F_AT | ATU78297 | 15100_f_at | gb|AAB36949.1|(U78297) plasma membrane intrinsic protein PIP3 [*Arabidopsis thaliana*] |
| ATU78870_S_AT | ATU78870 | 17030_s_at | gb|AAB68038.1|(U78866) gene1000 [*Arabidopsis thaliana*] |
| ATU79960_S_AT | ATU79960 | 16056_s_at | gb|AAB72112.1|(U79960) vacuolar sorting receptor homolog [*Arabidopsis thaliana*] |
| ATU80186_S_AT | ATU80186 | 15627_s_at | gb|AAB86804.1|(U80186) pyruvate dehydrogenase E1 beta subunit [*Arabidopsis thaliana*] |
| ATU91995_S_AT | ATU91995 | 16170_s_at | gb|AAD49755.1|AC007932_3 (AC007932) Identical to gb|U91995 Argonaute protein from Arabidopsis |
| CATL_S_AT | CATL | 13218_s_at | gb|AAC17732.1|(AF021937) catalase 3 [*Arabidopsis thaliana*] |
| CYSPROL_S_AT | CYSPROL | 13230_s_at | emb|CAB10398.1|(Z97340) cysteine proteinase like protein [*Arabidopsis thaliana*] |
| D01027.1_AT | D01027.1 | 18940_at | gb|AAC24370.1|(U89959) ARA-5 [*Arabidopsis thaliana*] |
| D11394.4_S_AT | D11394.4 | 16011_s_at | emb|CAA44630.1|(X62818) Metallothionein-like protein [*Arabidopsis thaliana*] |
| D13043.4_AT | D13043.4 | 15973_at | dbj|BAA02374.1|(D13043) thiol protease [*Arabidopsis thaliana*] |
| D83531_S_AT | D83531 | 15113_s_at | dbj|BAA11944.1|(D83531) GDP dissociation inhibitor [*Arabidopsis thaliana*] |
| D88374_S_AT | D88374 | 15149_s_at | dbj|BAA13599.1|(D88374) gamma subunit of mitochondrial F1-ATPase [*Arabidopsis* [*Arabidopsis thaliana*] |
| GLUTATHIONEPEROXIDASE1_S_AT | GLUTATHIONEPEROXIDASE1 | 13259_s_at | gb|AAD24836.1|AC007071_8 (AC007071) putative glutathione peroxidase [*Arabidopsis thaliana*] |
| GST1_RC_S_AT | GST1 | 13263_s_at | emb|CAA10060.1|(AJ012571) glutathione transferase [*Arabidopsis thaliana*] |
| GST2_S_AT | GST2 | 13264_s_at | emb|CAA72973.1|(Y12295) glutathione transferase [*Arabidopsis thaliana*] |
| GST8_S_AT | GST8 | 13267_s_at | emb|CAA10060.1|(AJ012571) glutathione transferase [*Arabidopsis thaliana*] |
| HSC701_S_AT | HSC701 | 13269_s_at | emb|CAA54419.1|(X77199) heat shock cognate 70-1 [*Arabidopsis thaliana*] |
| IAA16_S_AT | IAA16 | 13294_s_at | gb|AAB84353.1|(U49072) IAA16 [*Arabidopsis thaliana*] |
| IAA8_S_AT | IAA8 | 13663_s_at | gb|AAD15575.1|(AC006340) auxin-regulated protein (IAA8) [*Arabidopsis thaliana*] |
| J05216.2_S_AT | J05216.2 | 16985_s_at | gb|AAA32866.1|(J05216) ribosomal protein S11 (probable start codon at bp 67) [*Arabidopsis thaliana*] |
| L09755.2_S_AT | L09755.2 | 19682_s_at | gb|AAA32862.1|(L09755) ribosomal protein S28 [*Arabidopsis thaliana*] |
| L14844_3_S_AT | L14844 | 12824_s_at | No hits found less than or equal to 1e−15. |
| L15389_S_AT | L15389 | 18679_s_at | No hits found. |

TABLE 4-continued

Constitutively expressed *Arabidopsis* sequences and their corresponding genes.

| Gene ID | Accession # on chip | Affy # | Description |
|---|---|---|---|
| L26984_S_AT | L26984 | 18682_s_at | gb\|AAC27463.1\|(AC003672) putative small GTP-binding protein [*Arabidopsis thaliana*] |
| M21415.4_AT | M21415.4 | 15988_at | gb\|AAA32757.1\|(M21415) beta-tubulin [*Arabidopsis thaliana*] |
| M55077.2_AT | M55077.2 | 15993_at | gb\|AAA32868.1\|(M55077) S-adenosylmethionine synthetase [*Arabidopsis thaliana*] |
| M64116_3_S_AT | M64116 | 12827_s_at | gb\|AAA32794.1\|(M64116) cystolic glyceraldehyde-3-phosphate dehydrogenase (GapC) [*Arabidopsis thaliana*] |
| M84703.2_AT | M84703.2 | 16480_at | gb\|AAA32884.1\|(M84703) beta-6 tubulin [*Arabidopsis thaliana*] |
| ORYZAIN4_AT | ORYZAIN4 | 14245_at | dbj\|BAA02374.1\|(D13043) thiol protease [*Arabidopsis thaliana*] |
| ORYZAIN5_AT | ORYZAIN5 | 14246_at | emb\|CAA68192.1\|(X99936) cysteine protease [*Zea mays*] |
| PHYA_AT | PHYA | 14622_at | emb\|CAA35221.1\|(X17341) phyA photoreceptor [*Arabidopsis thaliana*] |
| RAN1_S_AT | RAN1 | 14641_s_at | gb\|AAD29109.1\|AF082565_1 (AF082565) ATP dependent copper transporter [*Arabidopsis thaliana*] |
| RD19A_S_AT | RD19A | 14644_s_at | emb\|CAB38829.1\|(AL035679) drought-inducible cysteine proteinase RD19A precursor |
| S69727.2_AT | S69727.2 | 16503_at | gb\|AAB20558.1\|(S69727) light-regulated glutamine synthetase isoenzyme [*Arabidopsis thaliana*, Peptide, 430 aa] |
| THIOLPROTEASE1_S_AT | THIOLPROTEASE1 | 14658_s_at | emb\|CAB38829.1\|(AL035679) drought-inducible cysteine proteinase RD19A precursor [*Arabidopsis thaliana*] |
| THIOLPROTEASE3_S_AT | THIOLPROTEASE3 | 14659_s_at | emb\|CAB38829.1\|(AL035679) drought-inducible cysteine proteinase RD19A precursor |
| TONOL_F_AT | TONOL | 14662_f_at | emb\|CAA38633.1\|(X54854) possible membrane channel protein [*Arabidopsis thaliana*] |
| U11256.2_AT | U11256.2 | 16035_at | gb\|AAA82212.1\|(U11256) metallothionein [*Arabidopsis thaliana*] |
| U15108.2_S_AT | U15108.2 | 16010_s_at | gb\|AAA50250.1\|(U15108) metallothionein-like protein [*Arabidopsis thaliana*] |
| U20347.2_S_AT | U20347.2 | 18651_s_at | gb\|AAA91976.1\|(U20347) mRNA corresponding to this gene accumulates in response to |
| U21214_S_AT | U21214 | 18687_s_at | gb\|AAA86507.1\|(U21214) pyruvate dehydrogenase E1 alpha subunit [*Arabidopsis thaliana*] |
| U33014.2_S_AT | U33014.2 | 15955_s_at | gb\|AAB53929.1\|(U33014) polyubiquitin [*Arabidopsis thaliana*] |
| U35640.2_S_AT | U35640.2 | 16032_s_at | gb\|AAC49351.1\|(U35640) thioredoxin h [*Arabidopsis thaliana*] |
| U35826.2_S_AT | U35826.2 | 19654_s_at | gb\|AAC49353.1\|(U35826) thioredoxin h [*Arabidopsis thaliana*] |
| U41998.4_AT | U41998.4 | 16476_at | gb\|AAB37098.1\|(U41998) actin 2 [*Arabidopsis thaliana*] |
| U43224_S_AT | U43224 | 12842_s_at | No hits found less than or equal to 1e-15. |
| U63815.18_S_AT | U63815.18 | 16429_s_at | gb\|AAB07880.1\|(U63815) ascorbate peroxidase [*Arabidopsis thaliana*] |
| U64912.1_S_AT | U64912.1 | 18989_s_at | gb\|AAB86892.1\|(AF032883) AtJ3 [*Arabidopsis thaliana*] |
| U65471_AT | U65471 | 18692_at | No hits found less than or equal to 1e-15. |
| U84969_3_F_AT | U84969 | 12833_f_at | gb\|AAB95252.1\|(U84969) ubiquitin [*Arabidopsis thaliana*] |
| U95973.108_AT | U95973.108 | 18639_at | gb\|AAB65482.1\|(U95973) endomembrane protein EMP70 precursor isolog [*Arabidopsis thaliana*] |
| WT108A_RC_AT | WT108A | 14690_at | No hits found less than or equal to 1e-15. |

TABLE 4-continued

Constitutively expressed *Arabidopsis* sequences and their corresponding genes.

| Gene ID | Accession # on chip | Affy # | Description |
| --- | --- | --- | --- |
| WT755_S_AT | WT755 | 14701_s_at | emb\|CAA52237.1\|(X74140) RCI14A [*Arabidopsis thaliana*] |
| WT758_AT | WT758 | 14703_at | gb\|AAD46040.1\|AC007519_25 (AC007519) ESTs gb\|H36253 and gb\|AA04251 come from this gene. [*Arabidopsis thaliana*] |
| X15550_S_AT | X15550 | 12843_s_at | gb\|AAD26488.1\|AC007195_2 (AC007195) unknown protein [*Arabidopsis thaliana*] |
| X16432.2_S_AT | X16432.2 | 15992_s_at | emb\|CAA34456.1\|(X16432) elongation factor 1-alpha [*Arabidopsis thaliana*] |
| X52256.2_AT | X52256.2 | 16443_at | emb\|CAB45802.2\|(AL080253) translation elongation factor EF-Tu precursor, chloroplast [*Arabidopsis thaliana*] |
| X65052_AT | X65052 | 16026_at | emb\|CAA46188.1\|(X65052) eukaryotic translation initiation factor 4A-1 [*Arabidopsis thaliana*] |
| X65549.1_AT | X65549.1 | 15963_at | emb\|CAA46518.1\|(X65549) adenylate translocator [*Arabidopsis thaliana*] |
| X68150.1_AT | X68150.1 | 16451_at | emb\|CAA48253.1\|(X68150) ketol-acid reductoisomerase [*Arabidopsis thaliana*] |
| X69294.2_S_AT | X69294.2 | 16030_s_at | emb\|CAA49155.1\|(X69294) transmembrane protein TMP-B [*Arabidopsis thaliana*] |
| X74604.2_S_AT | X74604.2 | 15953_s_at | emb\|CAA52684.1\|(X74604) heat shock protein 70 cognate [*Arabidopsis thaliana*] |
| X74733.2_AT | X74733.2 | 16463_at | emb\|CAA52751.1\|(X74733) elongation factor-1 beta A1 [*Arabidopsis thaliana*] |
| X75162.2_AT | X75162.2 | 16997_at | emb\|CAA53005.1\|(X75162) BBC1 protein [*Arabidopsis thaliana*] |
| X75881.2_AT | X75881.2 | 16446_at | emb\|CAA53475.1\|(X75881) plasma membrane intrinsic protein 1a [*Arabidopsis thaliana*] |
| X75883.2_AT | X75883.2 | 15989_at | emb\|CAB67649.1\|(AL132966) plasma membrane intrinsic protein 2a [*Arabidopsis thaliana*] |
| X78584.2_AT | X78584.2 | 16456_at | emb\|CAA55321.1\|(X78584) Di19 [*Arabidopsis thaliana*] |
| X81697.2_S_AT | X81697.2 | 16918_s_at | emb\|CAA57343.1\|(X81697) cysteine synthase [*Arabidopsis thaliana*] |
| X82002.1_AT | X82002.1 | 20261_at | emb\|CAA57528.1\|(X82002) protein phosphatase 2A 65 kDa regulatory subunit [*Arabidopsis thaliana*] |
| X84078_AT | X84078 | 18710_at | emb\|CAA58887.1\|(X84078) NADH dehydrogenase [*Arabidopsis thaliana*] |
| X84315.8_AT | X84315.8 | 18659_at | No hits found less than or equal to 1e−15. |
| X84318_AT | X84318 | 18711_at | emb\|CAA59061.1\|(X84318) NADH dehydrogenase [*Arabidopsis thaliana*] |
| X86962.3_AT | X86962.3 | 19917_at | emb\|CAA60525.1\|(X86962) protein kinase catalytic domain (fragment) [*Arabidopsis thaliana*] |
| X91398.2_AT | X91398.2 | 16988_at | emb\|CAA62744.1\|(X91398) transcription factor L2 [*Arabidopsis thaliana*] |
| X91958.1_AT | X91958.1 | 16469_at | emb\|CAA63024.1\|(X91958) 60S ribosomal protein L9 [*Arabidopsis thaliana*] |
| X91959.1_AT | X91959.1 | 15890_at | gb\|AAF04877.1\|AC010796_13 (AC010796) 60S ribosomal protein L27A [*Arabidopsis thaliana*] |
| X92510.2_S_AT | X92510.2 | 19706_s_at | emb\|CAA63266.1\|(X92510) allene oxide synthase [*Arabidopsis thaliana*] |
| X94626.1_AT | X94626.1 | 16508_at | emb\|CAA64329.1\|(X94626) AATP2 [*Arabidopsis thaliana*] |
| X99609.2_S_AT | X99609.2 | 17430_s_at | emb\|CAA67923.1\|(X99609) ubiquitin-like protein [*Arabidopsis thaliana*] |

TABLE 4-continued

Constitutively expressed *Arabidopsis* sequences and their corresponding genes.

| Gene ID | Accession # on chip | Affy # | Description |
|---|---|---|---|
| Y07765.7_S_AT | Y07765.7 | 16437_s_at | No hits found less than or equal to 1e−15. |
| Y09482.2_I_AT | Y09482.2 | 16036_i_at | emb\|CAA70691.1\|(Y09482) HMG1 [*Arabidopsis thaliana*] |
| Y10157.3_S_AT | Y10157.3 | 19833_s_at | emb\|CAA71239.1\|(Y10157) sulfite reductase [*Arabidopsis thaliana*] |
| Y10863.1_I_AT | Y10863.1 | 19919_i_at | emb\|CAA71879.1\|(Y10986) hypothetical protein 194 [*Arabidopsis thaliana*] |
| Y12295.2_S_AT | Y12295.2 | 16033_s_at | emb\|CAA72973.1\|(Y12295) glutathione transferase [*Arabidopsis thaliana*] |
| Y14052.2_AT | Y14052.2 | 16506_at | emb\|CAA74381.1\|(Y14052) ribosomal protein S6 [*Arabidopsis thaliana*] |
| Y17053.2_AT | Y17053.2 | 15960_at | emb\|CAA76606.1\|(Y17053) At-hsc70-3 [*Arabidopsis thaliana*] |
| Z12024_AT | Z12024 | 18731_at | emb\|CAA78059.1\|(Z12024) calmodulin [*Arabidopsis thaliana*] |
| Z14989.5_AT | Z14989.5 | 17414_at | emb\|CAA78713.1\|(Z14989) ubiquitin conjugating enzyme homolog [*Arabidopsis thaliana*] |
| Z15157.1_AT | Z15157.1 | 16982_at | emb\|CAA78856.1\|(Z15157) Wilm's tumor suppressor homologue [*Arabidopsis thaliana*] |
| Z28702.2_AT | Z28702.2 | 16984_at | emb\|CAA82273.1\|(Z28701) S18 ribosomal protein [*Arabidopsis thaliana*] |
| Z97335.5_S_AT | Z97335.5 | 16504_s_at | emb\|CAB10172.1\|(Z97335) hydroxymethyltransferase [*Arabidopsis thaliana*] |
| Z97336.1_AT | Z97336.1 | 16930_at | emb\|CAB10211.1\|(Z97336) ribosomal protein [*Arabidopsis thaliana*] |
| Z97337.298_S_AT | Z97337.298 | 16934_s_at | emb\|CAB10279.1\|(Z97337) ribosomal protein [*Arabidopsis thaliana*] |
| Z97340.298_S_AT | Z97340.298 | 15972_s_at | emb\|CAB10398.1\|(Z97340) cysteine proteinase like protein [*Arabidopsis thaliana*] |
| Z97341.130_AT | Z97341.130 | 18230_at | emb\|CAB10428.1\|(Z97341) symbiosis-related like protein [*Arabidopsis thaliana*] |
| Z97341.407_AT | Z97341.407 | 18614_at | emb\|CAB10447.1\|(Z97341) ribosomal protein [*Arabidopsis thaliana*] |
| Z97343.270_S_AT | Z97343.270 | 16926_s_at | emb\|CAB10520.1\|(Z97343) ribosomal protein [*Arabidopsis thaliana*] |
| Z99708.65_AT | Z99708.65 | 19139_at | emb\|CAB16820.1\|(Z99708) ubiquitin--protein ligase-like protein [*Arabidopsis thaliana*] |

Organ differential expressed genes were also analyzed. These genes were expressed at median level (average difference greater than 50) in certain organ at all developmental stages, e.g., compared to other organs, the expression level for these genes in the organ are 4-fold higher than others. By these criteria, genes differentially expressed in root (64) (see Table 5), leaf (94) (see Table 6), inflorescence stem (3), and flower (36) were identified, and functionally categorized.

TABLE 5

*Arabidopsis* sequences which are expressed in a root-specific manner and their corresponding genes.

| Accession # | Affy # | Description |
|---|---|---|
| A71588.1 | 14015_s_at | pir\|\|T10626 reticuline oxidase homolog F21C20.190 - *Arabidopsis thaliana* >gi\|5262224\|emb\|CAB45850.1\| (AL080254) reticuline oxidase-like protein [*Arabidopsis thaliana*] >gi\|7268880\|emb\|CAB79084.1\|(AL161553) reticuline oxidase-like protein [*Arabidopsis thaliana*] |
| A71596.1 | 14016_s_at | gb\|AAD25763.1\|AC007060_21 (AC007060) Strong similarity to F19I3.2 gi\|3033375 putative berberine bridge enzyme from *Arabidopsis thaliana* BAC gb\|AC004238. |

TABLE 5-continued

Arabidopsis sequences which are expressed in a root-specific manner and their corresponding genes.

| Accession # | Affy # | Description |
|---|---|---|
| A71597.1 | 12079_s_at | "gb|AAD25757.1|AC007060_15 (AC007060) Strong similarity to F19I3.2 gi|3033375 putative berberine bridge enzyme from Arabidopsis thaliana BAC gb|AC004238. ESTs gb|F19886, gb|Z30784 and gb|Z30785 come from this gene" |
| AB023448.2 | 12332_s_at | dbj|BAA82824.1|(AB023462) basic endochitinase [Arabidopsis thaliana] |
| AC001645.19 | 15965_at | gb|AAC08601.1|(AF054906) myrosinase-binding protein homolog [Arabidopsis thaliana] |
| AC001645.47 | 15996_at | gb|AAB63635.1|(AC001645) jasmonate inducible protein isolog [Arabidopsis thaliana] |
| AC001645.50 | 15981_at | gb|AAB63635.1|(AC001645) jasmonate inducible protein isolog [Arabidopsis thaliana] |
| AC002333.199 | 13552_at | gb|AAB64044.1|(AC002333) putative endochitinase [Arabidopsis thaliana] |
| AC002333.210 | 13154_s_at | sp|Q06209|CHI4_BRANA BASIC ENDOCHITINASE CHB4 PRECURSOR >gi|7435353|pir||S25311 chitinase (EC 3.2.1.14) precursor - rape >gi|17799|emb|CAA43708.1| (X61488) chitinase [Brassica napus] |
| AC002391.150 | 17842_i_at | pir||T04731 cytochrome P450 homolog F6G17.20 - Arabidopsis thaliana >gi|4468803|emb|CAB38204.1| (AL035601) cytochrome P450-like protein [Arabidopsis thaliana] >gi|7270719|emb|CAB80402.1|(AL161591) cytochrome P450-like protein [Arabidopsis thaliana] |
| AC003673.201 | 16481_s_at | pir||T01626 peroxidase (EC 1.11.1.7) ATP22a - Arabidopsis thaliana >gi|3004558|gb|AAC09031.1|(AC003673) peroxidase (ATP22a) [Arabidopsis thaliana] |
| AC004005.104 | 19390_at | pir||T00681 hypothetical protein F6E13.14 - Arabidopsis thaliana >gi|3212858|gb|AAC23409.1|(AC004005) unknown protein [Arabidopsis thaliana] |
| AC004521.114 | 19195_at | pir||T02393 hypothetical protein F4I1.19 - Arabidopsis thaliana >gi|3128201|gb|AAC16105.1|(AC004521) unknown protein [Arabidopsis thaliana] |
| AC004521.119 | 20608_s_at | pir||T02393 hypothetical protein F4I1.19 - Arabidopsis thaliana >gi|3128201|gb|AAC16105.1|(AC004521) unknown protein [Arabidopsis thaliana] |
| AC004683.79 | 16461_i_at | sp|P24102|PERE_ARATH BASIC PEROXIDASE E PRECURSOR >gi|81653|pir||JU0458 peroxidase (EC 1.11.1.7) E - Arabidopsis thaliana >gi|166807|gb|AAA32842.1|(M58381) peroxidase [Arabidopsis thaliana] |
| AC004684.165 | 17907_s_at | pir||T02541 hypothetical protein F13M22.25 - Arabidopsis thaliana >gi|3236257|gb|AAC23645.1|(AC004684) unknown protein [Arabidopsis thaliana] |
| AC005310.6 | 17697_at | pir||T02675 hypothetical protein F19D11.2 - Arabidopsis thaliana >gi|3510249|gb|AAC33493.1|(AC005310) unknown protein [Arabidopsis thaliana] |
| AC005560.136 | 16016_at | pir||G71401 probable major latex protein - Arabidopsis thaliana >gi|2244762|emb|CAB10185.1|(Z97335) major latex protein like [Arabidopsis thaliana] >gi|7268111|emb|CAB78448.1|(AL161538) major latex protein like [Arabidopsis thaliana] |
| AC005560.147 | 12758_at | pir||G71401 probable major latex protein - Arabidopsis thaliana >gi|2244762|emb|CAB10185.1|(Z97335) major latex protein like [Arabidopsis thaliana] >gi|7268111|emb|CAB78448.1|(AL161538) major latex protein like [Arabidopsis thaliana] |
| AC005967.50 | 17864_at | emb|CAA18195.1|(AL022198) putative protein [Arabidopsis thaliana] >gi|7270000|emb|CAB79816.1|(AL161578) putative protein [Arabidopsis thaliana] |
| AC006216.22 | 14050_at | gb|AAD12680.1|(AC006216) Similar to gi|3413714 T19L18.21 putative myrosinase-binding protein from Arabidopsis thaliana BAC gb|AC004747 |
| AC006216.26 | 18571_at | "gb|AAD12679.1|(AC006216) Similar to gi|3413714 T19L18.21 putative myrosinase-binding protein from Arabidopsis thaliana BAC gb|AC004747. ESTs gb|T44298, gb|T42447, gb|R64761 and gb|I100206 come from this gene" |
| AC006577.16 | 12778_r_at | "gb|AAD25772.1|AC006577_8 (AC006577) Belongs to the PF|00657 Lipase/Acylhydrolase with GDSL-motif family. ESTs gb|T44453, gb|T04815, gb|T45993, gb|R30138, gb|AI099570 and gb|T22281 come from this gene. [Arabidopsis thaliana]" |
| AC006587.164 | 15859_at | gb|AAD21491.1|(AC006587) unknown protein [Arabidopsis thaliana] |

TABLE 5-continued

*Arabidopsis* sequences which are expressed in a root-specific manner and their corresponding genes.

| Accession # | Affy # | Description |
|---|---|---|
| AC007060.34 | 19840_s_at | gb\|AAD25758.1\|AC007060_16 (AC007060) Strong similarity to F19I3.2 gi\|3033375 putative berberine bridge enzyme from *Arabidopsis thaliana* BAC gb\|AC004238 |
| AC007135.23 | 20176_at | gb\|AAD41993.1\|AC006233_16 (AC006233) unknown protein [*Arabidopsis thaliana*] |
| AC007584.48 | 20194_at | gb\|AAF20251.1\|AC015450_12 (AC015450) unknown protein [*Arabidopsis thaliana*] |
| ACHI | 12852_s_at | dbj\|BAA21873.1\|(AB006068) acidic endochitinase [*Arabidopsis thaliana*] |
| AF098630.3 | 19118_s_at | gb\|AAD12259.1\|(AF098631) putative cell wall-plasma membrane disconnecting CLCT protein [*Arabidopsis thaliana*] |
| AF128395.12 | 20395_at | "sp\|P33154\|PR1_ARATH PATHOGENESIS-RELATED PROTEIN 1 PRECURSOR (PR-1) >gi\|322557\|pir\|\|JQ1693 pathogenesis-related protein 1 precursor, 17.6K - *Arabidopsis thaliana* >gi\|166861\|gb\|AAA32863.1\|(M90508) PR-1-like protein [*Arabidopsis thaliana*] >gi\|3810599\|gb\|AAC69381.1\| (AC005398) pathogenesis-related PR-1-like protein [*Arabidopsis thaliana*]" |
| AJ133036.5 | 15969_s_at | sp\|P24101\|PERC_ARATH NEUTRAL PEROXIDASE C PRECURSOR >gi\|81652\|pir\|\|JU0457 peroxidase (EC 1.11.1.7) C - *Arabidopsis thaliana* >gi\|166827\|gb\|AAA32849.1\| (M58380) peroxidase [*Arabidopsis thaliana*] >gi\|6522555\|emb\|CAB61999.1\|(AL132967) peroxidase [*Arabidopsis thaliana*] >gi\|742247\|prf\|\|2009327A peroxidase [*Arabidopsis thaliana*] |
| AL024486.185 | 16299_at | sp\|P42620\|YQJG_ECOLI HYPOTHETICAL 37.4 KD PROTEIN IN EXUR-TDCC INTERGENIC REGION (O328) >gi\|7465984\|pir\|\|C65099 hypothetical 37.4 kD protein in exuR-tdcC intergenic region - *Escherichia coli* (strain K-12) >gi\|606043\|gb\|AAA57906.1\|(U18997) ORF_o328 [*Escherichia coli*] >gi\|1789489\|gb\|AAC76137.1\|(AE000392) putative transferase [*Escherichia coli*] |
| AL035538.245 | 16514_at | pir\|\|T05635 hypothetical protein F20D10.200 - *Arabidopsis thaliana* >gi\|4467114\|emb\|CAB37548.1\|(AL035538) putative protein [*Arabidopsis thaliana*] >gi\|7270791\|emb\|CAB80473.1\|(AL161592) putative protein [*Arabidopsis thaliana*] |
| AL049500.57 | 16914_s_at | sp\|P50700\|OSL3_ARATH OSMOTIN-LIKE PROTEIN OSM34 PRECURSOR >gi\|1362001\|pir\|\|S57524 osmotin precursor - *Arabidopsis thaliana* >gi\|887390\|emb\|CAA61411.1\| (X89008) osmotin [*Arabidopsis thaliana*] |
| AL049638.193 | 20029_at | pir\|\|T06615 hypothetical protein F16J13.150 - *Arabidopsis thaliana* >gi\|4586113\|emb\|CAB40949.1\|(AL049638) putative DNA-binding protein [*Arabidopsis thaliana*] >gi\|7267909\|emb\|CAB78251.1\|(AL161533) putative DNA-binding protein [*Arabidopsis thaliana*] |
| AL049730.104 | 18983_s_at | "pir\|\|S42552 proline-rich protein - rape >gi\|545029\|gb\|AAC60566.1\|(S68113) proline-rich SAC51 [*Brassica napus* = oilseed rape, pods, Peptide, 147 aa]" |
| AL080253.32 | 19415_at | gb\|AAF08575.1\|AC011623_8 (AC011623) unknown protein [*Arabidopsis thaliana*] |
| AL080282.74 | 18597_at | pir\|\|T10624 reticuline oxidase homolog F21C20.170 - *Arabidopsis thaliana* >gi\|5262222\|emb\|CAB45848.1\| (AL080254) reticuline oxidase-like protein [*Arabidopsis thaliana*] >gi\|7268878\|emb\|CAB79082.1\|(AL161553) reticuline oxidase-like protein [*Arabidopsis thaliana*] |
| ATAJ2596 | 16085_s_at | emb\|CAB16787.1\|(Z99707) patatin-like protein [*Arabidopsis thaliana*] >gi\|7270656\|emb\|CAB80373.1\|(AL161590) patatin-like protein [*Arabidopsis thaliana*] |
| ATHORF | 16649_s_at | gb\|AAF16563.1\|AC012563_16 (AC012563) putative S-adenosyl-L-methionine:trans-caffeoyl-Coenzyme A 3-O-methyltransferase [*Arabidopsis thaliana*] |
| ATPIN2 | 12932_s_at | gb\|AAD04377.1\|(AF089085) putative auxin efflux carrier protein; AtPIN1 [*Arabidopsis thaliana*] |
| ATU10034 | 15120_s_at | sp\|Q42521\|DCE1_ARATH GLUTAMATE DECARBOXYLASE 1 (GAD 1) >gi\|497979\|gb\|AAA93132.1\|(U10034) glutamate decarboxylase [*Arabidopsis thaliana*] |
| ATU57320 | 15137_s_at | gb\|AAB47973.1\|(U57320) blue copper-binding protein II [*Arabidopsis thaliana*] |
| ATU62330 | 15623_f_at | dbj\|BAA24282.1\|(AB000094) inorganic phosphate transporter [*Arabidopsis thaliana*] |
| BCHI | 13211_s_at | dbj\|BAA82824.1\|(AB023462) basic endochitinase [*Arabidopsis thaliana*] |

TABLE 5-continued

Arabidopsis sequences which are expressed in a root-specific manner and their corresponding genes.

| Accession # | Affy # | Description |
|---|---|---|
| CAFFEROYLCOA-METHYLTRANS | 13215_s_at | gb|AAA62426.1|(L40031) S-adenosyl-L-methionine:trans-caffeoyl-Coenzyme A 3-O-methyltransferase [Arabidopsis thaliana] |
| NOVARTIS51 | 14170_at | gb|AAF29406.1|AC022354_5 (AC022354) unknown protein [Arabidopsis thaliana] |
| U72155.2 | 15954_at | gb|AAB64244.1|(U72155) beta-glucosidase [Arabidopsis thaliana] |
| U81294.2 | 20422_g_at | gb|AAD00509.1|(U81294) germin-like protein [Arabidopsis thaliana] |
| X67421.3 | 16489_at | pir||S53012 root-specific protein RCc3 - rice >gi|786132|gb|AAA65513.1|(L27208) RCc3 [Oryza sativa] |
| X74514.2 | 20239_g_at | dbj|BAA89048.1|(AB029310) beta-fructofuranosidase [Arabidopsis thaliana] |
| X78586.2 | 16048_at | pir||S51480 drought-induced protein Dr4 - Arabidopsis thaliana >gi|469114|emb|CAA55323.1|(X78586) Dr4 [Arabidopsis thaliana] |
| X98319.2 | 16971_s_at | emb|CAA66963.1|(X98319) peroxidase [Arabidopsis thaliana] >gi|1429217|emb|CAA67311.1|(X98775) peroxidase ATP12a [Arabidopsis thaliana] >gi|6714469|gb|AAF26155.1|AC008261_12 (AC008261) putative peroxidase [Arabidopsis thaliana] |
| X98320.2 | 18312_s_at | gb|AAF63027.1|AF244924_1 (AF244924) peroxidase prx15 precursor [Spinacia oleracea] |
| X98321.2 | 19595_s_at | gb|AAB71452.1|(AC000098) Strong similarity to Arabidopsis peroxidase ATPEROX7A (gb|X98321). [Arabidopsis thaliana] >gi|2738254|gb|AAB94661.1|(U97684) peroxidase precursor [Arabidopsis thaliana] |
| X98322.2 | 17942_s_at | gb|AAF03466.1|AC009327_5 (AC009327) putative peroxidase [Arabidopsis thaliana] |
| X98808.1 | 15985_at | emb|CAA67340.1|(X98808) peroxidase ATP3a [Arabidopsis thaliana] |
| X98855.2 | 16028_at | pir||T01626 peroxidase (EC 1.11.1.7) ATP22a - Arabidopsis thaliana >gi|3004558|gb|AAC09031.1|(AC003673) peroxidase (ATP22a) [Arabidopsis thaliana] |
| Y11788.1 | 18946_at | emb|CAA72484.1|(Y11788) peroxidase ATP24a [Arabidopsis thaliana] |
| Z97338.321 | 16045_s_at | pir||E71418 hypothetical protein - Arabidopsis thaliana >gi|2244897|emb|CAB10319.1|(Z97338) HSR201 like protein [Arabidopsis thaliana] >gi|7268287|emb|CAB78582.1|(AL161541) HSR201 like protein [Arabidopsis thaliana] |
| Z97340.345 | 17485_s_at | "sp|P52407|E13B_HEVBR GLUCAN ENDO-1,3-BETA-GLUCOSIDASE, BASIC VACUOLAR ISOFORM PRECURSOR ((1->3)-BETA-GLUCAN ENDOHYDROLASE) ((1->3)-BETA-GLUCANASE) (BETA-1,3-ENDOGLUCANASE) >gi|2129912|pir||S65077 1,3-beta-glucanase (EC 3.2.1.—) precursor - Para rubber tree >gi|1184668|gb|AAA87456.1| (U22147) beta-1,3-glucanase [Hevea brasiliensis]" |
| Z97344.151 | 19886_at | gb|AAC61811.1|(AC004667) putative AT-hook DNA-binding protein [Arabidopsis thaliana] |
| Z99707.288 | 18326_s_at | emb|CAB16788.1|(Z99707) patatin-like protein [Arabidopsis thaliana] >gi|7270655|emb|CAB80372.1|(AL161590) patatin-like protein [Arabidopsis thaliana] |

TABLE 6

Arabidopsis sequences which are expressed in a leaf-specific manner and their corresponding genes.

| Affy ID | Accession | function | Description |
|---|---|---|---|
| 11994_at | AC004218.86_AT | novel | gb|AAC27838.1|(AC004218) unknown protein [Arabidopsis thaliana] |
| 12086_s_at | AC002409.88_S_AT | novel | gb|AAB86456.1|(AC002409) unknown protein [Arabidopsis thaliana] |
| 12095_at | AC006223.95_AT | novel | gb|AAD15394.1|(AC006223) hypothetical protein [Arabidopsis thaliana] |

TABLE 6-continued

*Arabidopsis* sequences which are expressed in a leaf-specific manner and their corresponding genes.

| Affy ID | Accession | function | Description |
| --- | --- | --- | --- |
| 12105_at | AF000657.30_AT | novel | gb|AAB72170.1|(AF000657) hypothetical protein [*Arabidopsis thaliana*] |
| 12115_at | AL033545.26_AT | metabolism | emb|CAA22152.1|(AL033545) extensin-like protein [*Arabidopsis thaliana*] |
| 12135_at | AC007230.29_AT | novel | gb|AAD26875.1|AC007230_9 (AC007230) ESTs gb|H76289 and gb|H76537 come from this gene. [*Arabidopsis thaliana*] |
| 12270_at | AL030978.79_AT | kinase | emb|CAA19724.1|(AL030978) putative receptor protein kinase [*Arabidopsis thaliana*] |
| 12299_at | AL022347.265_AT | kinase | emb|CAA18476.1|(AL022347) serine/threonine kinase-like protein [*Arabidopsis thaliana*] |
| 12305_i_at | AL022347.219_I_AT | novel | emb|CAA18473.1|(AL022347) putative protein [*Arabidopsis thaliana*] |
| 12392_at | AC002391.102_AT | transcription | gb|AAB87103.1|(AC002391) putative MYB family transcription factor [*Arabidopsis thaliana*] |
| 12788_at | AC002311.20_AT | defense | "gb|AAC00607.1|(AC002311) similar to ripening-induced protein, gp|AJ001449|2465015 and major#latex protein, gp|X91961|1107495 [*Arabidopsis thaliana*]" |
| 13243_r_at | ELI32_R_AT | metabolism | emb|CAB37539.1|(AL035538) cinnamyl-alcohol dehydrogenase ELI3-2 [*Arabidopsis* |
| 13352_at | AL030978.126_AT | novel | emb|CAA19730.1|(AL030978) putative protein [*Arabidopsis thaliana*] |
| 13620_at | AL035605.41_AT | metabolism | emb|CAB38295.1|(AL035605) formamidase-like protein [*Arabidopsis thaliana*] |
| 13719_at | NOVARTIS106_AT | novel | No hits found less than or equal to 1e−15. |
| 13812_s_at | AC005275.104_S_AT | hormone | gb|AAD14468.1|(AC005275) putative GH3-like protein [*Arabidopsis thaliana*] |
| 13972_s_at | Z97344.134_S_AT | transcription | emb|CAB10561.1|(Z97344) SUPERMAN like protein [*Arabidopsis thaliana*] |
| 14192_at | NOVARTIS66_AT | novel | gb|AAC34331.1|(AC004122) Unknown protein [*Arabidopsis thaliana*] |
| 14218_at | NOVARTIS87_AT | novel | No hits found less than or equal to 1e−15. |
| 14242_s_at | NRA_S_AT | metabolism | gb|AAF19225.1|AC007505_1 (AC007505) nitrate reductase [*Arabidopsis thaliana*] |
| 14248_at | PAD3_AT | metabolism | "gb|AAD31062.1|AC007357_11 (AC007357) Strong similarity to gb|X97864 cytochrome P450 from *Arabidopsis thaliana* and is a member of the PF|00067 Cytochrome P450 family. ESTs gb|N65665, gb|T14112, gb|T76255, gb|T20906 and gb|AI100027 come from this gene." |
| 14432_at | AL035440.502_AT | novel | emb|CAB36549.1|(AL035440) putative protein [*Arabidopsis thaliana*] |
| 14484_at | U73462.2_AT | metabolism | gb|AAC32523.1|(U73462) carbonic anhydrase [*Arabidopsis thaliana*] |
| 14533_i_at | AC007048.166_I_AT | novel | gb|AAC32523.1|(U73462) carbonic anhydrase [*Arabidopsis thaliana*] |
| 14600_at | AC007576.49_AT | novel | gb|AAD39297.1|AC007576_20 (AC007576) Unknown protein [*Arabidopsis thaliana*] |
| 14603_at | AL022347.282_AT | kinase | emb|CAA18477.1|(AL022347) serine/threonine kinase-like protein [*Arabidopsis thaliana*] |

TABLE 6-continued

*Arabidopsis* sequences which are expressed in a leaf-specific manner and their corresponding genes.

| Affy ID | Accession | function | Description |
|---|---|---|---|
| 14621_at | PDF1.2__AT | defense | gb|AAC31244.1|(AC004747) putative antifungal protein [*Arabidopsis thaliana*] |
| 14635_s_at | PR.1_S_AT | defense | gb|AAC69381.1|(AC005398) pathogenesis-related PR-1-like protein [*Arabidopsis thaliana*] |
| 14682_i_at | WT1012A_RC_I_AT | novel | No hits found. |
| 14709_at | WT788_AT | novel | No hits found less than or equal to 1e−15. |
| 14803_at | AC006550.33__AT | metabolism | gb|AAD25807.1|AC006550_15 (AC006550) Strong similarity to gb|Z49699 glutaredoxin from *Ricinus communis*. [*Arabidopsis thaliana*] |
| 14808_i_at | AC007230.21_I_AT | kinase | gb|AAD26873.1|AC007230_7 (AC007230) Contains PF|00069 Eukaryotic protein kinase domain. [*Arabidopsis thaliana*] |
| 14862_at | AC005770.205__AT | transcription | gb|AAC79620.1|(AC005770) putative RING zinc finger protein [*Arabidopsis thaliana*] |
| 15185_s_at | AB024283_S_AT | metabolism | dbj|BAA78561.1|(AB024283) cysteine synthase [*Arabidopsis thaliana*] |
| 15271_at | AC004077.141__AT | novel | gb|AAC26689.1|(AC004077) unknown protein [*Arabidopsis thaliana*] |
| 15422_at | AF069441.29__AT | novel | gb|AAD36948.1|AF069441_8 (AF069441) hypothetical protein [*Arabidopsis thaliana*] |
| 15467_at | AC000375.34__AT | novel | gb|AAB60770.1|(AC000375) EST gb|H37044 comes from this gene. [*Arabidopsis thaliana*] |
| 15552_at | AL096859.162__AT | novel | emb|CAB51187.1|(AL096859) putative protein [*Arabidopsis thaliana*] |
| 15613_s_at | ATHHOMEOA_S_AT | metabolism | emb|CAA79670.1|(Z19602) HAT4 [*Arabidopsis thaliana*] |
| 15837_at | AC005496.175__AT | metabolism | gb|AAC35232.1|(AC005496) putative thiamin biosynthesis protein [*Arabidopsis thaliana*] |
| 16137_s_at | AF149053_S_AT | metabolism | gb|AAD38033.1|AF149053_1 (AF149053) phytochrome kinase substrate 1 [*Arabidopsis thaliana*] |
| 16172_s_at | D78603_S_AT | metabolism | dbj|BAA28535.1|(D78603) cytochrome P450 monooxygenase [*Arabidopsis thaliana*] |
| 16322_at | AL096860.203__AT | novel | emb|CAB51215.1|(AL096860) putative protein [*Arabidopsis thaliana*] |
| 16323_at | AC005957.35__AT | defense | gb|AAD03365.1|(AC005957) putative disease resistance protein [*Arabidopsis thaliana*] |
| 16331_at | AC005957.23__AT | defense | gb|AAD03361.1|(AC005957) putative disease resistance protein [*Arabidopsis thaliana*] |
| 16365_at | AC003974.136__AT | defense | gb|AAC04495.1|(AC003974) putative disease resistance protein [*Arabidopsis thaliana*] |
| 16547_s_at | AF053941_S_AT | metabolism | gb|AAC27293.2|(AF053941) non phototropic hypocotyl 1-like [*Arabidopsis thaliana*] |
| 16583_s_at | ATHZFPH_S_AT | transcription | gb|AAA87304.1|(L39651) zinc finger protein [*Arabidopsis thaliana*] |
| 16687_s_at | AC004044.64_S_AT | novel | gb|AAC79114.1|(AF069442) hypothetical protein [*Arabidopsis thaliana*] |
| 16845_at | AC006232.87__AT | metabolism | gb|AAD15594.1|(AC006232) putative cysteine proteinase [*Arabidopsis thaliana*] |
| 16856_i_at | AC004681.86_I_AT | metabolism | gb|AAC25936.1|(AC004681) putative cellulose synthase [*Arabidopsis thaliana*] |
| 17019_s_at | ATU28422_S_AT | transcription | gb|AAC33507.1|(AC005310) MYB-related transcription factor (CCA1) [*Arabidopsis thaliana*] |

TABLE 6-continued

*Arabidopsis* sequences which are expressed in a leaf-specific manner and their corresponding genes.

| Affy ID | Accession | function | Description |
|---|---|---|---|
| 17128_s_at | ATHRPRP1A_S_AT | defense | gb\|AAC69381.1\|(AC005398) pathogenesis-related PR-1-like protein [*Arabidopsis* |
| 17231_at | AC004411.170_AT | novel | gb\|AAC34226.1\|(AC004411) hypothetical protein [*Arabidopsis thaliana*] |
| 17331_at | AF069298.23_AT | kinase | "gb\|AAC19274.1\|(AF069298) contains similarity to a protein kinase domain (Pfam: pkinase.hmm, score: 165.48), to legume lectins beta domain (Pfam: lectin_legB.hmm, score: 125.64) and legume lectins alpha domain (Pfam: lectin_legA.hmm, score: 16.72) [Arabi |
| 17361_s_at | AF096373.28_S_AT | metabolism | emb\|CAB39764.1\|(AL049487) sucrose-phosphate synthase-like protein [*Arabidopsis thaliana*] |
| 17411_s_at | X98926.1_S_AT | defense | emb\|CAA67426.1\|(X98926) thylakoid-bound ascorbate peroxidase [*Arabidopsis thaliana*] |
| 17815_s_at | Z97342.284_S_AT | defense | emb\|CAB46050.1\|(Z97342) disease resistance RPP5 like protein (fragment) [*Arabidopsis thaliana*] |
| 17835_at | AF096370.14_AT | RNA binding protein | gb\|AAC62779.1\|(AF096370) contains similarity to *Arabidopsis thaliana* reverse transcriptase-like proteins |
| 17861_s_at | AC005560.16_S_AT | transport | gb\|AAC67319.1\|(AC005560) putative auxin transport protein [*Arabidopsis thaliana*] |
| 17936_s_at | Z97342.384_S_AT | metabolism | emb\|CAB46051.1\|(Z97342) putative beta-amylase [*Arabidopsis thaliana*] |
| 18115_at | AC005388.43_AT | kinase | gb\|AAC64891.1\|(AC005388) Similar to T11J7.13 gi\|2880051 putative protein kinase from *Arabidopsis thaliana* BAC gb\|AC002340. |
| 18296_at | AC002510.60_AT | kinase | gb\|AAB84338.1\|(AC002510) putative Ca2+-ATPase [*Arabidopsis thaliana*] |
| 18301_s_at | AL022223.48_S_AT | metabolism | emb\|CAA18218.1\|(AL022223) fructose-bisphosphate aldolase [*Arabidopsis thaliana*] |
| 18469_at | AC006341.12_AT | kinase | gb\|AAD34678.1\|AC006341_6 (AC006341) Similar to gb\|AJ012423 wall-associated kinase 2 from *Arabidopsis thaliana*. |
| 18588_at | AL022604.205_AT | novel | emb\|CAA18744.1\|(AL022604) putative protein [*Arabidopsis thaliana*] |
| 18670_g_at | AJ250341_G_AT | metabolism | emb\|CAB58423.1\|(AJ250341) beta-amylase enzyme [*Arabidopsis thaliana*] |
| 18778_at | Z97338.384_AT | novel | emb\|CAB10322.1\|(Z97338) hypothetical protein [*Arabidopsis thaliana*] |
| 18811_at | AC002396.32_AT | novel | gb\|AAC00583.1\|(AC002396) Hypothetical protein [*Arabidopsis thaliana*] |
| 18835_at | AC007260.34_AT | novel | gb\|AAD30584.1\|AC007260_15 (AC007260) lcl\|prt_seq No definition line found [*Arabidopsis thaliana*] |
| 18844_at | AC005315.131_AT | transport | gb\|AAC33239.1\|(AC005315) putative ligand-gated ion channel protein [*Arabidopsis thaliana*] |
| 18866_at | AC005917.178_AT | transposable element | gb\|AAD10163.1\|(AC005917) putative Ta11-like non-LTR retroelement protein [*Arabidopsis thaliana*] |
| 19034_at | AL021768.117_AT | defense | emb\|CAA16930.1\|(AL021768) TMV resistance protein N-like [*Arabidopsis thaliana*] |
| 19465_at | AL021768.96_AT | defense | emb\|CAA16929.1\|(AL021768) resistance protein RPP5-like [*Arabidopsis thaliana*] |

TABLE 6-continued

*Arabidopsis* sequences which are expressed in a leaf-specific manner and their corresponding genes.

| Affy ID | Accession | function | Description |
|---|---|---|---|
| 19581_at | AC006526.102_AT | transport | gb\|AAD23055.1\|AC006526_14 (AC006526) putative cyclic nucleotide-regulated ion channel protein [*Arabidopsis thaliana*] |
| 19704_i_at | AJ005927.2_I_AT | metabolism | emb\|CAA06769.1\|(AJ005927) squalene epoxidase homologue [*Arabidopsis thaliana*] |
| 19718_at | AC000098.16_AT | transport | gb\|AAB71447.1\|(AC000098) Similar to Arabidopsis Fe(II) transport protein (gb\|U27590). [*Arabidopsis thaliana*] |
| 19720_at | AC003979.28_AT | hormone | gb\|AAC25517.1\|(AC003979) Contains similarity to gibberellin-regulated protein 2 precursor (GAST1) homolog gb\|U11765 from *A. thaliana*. [*Arabidopsis thaliana*] |
| 19774_at | AC007167.248_AT | transport | gb\|AAD30549.1\|AF136580_1 (AF136580) iron-regulated transporter 2 [*Lycopersicon esculentum*] |
| 19834_at | AC006264.14_AT | hormone | gb\|AAD29795.1\|AC006264_3 (AC006264) putative auxin-regulated protein [*Arabidopsis thaliana*] |
| 19889_at | AC003033.139_AT | novel | gb\|AAB91986.1\|(AC003033) unknown protein [*Arabidopsis thaliana*] |
| 19901_at | AC003033.129_AT | novel | gb\|AAB91985.1\|(AC003033) unknown protein [*Arabidopsis thaliana*] |
| 19992_at | AC007138.58_AT | novel | gb\|AAD22657.1\|AC007138_21 (AC007138) predicted protein of unknown function [*Arabidopsis thaliana*] |
| 20062_at | AC005896.23_AT | novel | gb\|AAC98045.1\|(AC005896) unknown protein [*Arabidopsis thaliana*] |
| 20063_at | AC006284.5_AT | metabolism | gb\|AAD17422.1\|(AC006284) putative esterase [*Arabidopsis thaliana*] |
| 20232_s_at | AL022347.12_S_AT | kinase | emb\|CAA18460.1\|(AL022347) protein kinase-like protein [*Arabidopsis thaliana*] |
| 20356_at | AC004561.74_AT | metabolism | gb\|AAC95191.1\|(AC004561) putative glutathione S-transferase [*Arabidopsis thaliana*] |
| 20429_s_at | Z97336.167_S_AT | novel | emb\|CAB10219.1\|(Z97336) hypothetical protei [*Arabidopsis thaliana*] |
| 20525_at | AC007169.89_AT | transcription | gb\|AAD26481.1\|AC007169_13 (AC007169) putative CONSTANS-like B-box zinc finger protein [*Arabidopsis thaliana*] |
| 20537_at | AL049608.65_AT | metabolism | emb\|CAB40769.1\|(AL049608) extensin-like protein [*Arabidopsis thaliana*] |
| 20544_at | AL035679.68_AT | transcription | emb\|CAB38816.1\|(AL035679) putative zinc finger protein [*Arabidopsis thaliana*] |
| 20705_at | AL049607.66_AT | metabolism | emb\|CAB40757.1\|(AL049607) glutathione peroxidase-like protein [*Arabidopsis thaliana*] |

To examine the organ-specificity of the differential expression, the expression level of differentially expressed genes were plotted against represented samples. The root differential expressed genes are expressed almost exclusively in root and young whole seedlings. There were 51 genes that were expressed only in root. Twenty-three percent of these genes had no known function while peroxidases and defense genes represented 51% of the genes.

Similar experiments were conducted for root at least 3 hours after exposure to stress, e.g., salt, mannitol or cold (Tables 7-8). Twenty-five root-specific promoters were downregulated and 8 were upregulated in response to salt stress, 21 were down-regulated and 17 were upregulated in response to mannitol, and 22 were downregulated and 7 were upregulated in response to cold. Ten promoters did not respond to any of the stresses.

Expression results from an acute (3 hour) response to stress, either up or down, to cold, mannitol, or salt in roots but not in leaves are shown below in Table 7. Of the nine root-specific promoters identified, one did not show a response to any of the stresses, two were downregulated in response to cold, mannitol and stress, four were upregulated in response to at least one of the stresses and downregulated in response to at least one of the stresses, and two were only downregulated by salt stress.

TABLE 7

| | | Roots | | | | | |
|---|---|---|---|---|---|---|---|
| Accession | Affy id | Cold Root3 | Cold Root27 | Man Root3 | Man Root27 | Salt Root3 | Salt Root27 |
| AC006577.16 | 12778_r_at | −1985 | −3753 | −2768 | −363 | −4018 | −1769 |
| ATU57320 | 15137_s_at | −729 | −219 | −1304 | 992 | −2420 | 141 |
| X98808.1 | 15985_at | −2123 | 1183 | −1881 | −312 | −2331 | −343 |
| U81294.2 | 20421_at | −19 | 2399 | −1162 | 345 | −1450 | 371 |
| Z97338.321 | 16045_s_at | −1068 | −694 | −1084 | 124 | −1425 | −285 |
| X98855.2 | 16028_at | −448 | −691 | −595 | −589 | −1043 | −559 |
| AC006577.16 | 12779_f_at | −672 | −763 | −636 | −419 | −976 | −559 |
| X78586.2 | 16048_at | 56 | 603 | −576 | 307 | −881 | −588 |
| ATU62330 | 15623_f_at | −1274 | 373 | −1054 | 141 | −817 | 439 |
| NOVARTIS51 | 14170_at | −1058 | 537 | −654 | −14 | −718 | 16 |
| AC005560.136 | 16016_at | 93 | 643 | 25 | 628 | −648 | −232 |
| AF098630.3 | 19118_s_at | 228 | 422 | −52 | −37 | −640 | −117 |
| AF128395.12 | 20395_at | −286 | −508 | −482 | −115 | −621 | 261 |
| Z97340.345 | 17485_s_at | −691 | −1934 | −357 | −592 | −529 | −454 |
| AL035538.245 | 16514_at | 200 | −498 | 798 | 935 | −490 | −118 |
| X98322.2 | 17942_s_at | −366 | 54 | −285 | 4 | −457 | 3 |
| ATU10034 | 15120_s_at | −102 | 134 | −336 | −80 | −456 | −65 |
| AL049730.104 | 18983_s_at | 322 | −51 | −272 | −167 | −439 | −570 |
| AJ133036.5 | 15969_s_at | −316 | −619 | 74 | −465 | −400 | −470 |
| U72155.2 | 15954_at | 52 | −178 | −86 | −447 | −388 | −252 |
| X98319.2 | 16971_s_at | −368 | 9 | −291 | −62 | −368 | −86 |
| U81294.2 | 20422_g_at | −96 | 530 | −272 | 43 | −341 | 32 |
| X67421.3 | 16489_at | 446 | 200 | −158 | −41 | −323 | −357 |
| Y11788.1 | 18946_at | 100 | 146 | −58 | −21 | −199 | 124 |
| ATPIN2 | 12932_s_at | −172 | −182 | −158 | −67 | −170 | −128 |
| AC005310.6 | 17697_at | −99 | 18 | −97 | −15 | −139 | −23 |
| AC007135.23 | 20176_at | −37 | 82 | 260 | 137 | −120 | −81 |
| AC006587.164 | 15859_at | 91 | 134 | 29 | 13 | −117 | −8 |
| AC004521.114 | 19195_at | −410 | 93 | −322 | −36 | −96 | −20 |
| X98321.2 | 19595_s_at | −50 | −149 | −66 | 0 | −95 | 73 |
| AC002333.199 | 13552_at | −205 | −418 | 167 | 101 | −89 | −148 |
| AL024486.185 | 16299_at | −162 | −165 | −76 | −47 | −80 | −20 |
| AC004521.119 | 20608_s_at | −201 | 96 | −119 | −7 | −75 | 15 |
| A71597.1 | 12079_at | −185 | −153 | 79 | −142 | −74 | −60 |
| AC006216.26 | 18571_at | −46 | 55 | 23 | −26 | −71 | 10 |
| AC006216.22 | 14050_at | −45 | 14 | −23 | −14 | −62 | −8 |
| AL080253.32 | 19415_at | 112 | −132 | 107 | 118 | −56 | −108 |
| AC004683.79 | 16461_i_at | −145 | −621 | −136 | −164 | −17 | 142 |
| X74514.2 | 20239_g_at | 13 | 213 | 60 | −91 | 1 | 1 |
| AL080282.74 | 18597_at | −251 | 161 | −58 | 120 | 4 | −24 |
| AC002333.210 | 13153_r_at | −5 | −186 | 48 | −82 | 9 | −51 |
| X74514.2 | 20238_at | 288 | 553 | 174 | 115 | 10 | 302 |
| CAFFEROYLCOA-METHYLTRANS | 13215_s_at | 42 | 33 | 38 | −20 | 12 | −56 |
| AC004005.104 | 19390_at | −77 | 0 | −121 | 37 | 13 | −16 |
| ATHORF | 16649_s_at | 54 | 112 | 43 | 17 | 16 | −8 |
| AC003673.201 | 16481_s_at | −38 | −106 | 16 | −22 | 17 | −28 |
| ATAJ2596 | 16085_s_at | 128 | −137 | 240 | 64 | 30 | −47 |
| AC002333.210 | 13154_s_at | −6 | −511 | 168 | −224 | 31 | −172 |
| AC004684.165 | 17907_s_at | −154 | −52 | −3 | 106 | 40 | 65 |
| AL049638.193 | 20029_at | 45 | 41 | 35 | −42 | 64 | −20 |
| A71588.1 | 14015_s_at | −130 | 138 | 164 | −23 | 79 | −1 |
| A71596.1 | 14016_s_at | −104 | 99 | 132 | −15 | 98 | 1 |
| Z99707.288 | 18326_s_at | 150 | −110 | 309 | 19 | 99 | −75 |
| ACHI | 12852_s_at | −25 | 36 | 97 | −7 | 114 | −20 |
| AC005560.147 | 12758_at | 33 | −822 | 362 | 357 | 121 | 146 |
| X98320.2 | 18312_s_at | 38 | 29 | 293 | 21 | 131 | −14 |
| AC002391.150 | 17843_s_at | 79 | 170 | 26 | 15 | 177 | 1 |
| AC005967.50 | 17864_at | 37 | 133 | 41 | −37 | 196 | −4 |
| AC007060.34 | 19840_s_at | 606 | 1194 | 304 | −145 | 286 | 185 |
| BCHI | 13211_s_at | 99 | −554 | 337 | −242 | 312 | −275 |
| AC001645.19 | 15965_at | −323 | −177 | 141 | −437 | 355 | −389 |
| AB023448.2 | 12332_s_at | 170 | −704 | 421 | −130 | 370 | −374 |
| AC001645.47 | 15996_at | −160 | −167 | 215 | −162 | 445 | −147 |
| AL049500.57 | 16914_s_at | 96 | −2596 | 366 | −818 | 541 | −1265 |
| AC007584.48 | 20194_at | 288 | 0 | 848 | 259 | 1016 | −116 |

TABLE 7-continued

| | | Leaves | | | | | |
|---|---|---|---|---|---|---|---|
| Accession | Affy id | Cold Leaf3 | Cold Leaf27 | Man Leaf3 | Man Leaf27 | Salt Leaf3 | Salt Leaf27 |
| AC006577.16 | 12778_r_at | 80 | −89 | 92 | −81 | −14 | −167 |
| ATU57320 | 15137_s_at | 158 | 63 | 53 | 5 | −35 | −79 |
| X98808.1 | 15985_at | −5 | −136 | −11 | −137 | 5 | −93 |
| U81294.2 | 20421_at | 35 | −8 | 18 | 81 | 52 | −19 |
| Z97338.321 | 16045_s_at | 10 | −8 | 1 | 2 | 5 | −4 |
| X98855.2 | 16028_at | −1 | −16 | −2 | −13 | 1 | −13 |
| AC006577.16 | 12779_f_at | −83 | −57 | −47 | −53 | −34 | −58 |
| X78586.2 | 16048_at | 69 | 96 | 149 | 78 | 36 | 81 |
| ATU62330 | 15623_f_at | −3 | 8 | −4 | 42 | 49 | −14 |
| NOVARTIS51 | 14170_at | −188 | 1031 | −258 | −311 | −310 | −195 |
| AC005560.136 | 16016_at | 1 | 0 | 7 | 7 | 4 | 5 |
| AF098630.3 | 19118_s_at | 1 | −9 | −6 | 1 | −2 | −5 |
| AF128395.12 | 20395_at | 3 | 1 | 10 | 3 | 6 | −2 |
| Z97340.345 | 17485_s_at | 103 | −619 | 20 | −200 | −54 | −521 |
| AL035538.245 | 16514_at | 15 | 10 | 6 | 10 | 5 | −2 |
| X98322.2 | 17942_s_at | −1 | 0 | −2 | −2 | 2 | −1 |
| ATU10034 | 15120_s_at | 10 | −85 | −3 | −81 | −3 | −25 |
| AL049730.104 | 18983_s_at | −6 | 13 | 0 | 14 | −4 | 7 |
| AJ133036.5 | 15969_s_at | 4 | 13 | 12 | 13 | 25 | 7 |
| U72155.2 | 15954_at | 4 | 4 | 0 | −7 | 4 | −2 |
| X98319.2 | 16971_s_at | −4 | 3 | 3 | −2 | 1 | −5 |
| U81294.2 | 20422_g_at | 12 | 0 | 6 | 9 | 11 | −4 |
| X67421.3 | 16489_at | −3 | 2 | −5 | 0 | −2 | 2 |
| Y11788.1 | 18946_at | −177 | −203 | −175 | −204 | −158 | 285 |
| ATPIN2 | 12932_s_at | −13 | −1 | −2 | 1 | −3 | −6 |
| AC005310.6 | 17697_at | −3 | 2 | −1 | −3 | 0 | −5 |
| AC007135.23 | 20176_at | 8 | 3 | 0 | −1 | 1 | −6 |
| AC006587.164 | 15859_at | −51 | −62 | −54 | −47 | −56 | 50 |
| AC004521.114 | 19195_at | −35 | 2 | −12 | 1 | −3 | −21 |
| X98321.2 | 19595_s_at | 2 | −4 | −1 | 0 | 0 | 2 |
| AC002333.199 | 13552_at | 4 | 7 | −1 | 2 | 1 | 6 |
| AL024486.185 | 16299_at | −15 | −139 | −26 | −33 | −31 | −35 |
| AC004521.119 | 20608_s_at | −18 | 1 | −15 | −2 | 2 | −6 |
| A71597.1 | 12079_s_at | −4 | −22 | −5 | −10 | 5 | −7 |
| AC006216.26 | 18571_at | −1 | 9 | 2 | 10 | 4 | 10 |
| AC006216.22 | 14050_at | −2 | −1 | −3 | −4 | −2 | 2 |
| AL080253.32 | 19415_at | 6 | 0 | 3 | 0 | 2 | 6 |
| AC004683.79 | 16461_i_at | 26 | 0 | 8 | 17 | 14 | 21 |
| X74514.2 | 20239_g_at | −11 | 84 | 4 | −60 | −55 | −48 |
| AL080282.74 | 18597_at | −62 | 284 | 27 | 36 | −40 | 23 |
| AC002333.210 | 13153_r_at | 52 | −23 | 41 | 35 | −6 | −42 |
| X74514.2 | 20238_at | −9 | 218 | 0 | −112 | −180 | −194 |
| CAFFEROYLCOA-METHYLTRANS | 13215_s_at | 20 | 31 | 7 | 0 | 1 | −8 |
| AC004005.104 | 19390_at | 8 | −3 | −3 | 1 | 4 | −13 |
| ATHORF | 16649_s_at | 47 | 39 | 9 | 2 | −2 | −8 |
| AC003673.201 | 16481_s_at | 3 | 0 | 0 | 5 | 1 | 7 |
| ATAJ2596 | 16085_s_at | 0 | −1 | −9 | 2 | −3 | 1 |
| AC002333.210 | 13154_s_at | 74 | −63 | 198 | 75 | −20 | −84 |
| AC004684.165 | 17907_s_at | 17 | −29 | 16 | 25 | 15 | −8 |
| AL049638.193 | 20029_at | −4 | −18 | −6 | −5 | 0 | −9 |
| A71588.1 | 14015_s_at | 5 | −7 | 2 | −6 | 13 | −10 |
| A71596.1 | 14016_s_at | 8 | −3 | 11 | −2 | −1 | 1 |
| Z99707.288 | 18326_s_at | 1 | 2 | −1 | 3 | 0 | −3 |
| ACHI | 12852_s_at | 16 | −6 | 9 | 9 | 8 | −10 |
| AC005560.147 | 12758_at | 2 | 1 | 1 | 10 | 3 | 3 |
| X98320.2 | 18312_s_at | 1 | −2 | 1 | 5 | −2 | 0 |
| AC002391.150 | 17843_s_at | 416 | −53 | 487 | 239 | 184 | 63 |
| AC005967.50 | 17864_at | 8 | 8 | 5 | 10 | 5 | 0 |
| AC007060.34 | 19840_s_at | −80 | 169 | 106 | 105 | −2 | 50 |
| BCHI | 13211_s_at | 44 | −94 | −1 | −13 | 37 | −54 |
| AC001645.19 | 15965_at | −24 | −3 | −22 | −4 | 25 | −27 |
| AB023448.2 | 12332_s_at | 127 | −172 | 9 | −10 | 9 | −133 |
| AC001645.47 | 15996_at | 5 | −10 | 6 | −6 | 29 | −20 |
| AL049500.57 | 16914_s_at | 265 | −341 | 19 | −7 | 78 | −354 |
| AC007584.48 | 20194_at | 27 | 182 | 78 | 62 | 30 | 32 |

TABLE 8

Root genes up- or down-regulated in response to cold, mannitol or salt stress

| Accession # | Affy # | Description |
|---|---|---|
| \multicolumn{3}{c}{Down regulated with cold stress in rant (acute response 3 hrs)} |||
| X98808.1 | 15985_at | emb|CAA67340.1| (X98808) peroxidase ATP3a [*Arabidopsis thaliana*] |
| AC006577.16 | 12778_r_at | "gb|AAD25772.1|AC006577_8 (AC006577) Belongs to the PF|00657 Lipase/Acylhydrolase with GDSL-motif family. ESTs gb|T44453, gb|T04815, gb|T45993, gb|R30138, gb|AI099570 and gb|T22281 come from this gene. [*Arabidopsis thaliana*]" |
| ATU62330 | 15623_f_at | dbj|BAA21503.1| (D86591) inorganic phosphate transporter [*Arabidopsis thaliana*] |
| Z97338.321 | 16045_s_at | emb|CAB10318.1| (Z97338) HSR201 like protein [*Arabidopsis thaliana*] |
| AC006577.16 | 12779_f_at | "gb|AAD25772.1|AC006577_8 (AC006577) Belongs to the PF|00657 Lipase/Acylhydrolase with GDSL-motif family. ESTs gb|T44453, gb|T04815, gb|T45993, gb|R30138, gb|AI099570 and gb|T22281 come from this gene. [*Arabidopsis thaliana*]" |
| X98855.2 | 16028_at | emb|CAA67361.1| (X98855) peroxidase ATP8a [*Arabidopsis thaliana*] |
| AC004521.114 | 19195_at | gb|AAC16105.1| (AC004521) unknown protein [*Arabidopsis thaliana*] |
| X98319.2 | 16971_s_at | emb|CAA66963.1| (X98319) peroxidase [*Arabidopsis thaliana*] |
| X98322.2 | 17942_s_at | emb|CAA66966.1| (X98322) peroxidase [*Arabidopsis thaliana*] |
| AC001645.19 | 15965_at | gb|AAB63631.1| (AC001645) jasmonate inducible protein isolog [Arabidopsis thaliana] |
| AJ133036.5 | 15969_s_at | emb|CAA67313.1| (X98777) peroxidase ATP16a [*Arabidopsis thaliana*] |
| AF128395.12 | 20395_at | "gb|AAD17355.1| (AF128395) contains similarity to pathogenesis-related protein 1 precursors and SCP-like extracellular proteins (Pfam: PF00188, Score = 79.8, E = 4.1e−21, N = 1) [*Arabidopsis thaliana*]" |
| AL080282.74 | 18597_at | emb|CAB45881.1| (AL080282) berberine bridge enzyme-like protein [*Arabidopsis thaliana*] |
| AC002333.199 | 13552_at | gb|AAB64045.1| (AC002333) endochitinase isolog [*Arabidopsis thaliana*] |
| AC004521.119 | 20608_s_at | gb|AAC16106.1| (AC004521) hypothetical protein [*Arabidopsis thaliana*] |
| A71597.1 | 12079_s_at | emb|CAB42613.1| (A71641) unnamed protein product [*Arabidopsis thaliana*] |
| ATPIN2 | 12932_s_at | gb|AAC84042.1| (AF087459) polar-auxin-transport efflux component AGRAVITROPIC 1 [*Arabidopsis thaliana*] |
| AL024486.185 | 16299_at | emb|CAA19705.1| (AL024486) putative protein [*Arabidopsis thaliana*] |
| AC001645.47 | 15996_at | gb|AAB63634.1| (AC001645) jasmonate inducible protein isolog [*Arabidopsis thaliana*] |
| AC004684.165 | 17907_s_at | gb|AAC23645.1| (AC004684) unknown protein [*Arabidopsis thaliana*] |
| AC004683.79 | 16461_i_at | gb|AAC28766.1| (AC004683) peroxidase [*Arabidopsis thaliana*] |
| A71588.1 | 14015_s_at | emb|CAB42586.1| (A71588) unnamed protein product [*Arabidopsis thaliana*] |
| \multicolumn{3}{c}{Upregulated in root cold stress} |||
| AL035538.245 | 16514_at | emb|CAB37548.1| (AL035538) putative protein [*Arabidopsis thaliana*] |
| AF098630.3 | 19118_s_at | emb|CAB41725.1| (AL049730) putative cell wall-plasma membrane disconnecting CLCT protein (AIR1A) [*Arabidopsis thaliana*] |
| AC007584.48 | 20194_at | gb|AAD32907.1|AC007584_5 (AC007584) unknown protein [*Arabidopsis thaliana*] |
| X74514.2 | 20238_at | emb|CAA52620.1| (X74515) beta-fructofuranosidase [*Arabidopsis thaliana*] |
| AL049730.104 | 18983_s_at | emb|CAB41721.1| (AL049730) pEARLI 1-like protein [*Arabidopsis thaliana*] |
| X67421.3 | 16489_at | emb|CAA47807.1| (X67421) extA [*Arabidopsis thaliana*] |
| AC007060.34 | 19840_s_at | gb|AAD25759.1|AC007060_17 (AC007060) Strong similarity to F19I3.2 gi|3033375 putative berberine bridge enzyme from *Arabidopsis thaliana* BAC gb|AC004238. EST gb|R90518 comes from this gene. |

TABLE 8-continued

Root genes up- or down-regulated in response to cold, mannitol or salt stress

| Accession # | Affy # | Description |
|---|---|---|
| \multicolumn{3}{c}{Acute (3 hrs) manitol stress response downregulated root genes} |
| AC006577.16 | 12778_r_at | "gb|AAD25772.1|AC006577_8 (AC006577) Belongs to the PF|00657 Lipase/Acylhydrolase with GDSL-motif family. ESTs gb|T44453, gb|T04815, gb|T45993, gb|R30138, gb|AI099570 and gb|T22281 come from this gene. [*Arabidopsis thaliana*]" |
| X98808.1 | 15985_at | emb|CAA67340.1| (X98808) peroxidase ATP3a [*Arabidopsis thaliana*] |
| ATU57320 | 15137_s_at | gb|AAB47973.1| (U57320) blue copper-binding protein II [*Arabidopsis thaliana*] |
| U81294.2 | 20421_at | emb|CAB10242.1| (Z97336) germin precursor oxalate oxidase [*Arabidopsis thaliana*] |
| Z97338.321 | 16045_s_at | emb|CAB10318.1| (Z97338) HSR201 like protein [*Arabidopsis thaliana*] |
| ATU62330 | 15623_f_at | dbj|BAA21503.1| (D86591) inorganic phosphate transporter [*Arabidopsis thaliana*] |
| AC006577.16 | 12779_f_at | "gb|AAD25772.1|AC006577_8 (AC006577) Belongs to the PF|00657 Lipase/Acylhydrolase with GDSL-motif family. ESTs gb|T44453, gb|T04815, gb|T45993, gb|R30138, gb|AI099570 and gb|T22281 come from this gene. [*Arabidopsis thaliana*]" |
| X98855.2 | 16028_at | emb|CAA67361.1| (X98855) peroxidase ATP8a [*Arabidopsis thaliana*] |
| AF128395.12 | 20395_at | "gb|AAD17355.1| (AF128395) contains similarity to pathogenesis-related protein 1 precursors and SCP-like extracellular proteins (Pfam: PF00188, Score = 79.8, E = 4.1e−21, N = 1) [*Arabidopsis thaliana*]" |
| Z97340.345 | 17485_s_at | "emb|CAB10405.1| (Z97340) beta-1, 3-glucanase class I precursor [*Arabidopsis thaliana*]" |
| ATU10034 | 15120_s_at | gb|AAA93132.1| (U10034) glutamate decarboxylase [*Arabidopsis thaliana*] |
| AC004521.114 | 19195_at | gb|AAC16105.1| (AC004521) unknown protein [*Arabidopsis thaliana*] |
| X98319.2 | 16971_s_at | emb|CAA66963.1| (X98319) peroxidase [*Arabidopsis thaliana*] |
| X98322.2 | 17942_s_at | emb|CAA66966.1| (X98322) peroxidase [*Arabidopsis thaliana*] |
| U81294.2 | 20422_g_at | emb|CAB10242.1| (Z97336) germin precursor oxalate oxidase [*Arabidopsis thaliana*] |
| AL049730.104 | 18983_s_at | emb|CAB41721.1| (AL049730) pEARL| 1-like protein [*Arabidopsis thaliana*] |
| ATPIN2 | 12932_s_at | gb|AAC84042.1| (AF087459) polar-auxin-transport efflux component AGRAVITROPIC 1 [*Arabidopsis thaliana*] |
| X67421.3 | 16489_at | emb|CAA47807.1| (X67421) extA [*Arabidopsis thaliana*] |
| AC004683.79 | 16461_i_at | gb|AAC28766.1| (AC004683) peroxidase [*Arabidopsis thaliana*] |
| AC004005.104 | 19390_at | gb|AAC23409.1| (AC004005) unknown protein [*Arabidopsis thaliana*] |
| AC004521.119 | 20608_s_at | gb|AAC16106.1| (AC004521) hypothetical protein [*Arabidopsis thaliana*] |
| \multicolumn{3}{c}{Manitol stress upregulated in root genes only (acute response)} |
| AL080253.32 | 19415_at | emb|CAB45805.1| (AL080253) putative protein [*Arabidopsis thaliana*] |
| A71596.1 | 14016_s_at | emb|CAB42592.1| (A71596) unnamed protein product [*Arabidopsis thaliana*] |
| AC001645.19 | 15965_at | gb|AAB63631.1| (AC001645) jasmonate inducible protein isolog [*Arabidopsis thaliana*] |
| A71588.1 | 14015_s_at | emb|CAB42586.1| (A71588) unnamed protein product [*Arabidopsis thaliana*] |
| AC002333.199 | 13552_at | gb|AAB64045.1| (AC002333) endochitinase isolog [*Arabidopsis thaliana*] |
| X74514.2 | 20238_at | emb|CAA52620.1| (X74515) beta-fructofuranosidase [*Arabidopsis thaliana*] |
| AC001645.47 | 15996_at | gb|AAB63634.1| (AC001645) jasmonate inducible protein isolog [*Arabidopsis thaliana*] |
| ATAJ2596 | 16085_s_at | emb|CAB16787.1| (Z99707) patatin-like protein [*Arabidopsis thaliana*] |
| AC007135.23 | 20176_at | gb|AAD26967.1|AC007135_3 (AC007135) unknown protein [*Arabidopsis thaliana*] |
| X98320.2 | 18312_s_at | emb|CAA67310.1| (X98774) peroxidase ATP6a [*Arabidopsis thaliana*] |
| Z99707.288 | 18326_s_at | emb|CAB16788.1| (Z99707) patatin-like protein [*Arabidopsis thaliana*] |

TABLE 8-continued

Root genes up- or down-regulated in response to cold, mannitol or salt stress

| Accession # | Affy # | Description |
| --- | --- | --- |
| BCHI | 13211_s_at | dbj|BAA82825.1| (AB023463) basic endochitinase [*Arabidopsis thaliana*] |
| AC005560.147 | 12758_at | gb|AAC67329.1| (AC005560) putative major latex protein [*Arabidopsis thaliana*] |
| AL049500.57 | 16914_s_at | emb|CAB39936.1| (AL049500) osmotin precursor [*Arabidopsis thaliana*] |
| AB023448.2 | 12332_s_at | dbj|BAA82810.1| (AB023448) basic endochitinase [*Arabidopsis thaliana*] |
| AL035538.245 | 16514_at | emb|CAB37548.1| (AL035538) putative protein [*Arabidopsis thaliana*] |
| AC007584.48 | 20194_at | gb|AAD32907.1|AC007584_5 (AC007584) unknown protein [*Arabidopsis thaliana*] |
| Salt stress acute response down regulated root only | | |
| AC006577.16 | 12778_r_at | "gb|AAD25772.1|AC006577_8 (AC006577) Belongs to the PF|00657 Lipase/Acylhydrolase with GDSL-motif family. ESTs gb|T44453, gb|T04815, gb|T45993, gb|R30138, gb|AI099570 and gb|T22281 come from this gene. [*Arabidopsis thaliana*]" |
| ATU57320 | 15137_s_at | gb|AAB47973.1| (U57320) blue copper-binding protein II [*Arabidopsis thaliana*] |
| X98808.1 | 15985_at | emb|CAA67340.1| (X98808) peroxidase ATP3a [*Arabidopsis thaliana*] |
| U81294.2 | 20421_at | emb|CAB10242.1| (Z97336) germin precursor oxalate oxidase [*Arabidopsis thaliana*] |
| Z97338.321 | 16045_s_at | emb|CAB10318.1| (Z97338) HSR201 like protein [*Arabidopsis thaliana*] |
| X98855.2 | 16028_at | emb|CAA67361.1| (X98855) peroxidase ATP8a [*Arabidopsis thaliana*] |
| AC006577.16 | 12779_f_at | "gb|AAD25772.1|AC006577_8 (AC006577) Belongs to the PF|00657 Lipase/Acylhydrolase with GDSL-motif family. ESTs gb|T44453, gb|T04815, gb|T45993, gb|R30138, gb|AI099570 and gb|T22281 come from this gene. [*Arabidopsis thaliana*]" |
| X78586.2 | 16048_at | emb|CAA55323.1| (X78586) Dr4 [*Arabidopsis thaliana*] |
| ATU62330 | 15623_f_at | dbj|BAA21503.1| (D86591) inorganic phosphate transporter [*Arabidopsis thaliana*] |
| AC005560.136 | 16016_at | gb|AAC67328.1| (AC005560) putative major latex protein [*Arabidopsis thaliana*] |
| AF098630.3 | 19118_s_at | emb|CAB41725.1| (AL049730) putative cell wall-plasma membrane disconnecting CLCT protein (AIR1A) [*Arabidopsis thaliana*] |
| AF128395.12 | 20395_at | "gb|AAD17355.1| (AF128395) contains similarity to pathogenesis-related protein 1 precursors and SCP-like extracellular proteins (Pfam: PF00188, Score = 79.8, E = 4.1e−21, N = 1) [*Arabidopsis thaliana*]" |
| Z97340.345 | 17485_s_at | "emb|CAB10405.1| (Z97340) beta-1, 3-glucanase class I precursor [*Arabidopsis thaliana*]" |
| AL035538.245 | 16514_at | emb|CAB37548.1| (AL035538) putative protein [*Arabidopsis thaliana*] |
| X98322.2 | 17942_s_at | emb|CAA66966.1| (X98322) peroxidase [*Arabidopsis thaliana*] |
| ATU10034 | 15120_s_at | gb|AAA93132.1| (U10034) glutamate decarboxylase [*Arabidopsis thaliana*] |
| AL049730.104 | 18983_s_at | emb|CAB41721.1| (AL049730) pEARLI 1-like protein [*Arabidopsis thaliana*] |
| AJ133036.5 | 15969_s_at | emb|CAA67313.1| (X98777) peroxidase ATP16a [*Arabidopsis thaliana*] |
| U72155.2 | 15954_at | gb|AAB64244.1| (U72155) beta-glucosidase [*Arabidopsis thaliana*] |
| X98319.2 | 16971_s_at | emb|CAA66963.1| (X98319) peroxidase [*Arabidopsis thaliana*] |
| U81294.2 | 20422_g_at | emb|CAB10242.1| (Z97336) germin precursor oxalate oxidase [*Arabidopsis thaliana*] |
| X67421.3 | 16489_at | emb|CAA47807.1| (X67421) extA [*Arabidopsis thaliana*] |
| ATPIN2 | 12932_s_at | gb|AAC84042.1| (AF087459) polar-auxin-transport efflux component AGRAVITROPIC 1 [*Arabidopsis thaliana*] |
| AC005310.6 | 17697_at | gb|AAC33493.1| (AC005310) unknown protein [*Arabidopsis thaliana*] |
| AC007135.23 | 20176_at | gb|AAD26967.1|AC007135_3 (AC007135) unknown protein [*Arabidopsis thaliana*] |

TABLE 8-continued

Root genes up- or down-regulated in response to cold, mannitol or salt stress

| Accession # | Affy # | Description |
|---|---|---|
| *Salt stress acute response up regulated root only* | | |
| AC005967.50 | 17864_at | gb\|AAD03387.1\| (AC005967) unknown protein [*Arabidopsis thaliana*] |
| AC007060.34 | 19840_s_at | gb\|AAD25759.1\|AC007060_17 (AC007060) Strong similarity to F19\|3.2 gi\|3033375 putative berberine bridge enzyme from *Arabidopsis thaliana* BAC gb\|AC004238. EST gb\|R90518 comes from this gene. |
| BCHI | 13211_s_at | dbj\|BAA82825.1\| (AB023463) basic endochitinase [*Arabidopsis thaliana*] |
| AC001645.19 | 15965_at | gb\|AAB63631.1\| (AC001645) jasmonate inducible protein isolog [*Arabidopsis thaliana*] |
| AB023448.2 | 12332_s_at | dbj\|BAA82810.1\| (AB023448) basic endochitinase [*Arabidopsis thaliana*] |
| AC001645.47 | 15996_at | gb\|AAB63634.1\| (AC001645) jasmonate inducible protein isolog [*Arabidopsis thaliana*] |
| AL049500.57 | 16914_s_at | emb\|CAB39936.1\| (AL049500) osmotin precursor [*Arabidopsis thaliana*] |
| AC007584.48 | 20194_at | gb\|AAD32907.1\|AC007584_5 (AC007584) unknown protein [*Arabidopsis thaliana*] |
| *Genes expressed in root that have no acute response to stress* | | |
| X98321.2 | 19595_s_at | emb\|CAA66965.1\| (X98321) peroxidase [*Arabidopsis thaliana*] |
| AC006216.26 | 18571_at | gb\|AAD12681.1\| (AC006216) Similar to gi\|3413714 T19L18.21 putative myrosinase-binding protein from *Arabidopsis thaliana* BAC gb\|AC004747. ESTs gb\|65870 and gb\|T20812 come from this gene. |
| AC006216.22 | 14050_at | "gb\|AAD12679.1\| (AC006216) Similar to gi\|3413714 T19L18.21 putative myrosinase-binding protein from *Arabidopsis thaliana* BAC gb\|AC004747. ESTs gb\|T44298, gb\|T42447, gb\|R64761 and gb\|I100206 come from this gene." |
| AL080253.32 | 19415_at | emb\|CAB45805.1\| (AL080253) putative protein [*Arabidopsis thaliana*] |
| X74514.2 | 20239_g_at | emb\|CAA52620.1\| (X74515) beta-fructofuranosidase [*Arabidopsis thaliana*] |
| AC002333.210 | 13153_r_at | gb\|AAB64320.1\| (AC002335) endochitinase isolog [*Arabidopsis thaliana*] |
| CAFFEROYLCOAMET HYLTRANS | 13215_s_at | gb\|AAA62426.1\| (L40031) S-adenosyl-L-methionine: trans-caffeoyl-Coenzyme A 3-O-methyltransferase [*Arabidopsis thaliana*] |
| ATHORF | 16649_s_at | gb\|AAA62426.1\| (L40031) S-adenosyl-L-methionine: trans-caffeoyl-Coenzyme A 3-O-methyltransferase [*Arabidopsis thaliana*] |
| AC003673.201 | 16481_s_at | gb\|AAC09031.1\| (AC003673) peroxidase ATP22a [*Arabidopsis thaliana*] |
| AL049638.193 | 20029_at | emb\|CAB40949.1\| (AL049638) putative DNA-binding protein [*Arabidopsis thaliana*] |

2. Dynamics of Gene Expression During Leaf Development

In order to examine the dynamics of gene expression at mRNA level during different organ development, genes with transcripts detected in various developmental stages were analyzed. A total of 5,247 genes expressed during leaf development were subject to cluster analysis. Various clustering methods, including self-organizing map (SOM, Tamayo et al., 1999), hierarchical cluster (Eisen et al., 1998) and K-mean, generated similar clusters. Sixteen groups of genes formed according to their expression patterns when SOM was used. Four groups of genes were examined in detail.

Cluster 15 shows a group of genes down regulated during leaf development. Genes in this group generally have a very high transcription level. However, they reduce their expression level by least 2-fold toward senescence. Among 34 genes in the cluster, 28 of them were photosynthesis related. Interestingly, some of the genes related to photosynthesis are also found in cluster 6, which shows a more gradual reduction in expression. These genes, such as ferredoxin-NADP+ reductase and NADPH protochlorophyllide oxidoreductase B, have relatively low level of transcripts, and their reduction is not as dramatic as others.

Cluster 8 was also analyzed. The expression of this group of genes shows a dramatic increase towards senescence. Detailed examination of this cluster revealed 8 genes involved in senescence. Other senescence genes also increased their transcription level during late development, however, those changes were not as dramatic as the eight genes identified in cluster 8. These genes were found in cluster 2.

3. Function Characterization of Global Gene Expression Pattern

Cluster analysis also identifies co-regulated genes, and organizes the samples or array experiments according to their overall expression patterns. In order to validate the expression data, cluster analysis was performed on 6,626 genes with an expression level above background (average difference greater or equal 25) in any of the samples. All data were normalized to their median, organized into a SOM, and into a hierarchical cluster using Cluster program (Eisen et al. 1998).

According to the similarity of the global expression patterns of each sample, samples form three major clusters: a cluster of leaf samples, a cluster of supporting axis, including root, inflorescence stem and seedling samples, and a cluster of the reproductive organ samples, including samples of flowers, siliques, and inflorescences (including flowers and siliques). Similarly, genes also organized into several major classes according to their expression levels: organ-differentially expressed genes were easily highlighted.

It is worth noting that sample/experimental variations also contributed to the clusters. For example, the leaf gene expression data were produced from 2 independent experiments. One set of the leaf materials was collected in the morning at approximately 10 o'clock, and the other set was collected in the afternoon around 3 o'clock in the afternoon. The circadian regulated gene expression contributed greatly to form two sample clusters. These circadian regulated genes matched the genes described in Hammer et al. (2000).

4. Regulatory Sequences

To elucidate the regulatory elements of co-regulated genes, AlignACE was employed (Hughes et al., 2000). A total of 49 promoters were found to share a few potential and known cis-acting elements. Among these cis-acting elements identified from the ribosomal promoters, the telo-box motif (AAACCCTA) was observed in 41 of these ribosomal promoters. Telo-boxes have been found in many *Arabidopsis* ribosomal genes and in eEF1A (Tremousaygue et al., 1999). This telo-box binds a protein related to Pura conserved nuclear protein that has been implicated in the control of gene transcription and DNA replication (Safak et al., 1999). Another motif identified in the ribosomal promoter regions was the D of binding site (AAAG). The D of binding site has been shown in the promoters of a diverse set of plant genes, suggesting various roles of D of proteins in plants (Yanagisawa and Schmidt, 1999), including carbon metabolism (Yanagisawa, 2000). Additional motifs observed include a pollen specific motif (AGAAA) and a RAV1 binding motif (Kagaya et al., 1999).

The promoter regions from leaf-specific genes were also analyzed by AlignAce software to discover putative cis elements. Those that were found include a GATA box and a light regulatory element "ACGTGGCA". These elements are known to be necessary for light induced genes. A putative element that did not contain a known binding site was "TGGTTCGGACC" (SEQ ID NO:28).

A global gene expression pattern composed of the transcription profiles of 8,100 genes in 20 samples collected from different organs during *Arabidopsis* development was identified. By 166,000 gene expression measurements, the mRNA populations in different organs during *Arabidopsis* development were characterized. In particular, constitutively expressed genes and organ-differentially expressed genes were identified.

The accuracy of the microarray data was validated by two measures. First, the microarray results were repeatable. By comparing 15 pair of independently prepared labeled samples, less than 0.2% of the false positive rate was observed. The false positives occurred randomly among the genes with a low expression level. Second, expression levels measured by the oligonucleotide array correlated well with data from previous gene expression analysis and measurement from other technologies, such as RT-PCR.

Identification of constitutively and organ-differentially expressed genes is important to isolate constitutive or organ/tissue specific promoters. Here, it is demonstrated that the microarray technology can be used for large scale screening of these promoters, especially at the genome level. Moreover, genes that are co-regulated can be analyzed to identify the regulatory elements. In this study, constitutive and organ-specific genes were identified through the screening of 8,100 genes, but also regulatory elements, such as telo-box, D of binding site, as well as other motifs, which are important for the constitutive expression of the ribosomal proteins. By a similar approach, organ- or tissue-specific gene promoter elements, and various treatment-induced gene promoter elements, have been identified. Such results not only facilitate the dissection of the regulatory pathway, but also provide an opportunity in genetic engineering of metabolic pathways. Methods such as chimeraplasty (Zhu et al. 1999, 2000) can be used to precisely modify these regions and thus regulate a group of genes of interest.

Identification of co-regulated genes is the first step towards understanding of the regulation of a gene expression network, and assigning function to new genes. Among the 8,100 genes analyzed, approximately 3,100 genes do not have significant homology to known genes. Functional characterization of these genes becomes the challenge for the *Arabidopsis* genomics. A straightforward approach can be used to assign gene function: mutant lines or treated biological samples and their controls can be transcriptionally profiled. By comparing alterations in the expression of the novel genes, potential function can be assigned. The functions can be further confirmed by reverse genetics. Alternatively, genes with unknown function in the identified co-regulated gene clusters can be computationally analyzed by support vector machines (SVMs; Brown et al. 2000).

Similar experiments were conducted for root at least 3 hours after exposure to stress, e.g., salt, mannitol or cold (Tables 7-8). Twenty-five root-specific promoters were downregulated and 8 were upregulated in response to salt stress, 21 were down-regulated and 17 were upregulated in response to mannitol, and 22 were downregulated and 7 were upregulated in response to cold. Ten promoters did not respond to any of the stresses.

Example 3

Further Analysis of Constitutively Expressed Genes

A standard curve of 50, 10, 2, 0.4, and 0.08 ng total RNA was generated for each primer/probe set tested. In this case, the 50 ng sample yielded a $C_t$ value of 24.5 and the ng sample yields a $C_t$ value of 26.7. The $C_t$ value is defined as the threshold cycle whereby amplification occurs at an exponential rate. A low $C_t$ value correlates with high gene expression. The threshold is determined empirically from the standard curve. By raising or lowering the threshold, the data set is maximized to represent optimal exponential amplification. A correlation coefficient ($R^2$ of the best-fit line from the standard curve) greater than 99% and a slope of −3.3 (most efficient amplification) is ideal. For accurate repeatable results, the previous criteria must be met and the unknowns must fall within the range of the curve. The expression levels of the unknown can be interpolated from the unknown $C_t$ values using the standard curve.

TaqMan chemistry employs three gene-specific oligonucleotides for the detection of nucleic acids. Two of the oligonucleotides are primers used for the amplification of the molecule and the third oligonucleotide is a probe that is labeled with a 5' fluorescent reporter dye (6-FAM) and a 3' quencher dye (TAMRA). During PCR amplification, elongation proceeds once the DNA polymerase binds to the primer. As it polymerizes in the 5' to 3' direction, the polymerase encounters the quenched probe. The 5' to 3' exonuclease activity of the polymerase allows it to degrade the probe in its path, thereby releasing the 5' reporter dye. The thermocycler is equipped with a detection system to measure the fluorescence from the released reporter dye. Since fluorescence increases with amplification of the molecule, fluorescence can be directly related to the amount of molecules in the starting sample. The primers that were employed for one set were: TRX3T 5' 6-FAM agacttcactgcaacatggtgcccac TAMRA 3' (SEQ ID NO:29); TRX3F 5' gtgtggaaatgacaca-gattgtga3' (SEQ ID NO:30), and TRX3R 5' agacgggtgcaat-gaaacg3' (SEQ ID NO:31); and for the other set were: APX3 T 5' 6-FAM cgcgaacaagaactgtgctcctatcatg TAMRA 3' (SEQ ID NO:32), APX3 F 5' gccgtgagctccgttctct3' (SEQ ID NO:33); and APX3 R 5' tcgtgccatgccaatcg3' (SEQ ID NO:34). TaqMan chemistries were used with the ABI Prism 7700 Sequence system for relative quantitation of nucleic acid.

To find a gene whose expression is constitutive, the gene expression data obtained from the *Arabidopsis* GENECHIP® was analyzed. Three sets of data were analyzed (Table 9). Part A represents expression data for 2 genes from wild-type plants infected or not infected with *Pseudomonas syringae* pv. *maculicola* strain ES4326 at 30 hours post-inoculation. Part B represents expression data from wild-type *Arabidopsis* plants infected or not infected with 5 different viruses at 1 and 4 days after inoculation, while part C represents expression data for 2 genes in 9 different tissue types.

TABLE 9

A:

| PLANTS | TRX3 | APX3 |
|---|---|---|
| Columbia infected | 2481 | 484 |
| Columbia mock | 2362 | 495 |

B:

| DAYS | GENE | Mock | TVCV | ORMV | TRV | CMV | TuMV |
|---|---|---|---|---|---|---|---|
| 1 | TRX3 | 2020 | 1991 | 1738 | 2006 | 1833 | 1867 |
| 1 | APX3 | 711 | 557 | 717 | 755 | 658 | 426 |
| 4 | TRX3 | 1753 | 1978 | 1377 | 2249 | 1918 | 1928 |
| 4 | APX3 | 759 | 674 | 428 | 551 | 741 | 434 |

C:

| | TRX3 | APX3 |
|---|---|---|
| 4 day seed | 1282 | 488 |
| 2 week root | 1467 | 435 |
| Adult root | 1857 | 320 |
| 2 week leaf | 1233 | 771 |
| Adult leaf | 1483 | 857 |
| Senescing leaf | 1312 | 805 |
| Flowers | 694 | 513 |
| Inflorescence | 691 | 461 |
| Immature siliques | 614 | 508 |

After analyzing the data, 2 candidate genes were identified, thioredoxin (TRX3; GENBANK® Accession No. U35640) and ascorbate peroxidase (APX3; GENBANK® Accession No. U69138), whose expression did not vary more than 2-fold between the treatments in all experiments (except in flowers, inflorescence and siliques for TRX3). These genes also met the criteria of not having significant sequence similarity to other *Arabidopsis* genes.

Probe and primer sets were prepared for ubiquitin 5 (UBQ5), PR1 (a pathogenesis related gene whose expression is induced upon infection), TRX3 and APX3. TaqMan was used to quantify relative expression levels of these genes in *Arabidopsis* mutants and in uninfected and *P. syringae* infected plants. Table 10 shows that the PR1 expression increased rapidly upon infection. TRX3 and APX3 expression levels did not change as much as UBQ5, a commonly used gene for normalization.

TABLE 10

Gene expression in *Arabidopsis* infected with *P. syringae* at 34 hours post inoculation. Measured by Taq Man.

| PLANTS | PR1 | UBQ5 | TRX3 | APX3 |
|---|---|---|---|---|
| Columbia infected | 10 | 15 | 1.2 | 1.4 |
| Columbia Mock | .0033 | 2.7 | .62 | 1.4 |
| Pad4 mutant infected | 4.6 | 2.0 | 1.2 | 1.4 |
| Pad4 mutant Mock | .00027 | .79 | 1.1 | 2 |

Additionally, *Arabidopsis* plants were cold treated for 48 hours and the gene expression of these plants versus plants left at room temperature measured. There was no significant gene expression difference for PR1, TRX3, or APX3 (Table 11).

TABLE 11

| | Room temperature plants | Cold-treated plants |
|---|---|---|
| PR1 | 2.6 | 3.2 |
| TRX3 | 2.0 | 2.4 |
| APX3 | 2.1 | 2.8 |

In summary, gene-chip data was employed to find genes whose expression is constitutive in several *Arabidopsis* mutants, in infected plants, and throughout different tissues. TRX3 and APX3 expression levels varied less than UBQ5 in a comparison between infected and uninfected plants. TRX3 and APX3 gene expression was not significantly affected by cold-stress. Thus, TRX3 and APX3 are candidates for normalization when determining unknown gene expression levels in plants such as *Arabidopsis* or using quantitative PCR or other gene expression measurement assays. Likewise, the plant kingdom orthologs of these genes in dicots and monocots can be used for the same normalization standards for plants unrelated to *Arabidopsis*.

Moreover, unlike actin and ubiquitin (actin mediates cellular division and cycling and the ubiquitin pathway is activated upon stress, all of which may result in changes in gene expression), which belong to gene families to which probes can cross-hybridize, TRX3 and APX3 genes do not have significant similarity to genes in the *Arabidopsis* genome database, and the respective primer/probe sets described herein did not significantly cross-hybridize with other genes in the *Arabidopsis* genome database. Additionally, the promoters for these genes may be useful for constitutive gene expression.

Example 4

Construction of Binary Promoter::Reporter Plasmids

To construct a binary promoter::reporter plasmid for *Arabidopsis* transformation a vector containing a promoter of interest (i.e., the DNA sequence 5' of the initiation codon for the gene of interest) was used, which resulted from recombination in a BP reaction between a PCR product using the promoter of interest as a template and pDONRneo. The regulatory/promoter sequence was fused to the GUS reporter gene (Jefferson et al, 1987) by recombination using GATEWAY™ Technology according to manufacturers protocol as described in the Instruction Manual (GATEWAY™ Cloning Technology, GIBCO BRL, Rockville, Md.). Briefly, the promoter fragment in the vector is recombined via the LR reaction with a binary *Agrobacterium* destination vector containing the GUS coding region with an intron that has an attR site 5' to the GUS reporter (pNOV2374). The orientation of the inserted fragment was maintained by the att sequences and the final construct was verified by sequencing. The construct was then transformed into *Agrobacterium tumefaciens* strains by electroporation.

pNOV2374 is a binary vector with a VS1 origin of replication, a copy of the *Agrobacterium* virG gene in the backbone and a Basta resistance selectable marker cassette between the left and right border sequences of the T-DNA.

The Basta selectable marker cassette comprises the *Agrobacterium tumefaciens* manopine synthase promoter (AtMas et al., 1983) operably linked to the gene encoding Basta resistance (denoted here as "BAR", phosphinothricin acetyl transferase, White et al, 1990) and the 35S terminator. The AtMas promoter, BAR coding sequence and 35S terminator are located at nt 4211 to 4679, nt 4680 to 5228, and nt 5263 to 5488, respectively, of pNOV2374. The vector contains GATEWAY™ recombination components which were introduced into the binary vector backbone by ligating a blunt-ended cassette containing attR sites, ccdB and chloramphenicol resistance marker using the GATEWAY™ Vector Conversion System (LifeTechnologies). The GATEWAY™ cassette is located between nt 126 and 1818 of pNOV2374. The promoter cassettes are inserted through an LR recombination reaction whereby the DNA sequence of pNOV2374 between nt 126 and nt 1818 are removed and replaced with the promoter of interest flanked by att sequences. The recombination results in the promoter sequence fused to the GUS reporter gene with intron (GIG) sequence. The GIG gene contains the ST-LS1 intron from *Solanum tuberosum* at nt 385 to nt 576 of GUS (obtained from Dr. Stanton Gelvin, and described in Narasimhulu et al, 1996).

For comparison of promoter activity an additional construct was produced with the known *Arabidopsis* ubiquitin 3 (Ubq3(At), (Callis et al., 1990) promoter plus intron operatively linked to the GIG gene and the nos promoter. Thus, the orientation of the selectable marker and promoter-reporter cassette in the binary vector construct was RB Ubq3(At) promoter with intron fragment+GIG gene+nos—AtMas+ BAR+35S ter—LB Example 5

In Vitro Promoter Assays and *Arabidopsis* Transformation Plant Preparation and Growth

*Arabidopsis* seeds are sown on moistened Fafard Germinating Mix at a density of 9 seeds per 4" square pot, placed in a flat, covered with a plastic dome to retain moisture and moved to a growth chamber. Following germination the dome is removed and plants are grown for 3-5 weeks under short days (8 hrs light) to encourage vegetative growth and production of large plants with many flowers. Flowering is induced by providing long days (16 hrs. light) for 2-3 weeks, at which time plants are ready for dip inoculation into *Agrobacterium* to generate transgenic plants.

*Agrobacterium* Transformation, Culture Growth and Preparation for Plant Infiltration The binary promoter::reporter plasmids are introduced into *Agrobacteria* by electroporation. The binary plasmid confers spectinomycin resistance to the bacteria allowing cells containing the plasmid to be selected by growth of colonies on plates of LB+spectinomycin (50 mg/L). Presence of the correct promoter::GUS plasmid is confirmed by sequence analysis of the plasmid DNA isolated from the bacteria.

Two days prior to plant transformation 5 mL cultures of LB+spectinomycin (50 mg/L) are inoculated with the *Agrobacterium* strain containing the binary promoter::GUS plasmid and incubated at 30° C. for about 24 hours. Each 5 mL culture is then transferred to 500 mL of LB+spectinomycin (50 mg/L) and incubated for about 24 hours at 30° C. Each 500 mL culture is transferred to a centrifuge bottle and centrifuged at 5000 rpm for 10 minutes in a Sorvall Centrifuge. The supernatant is removed and the pelleted *Agrobacterium* cells are retained. The *Agrobacterium* cells are resuspended in 500 mL of modified Infiltration Media (IM+MOD: 50 g/L sucrose, 10 mM MgCl, 10 uM benzylaminopurine) to which 50 ul of Silwet L-77 (Dupont) has been added.

Plant Transformation by Dip Infiltration

Resuspended cells are poured into 1 L tri-pour beakers. Flowering plants are inverted into the culture, making sure all inflorescences are covered with the bacteria. The beakers are gently agitated for 30 seconds, keeping all inflorescence tissue submerged. Plants are returned to growth chamber following dip inoculation of the *Agrobacterium*. A second dip may be performed 5 days later to increase transformation frequency. Seeds are harvested ~4 to 6 weeks after transformation.

Selection of Transgenic *Arabidopsis*

Seeds from transformed *Arabidopsis* plants are sown on moistened Fafard Germinating Mix in a flat, covered with a dome to retain moisture and placed in a growth chamber. Following germination seedlings are sprayed with the herbicide BASTA. Transgenic plants are BASTA resistant due to the presence of the BAR gene in the binary promoter::GUS plasmid.

Promoter Assays

Promoter activity is evaluated qualitatively and quantitatively using histochemical and florescence assays for expression of the β-glucuronidase (GUS) enzyme.

Histochemical β-Glucuronidase (GUS) Assay

For qualitative evaluation of promoter activity, various *Arabidopsis* tissues and organs are used in GUS histochemical assays. Either whole organs or pieces of tissue are dipped into GUS staining solution. GUS staining solution contains 1 mM 5-bromo-4-chloro-3-indolyl glucuronide (X-Gluc, Duchefa, 20 mM stock in DMSO), 100 mM Na-phosphate buffer pH 7.0, 10 mM EDTA pH 8.0, and 0.1% Triton X100. Tissue samples are incubated at 37° C. for 1-16 hours. If necessary samples can be cleared with several washes of 70% EtOH to remove chlorophyll. Following staining tissues are viewed under a light microscope to evaluate the blue staining showing the GUS expression pattern.

β-Glucuronidase (GUS) Florescence Assay

For quantitative analysis of promoter activity in various *Arabidopsis* tissues and organs, GUS expression is measured fluorometrically. Tissue samples are harvested and ground in ice cold GUS extraction buffer (50 mM $Na_2HPO_4$ pH 7.0, 5 mM DTT, 1 mM $Na_2EDTA$, 0.1% Triton X100, 0.1% sarcosyl). Ground samples are spun in a microfuge at 10,000 rpm for 15 minutes at 4° C. Following centrifugation the supernatant is removed for GUS assay and for protein concentration determination.

To measure GUS activity the plant extract is assayed in GUS assay buffer (50 mM $Na_2HPO_4$ pH 7.0, 5 mM DTT, 1 mM $Na_2EDTA$, 0.1% TritonX100, 0.1% sarcosyl, 1 mM 4-Methylumbelliferyl-beta-D-glucuronic acid dihydrate (MUG)), prewarmed to 37° C. Reactions are incubated and 100 uL aliquots are removed at 10 minute intervals for 30 minutes to stop the reaction by adding to tubes containing 900 uL of 2% $Na_2CO_3$. The stopped reactions are then read on a Tecan Spectrofluorometer at 365 nm excitation and 455 emission wavelengths. Protein concentrations are determined using the BCA assay following manufacturers protocol. GUS activity is expressed as relative fluorometric units (RFU)/mg protein.

Example 6

Determination of the Minimal Promoter Fragment

The full-length promoter sequence as given in SEQ ID Nos: 1-26, or the promoter orthologs thereof is fused to the β-glucuronidase (GUS) gene at the native ATG to obtain a chimeric gene cloned into plasmid DNA. The plasmid DNA is then digested with restriction enzymes to release a fragment comprising the full-length promoter sequence and the GUS gene, which is then used to construct the binary vector. This binary vector is transformed into *Agrobacterium tumefaciens*, which is in turn used to transform *Arabidopsis* plants (for further details of the binary vector construction see above example 4)

The above plasmid can also be used to form a series of 5' end deletion mutants having increasingly shorter promoter fragments fused to the GUS gene at the native ATG. Various restriction enzymes are used to digest the plasmid DNA to obtain the binary vectors with different lengths of promoter fragments. In particular, a binary vector 1 is constructed with a 1,900-bp long promoter fragment; a binary vector 2 is constructed with a 1,300-bp long promoter fragment; a binary vector 3 is constructed with a 1000-bp long promoter fragment; a binary vector 4 is constructed with a 800-bp long promoter fragment; a binary vector 5 is constructed with a 700-bp long promoter fragment; a binary vector 6 is constructed with a 600-bp long promoter fragment; a binary vector 6 is constructed with a 500-bp long promoter fragment; and a binary vector 7 is constructed with a 100-bp long promoter fragment. Like the binary vector comprising the full-length promoter fragment, these 5' end deletion mutants are also transformed into *Agrobacterium tumefaciens* and, in turn, *Arabidopsis* plants (for further details of Arbabidopsis transformation and promoter assay procedures see example 5 above).

The presence of the correct hybrid construct in the transgenic lines is confirmed by PCR amplification.

By using the above protocol it can be determined, which portion of the promoter sequences given in SEQ ID Nos: 1-26, or the promoter orthologs thereof is required for gene expression.

Minimal promoter fragments having lengths substantially less than the full-length promoter can therefore be operatively linked to coding sequences to form smaller constructs than can be formed using the full-length promoter. As noted earlier, shorter DNA fragments are often more amenable to manipulation than longer fragments. The chimeric gene constructs thus formed can then be transformed into hosts such as crop plants to enable at-will regulation of coding sequences in the hosts.

Example 7

Determination of Promoter Motifs

While a deletion analysis characterizes regions in a promoter that are required overall for its regulation, linker-scanning mutagenesis allows for the identification of short defined motifs whose mutation alters the promoter activity. Accordingly, a set of linker-scanning mutant promoters fused to the coding sequence of the GUS reporter gene are constructed. Each of them contains a 8-10-bp mutation located between defined positions and included in a promoter fragment as given in SEQ ID Nos: 1-26, or the promoter orthologs thereof.

Each construct is transformed into *Arabidopsis* and GUS activity is assayed for 19 to 30 independent transgenic lines. The presence of the correct hybrid construct in transgenic lines is confirmed by PCR amplification of all lines containing the mutant constructs and by random sampling of lines containing the other constructs. Amplified fragments are digested with restriction enzyme (e.g. XbaI) and separated on high resolution agarose gels to distinguish between the different mutant constructs. constructs. The effect of each mutation on promoter activity is compared to an equivalent number of transgenic lines containing the unmutated construct. Two repetitions resulting from independent plating of seeds are carried out in every case.

The sequences mutated in the linker-scanning constructs, in particular those that showed marked differences from the control construct, are then examined more closely.

Example 8

Wound-Inducible Promoter

The AR10 promoter (SEQ ID NO: 17) is a root-specific promoter in *Arabidopsis*. Interestingly, AR10 was found to be a wound-inducible promoter when in a heterologous transgene.

An expression cassette containing the AR10 promoter was constructed by PCR amplifying the AR10 promoter from *Arabidopsis* and adding to it a SanDI site at the 5' terminus and a BamHI-TAAA-NcoI sequence at the 3' terminus. The PCR product was TOPO cloned and its sequence verified. The AR10 promoter was then digested with SanDI and NcoI and cloned into a plasmid containing a β-glucuronidase (GUS) gene and a Nos terminator at the same sites, thereby operably linking the AR10 promoter to GUS and Nos. The plasmid containing the AR10:GUS:Nos expression cassette was transformed into soybean using *Agrobacterium tumefaciens*. Nine T0 transformation events were selected for analysis.

Tissues were harvested from the T0 plants at early flowering and stained for GUS expression in roots, stems, petioles, petiole stems, leaves, flowers, meristems, and wounded areas. Plant tissues were dissected, placed in wells of a 12-well plate, and covered with GUS mix (per 100 ml: 10 ml of 1M $NaPO_4$, pH 7; 2 ml of 500 mM EDTA; 10 ml of 5 mM potassium ferrocyanide; 10 ml of 5 mM potassium ferricyanide; and 1 ml 5-Bromo-4-chloro-3-indoxyl beta-D-glucuronide cyclohexylammonium salt (50 mg/ml in DMSO)). Tissues were vacuum infiltrated for 20 minutes at −20 psi and incubated overnight at 37° C.

Incubated tissues were destained and washed 30 minutes each in 20%, 35%, and 50% ethanol, then fixed for 30 minutes in 5% fromalin, 10% acetic acid, 50% ethanol. Tissues were then washed once for 30 minutes in 10% acetic acid, 50% ethanol and then 30 minutes in 70% ethanol. The stained tissue samples were stored at 4° C. in 70% ethanol. The degree of GUS staining of harvested tissues was scored by visual comparison. The relative degree of GUS staining for different tissues from each transgenic soybean plant are shown in Table 12.

The data in Table 12 indicate that the AR10 promoter is capable of driving expression of a heterologous protein in wounded tissue. Therefore, the AR10 promoter is useful for driving expression of pest control proteins, such as insecticidal toxins from *Bacillus thuringensis*, or any other protein readily evident to one skilled in the art. A promoter capable of driving an RNAi or an antisense message with the purpose of manipulating plant or pest gene expression will prevent feeding site formation or maturation of the pest. For pests that elicit a wound response from soybean plants, a specific wound inducible promoter may be preferred over a constitutive promoter in order to express pest proteins at only the sites of interaction between the pest and soybean plant tissue, and therefore keep gene-manipulation techniques from affecting non-wounded portions of the plant.

Any application where a wound responsive specific promoter is required or preferred will find this application useful. The skilled person will recognize that there are other obvious applications for the AR10 wound-inducible promoter, such as in other studies of wound causing interactions, like those caused by herbivores or environmental factors.

TABLE 12

Degree of GUS staining in tissue types.

| T0 Plant No. | root | stem | petiole | petiole stem | leaf | flower | meristem | wounded |
|---|---|---|---|---|---|---|---|---|
| 1 | 0 | 2 | 0 | 2 | 4 | 1 | 1 | 4 |
| 2 | 0 | ND | 0 | ND | 0 | ND | ND | 0 |
| 3 | 0 | 6 | ND | 2 | 2 | 0 | 1 | 5 |
| 4 | 0 | ND | 1 | 2 | 1 | ND | ND | 6 |
| 5 | 0 | 0 | 0 | 0 | 2 | 0 | 0 | 4 |
| 6 | 0 | ND | 0 | ND | 0 | 0 | ND | 2 |
| 7 | 0 | 6 | 1 | 1 | 2 | 2 | 3 | 6 |
| 8 | 0 | 6 | 2 | 3 | 1 | ND | 1 | 5 |
| 9 | ND | ND | ND | ND | ND | ND | ND | ND |

0 = no staining,
1 = very light staining,
2 = light staining,
3 = medium light staining,
4 = medium dark staining,
5 = dark staining,
6 = very dark staining,
ND = no data

REFERENCES

Abel et al., Science, 232:738 (1986).
Aharoni et al., Plant Cell, 5:613 (200).
Altschul et al. Nucleic Acids Res., 25:3389 (1997).
Altschul et al., J. Mol. Biol., 215:403 (1990).
An et al., EMBO J., 4:277 (1985).
Aoyama et al., Plant Journal, 11:605 (1997).
AtMas, et al, Plant Mol. Biol., 2:335 (1983).
Auch & Reth, Nucleic Acids Research, 18:6743 (1990).
Ballas et al., Nucleic Acids Res., 17:7891 (1989).
Bansal et al., Proc. Natl. Acad. Sci. USA, 89:3654 (1992).
Barkai-Golan et al., Arch. Microbiol., 116:119 (1978).
Barton et al., Plant Physiol., 85:1103 (1987).
Batzer et al., Nucleic Acid Res., 19:5081 (1991).
Beals et al., Plant Cell, 9:1527 (1997).
Belanger et al., Genetics, 129:863 (1991).
Bernal-Lugo and Leopold, Plant Physiol., 98:1207 (1992).
Bevan et al., Nucl. Acids Res., 11:369 (1983).
Bevan et al., Nature, 304:184 (1983).
Bevan, Nucl. Acids Res., 12:8711 (1984).
Bird et al., Plant Molecular Biology, 11:651 (1988).
Bisaro, Homologous Recomb. Gene Silencing Plants, pp. 219-70, Paszkowski & Jerzy (eds.) (1994).
Blackman et al., Plant Physiol., 10:225 (1992).
Blochlinger & Diggelmann, Mol Cell Biol, 4:2929 (1984).
Bol et al., Ann. Rev. Phytopath., 28:113 (1990).
Bouchez et al., EMBO J., 8:4197 (1989).
Bouchez et al., EMBO Journal, 8:4197 (1989).
Bourouis et al., EMBO J., 2:1099 (1983).
Bowler et al., Ann. Rev. Plant Physiol., 43:83 (1992).
Branson and Guss, Proc. North Central Branch Entomological Society of America (1972).
Broakgert et al., Science, 245:110 (1989).
Brown et al., PNAS USA, 97:262 (200).
Byrne et al. Plant Cell Tissue and Organ Culture, 8:3 (1987).
Callis et al., Genes and Develop., 1:1183 (1987).
Callis et al., J. Biol. Chem., 265:12486 (1990).
Campbell and Gown', Plant Physiol., 92:1 (1990).
Castrsana et al., EMBO J., 7:1929 (1988).
Chandler et al., Plant Cell, 1:1175 (1989).
Chee et al. Plant Physiol., 91:1212 (1989).
Chee et al., Methods Mol. Biol., 44:101 (1995).
Christou et al. Proc. Natl. Acad. Sci. USA, 86:750 (1989).
Christou et al., Biotechnology, 9:957 (1991).
Christou et al., Plant Physiol., 87:671 (1988).
Coe et al., In: Corn and Corn Improvement, Sprague et al. (eds.) pp. 81-258 (1988).
Cordero et al., Plant J., 6:141 (1994).
Corpet et al. Nucleic Acids Res., 16:10881 (1988).
Coxson et al., Biotropica, 24:121 (1992).
Crameri et al., Nature Biotech., 15:436 (1997).
Crameri et al., Nature, 391:288 (1998).
Crossway et al., BioTechniques, 4:320 (1986).
Cuozzo et al., Bio/Technology, 6:549 (1988).
Cutler et al., J. Plant Physiol., 135:351 (1989).
Czako et al., Mol. Gen. Genet., 235:33 (1992).
Czapla and Lang, J. Econ. Entomol., 83:2480 (1990).
Datta et al., Bio/Technology, 8:736 (1990).
Davies et al., Plant Physiol., 93:588 (1990).
Dayhoff et al., Atlas of Protein Sequence and Structure, Natl. Biomed. Res. Found., Washington, C.D. (1978).
De Blaere et al., Meth. Enzymol., 143:277 (1987).

De Block et al. Plant Physiol., 91:694 (1989).
De Block et al., EMBO Journal, 6:2513 (1987).
Della-Cioppa et al., Plant Physiology, 84:965-968 (1987).
Dellaporta et al., in Chromosome Structure and Function, Plenum Press, 263-282 (1988).
Dennis et al., Nucleic Acids Res., 12:3983 (1984).
Depicker et al., Plant Cell Reports, 7:63 (1988).
DeRisi et al., Science, 278:680 (1997).
Desprez et al., Plant J., 14:643 (1998).
Diekman & Fischer, EMBO, 7:3315 (1988).
Duggan et al., Nat. Genet., 21:10 (1999).
Dunn et al., Can. J. Plant Sci., 61:583 (1981).
Dure et al., Plant Mol. Biol., 12:475 (1989).
Eisen et al., PNAS USA, 95:14863 (1998).
Ellis et al., EMBO Journal, 6:3203 (1987).
Elroy-Stein et al., Proc. Natl. Acad. Sci. U.S.A., 86:6126 (1989).
English et al., Plant Cell, 8:179 (1996).
Erdmann et al., J. Gen. Microbiol., 138:363 (1992).
Everett et al., Bio/Technology, 5:1201 (1987).
Fitzpatrick, Gen. Engineering News, 22:7 (1993).
Franken et al., EMBO J., 10:2605 (1991).
Fromm et al., Nature (London), 319:791 (1986).
Fromm et al., Bio/Technology, 8:833 (1990).
Gallie et al., Nucleic Acids Res., 15:3257 (1987).
Gallie et al., The Plant Cell, 1:301 (1989).
Gan et al., Science, 270:1986 (1995).
Gatehouse et al., J. Sci. Food Agric., 35:373 (1984).
Gatz, Current Opinion in Biotechnology, 7:168 (1996).
Gatz, Annu. Rev. Plant Physiol. Plant Mol. Biol., 48:89 (1997).
Gelfand, eds., PCR Strategies Academic Press, New York (1995).
Gelvin et al., Plant Molecular Biology Manual, (1990).
Giege et al., Plant J., 15:721 (1998).
Gordon-Kamm et al., Plant Cell, 2:603 (1990).
Goring et al, PNAS, 88:1770 (1991).
Graham et al., Biochem. Biophys. Res. Comm., 101:1164 (1981).
Graham et al., J. Biol. Chem., 260:6555 (1985).
Graham et al., J. Biol. Chem., 260:6561 (1985).
Gritz et al., Gene, 25:179 (1983).
Gruber, et al., Vectors for Plant Transformation, in: Methods in Plant Molecular Biology & Biotechnology" in Glich et al., (Eds. pp. 89-119, CRC Press, 1993).
Guerineau et al., Mol. Gen. Genet., 262:141 (1991).
Guerrero et al., Plant Mol. Biol., 15:11 (1990).
Gupta et al., PNAS, 90:1629 (1993).
Haines and Higgins (eds.), Nucleic Acid Hybridization, IRL Press, Oxford, U. K. Hammock et al., Nature, 344:458 (1990).
Hemenway et al., EMBO Journal, 7:1273 (1988).
Henikoff & Henikoff, Proc. Natl. Acad. Sci. USA, 89:10915 (1989).
Hiei et al., Plant J., 6:271 (1994).
Higgins et al., CABIOS, 5:151 (1989).
Higgins et al., Gene, 73:237 (1988).
Hilder et al., Nature, 330:160 (1987).
Hinchee et al. Bio/Technology 6:915 (1988).
Hoekema, In: The Binary Plant Vector System. Offset-drukkerij Kanters B. V.; Alblasserdam (1985).
Huang et al., CABIOS, 8:155 (1992).
Hudspeth & Grula, Plant Molec. Biol., 12, 579 (1989).
Hughes et al., J. Mol. Biol., 296:1205 (200).
Ikeda et al., J. Bacteriol., 169:5612 (1987).
Ikuta et al., Biotech., 8:241 (1990).
Ingelbrecht et al., Plant Cell, 1:671 (1989).
Innis et al., PCR Protocols: A Guide to Methods and Applications, Academic Press, Inc., San Diego, Calif. (1990).
Innis and Gelfand, eds., PCR Methods Manual (Academic Press, New York) (1999).
Innis et al., eds., PCR Protocols: A Guide to Methods and Applications (Academic Press, New York (1995).
Jefferson et al, EMBO J, 6: 3901-3907 (1987).
Jobling et al., Nature, 325:622 (1987).
John et al., Proc. Natl. Acad. Sci. USA, 89:5769 (1992).
Johnson et al., PNAS USA, 86:9871 (1989)
Joshi et al., Nucleic Acid Res., 15:9627 (1987).
Kaasen et al., J. Bacteriol., 174:889 (1992).
Kagaya et al., Nucleic Acids Res., 27:470 (1999).
Karlin and Altschul, Proc. Natl. Acad. Sci. USA, 87:2264 (1990).
Karlin and Altschul, Proc. Natl. Acad. Sci. USA, 90:5873 (1993).
Karsten et al., Botanica Marina, 35:11 (1992).
Katz et al., J. Gen. Microbiol., 129:2703 (1983).
Kehoe et al., Trends Plant Sci., 4:38 (1999).
Keller et al., EMBO Journal, 8:1309 (1989).
Keller et al., Genes Dev., 3:1639 (1989).
Klein et al., Nature, 327:70 (1987).
Klein et al., Bio/Technology, 6:559 (1988).
Klein et al., Plant Physiol., 91:440 (1988).
Klein et al., Proc. Natl. Acad. Sci. USA, 85:4305 (1988).
Knauf, et al., Genetic Analysis of Host Range Expression by Agrobacterium In: Molecular Genetics of the Bacteria-Plant Interaction, Puhler, A. ed., Springer-Verlag, New York, 1983.
Koehl P. and Delarue M., Curr. Opin. Struct. Biol., 6:222 (1996).
Kohler et al., Plant Mol. Biol., 29:1293 (1995).
Koster and Leopold, Plant Physiol., 88:829 (1988).
Koziel et al., Biotechnology, 11:194 (1993).
Kridl et al., Seed Science Research, 1:209 (1991).
Kriz et al., Mol. Gen. Genet., 207:90 (1987).
Kunkel et al., Methods in Enzymol., 154:367 (1987).
Kunkel, Proc. Natl. Acad. Sci. USA, 82:488 (1985).
Lam et al., Plant Cell, 1:1147 (1989).
Landolt, Biosystematic Investigation on the Family of Duckweeds: The family of Lemnaceae—A Monograph Study. Geobatanischen Institut ETH, Stiftung Rubel, Zurich (1986).
Langridge et al., Proc. Natl. Acad. Sci. U.S.A., 86:3219 (1989).
Langridge et al., Cell, 34:1015 (1983).
Lashkari et al., PNAS USA, 94:8945 (1997).
Laufs et al., PNAS, 87:7752 (1990).
Lawton et al., Mol. Cell. Biol., 7:335 (1987).
Lee and Saler, J. Bacteriol., 153 (1982).
Lesyng B. and McCammon J A, Pharmocol. Ther., 60:149 (1993).
Levings, Science, 250:942 (1990).
Lindsey et al., Transgenic Research, 2:3347 (1993).
Lindstrom et al., Der. Genet., 11:160 (1990).
Lockhart et al., Nat. Biotechnol, 14:1649 (1996).
Lockhart and Winzeler, Nature, 405:827 (200).
Lommel et al., Virology, 181:382 (1991).
Loomis et al., J. Expt. Zool., 252:9 (1989).
Lyznik et al., Nucleic Acids Res., 21:969 (1993).
Ma et al., Nature, 334:631 (1988).
Macejak et al., Nature, 353:90 (1991).
Maki et al., Methods in Plant Molecular Biology & Biotechnology, Glich et al., 67-88 CRC Press, (1993).
Maleck et al., Nat. Genet., 26:403 (200).
Mansson et al., Gen. Genet., 20:356 (1985).

Mariani et al, Nature, 347:737 (1990).
Martinez et al., J. Mol. Biol., 208:551 (1989). McBride et al., Plant Molecular Biology, 14:266 (1990).
McBride et al., PNAS USA, 91:7301 (1994).
McCabe et al., Bio/Technology, 6:923 (1988).
McElroy et al., Mol. Gen. Genet., 231:150 (1991).
Meinkoth and Wahl, Anal. Biochem., 138:267 (1984).
Messing and Vierra, Gene, 19:259 (1982).
Michael et al., J. Mol. Biol., 26:585 (1990).
Mogen et al., Plant Cell, 2:1261 (1990).
Moore et al., J. Mol. Biol., 272:336 (1997).
Mundy and Chua, EMBO J., 7:2279 (1988).
Munroe et al., Gene, 91:151 (1990).
Murakami et al., Mol. Gen. Genet., 205:42 (1986).
Murata et al., FEBS Lett., 296:187 (1992).
Murdock et al., Phytochemistry, 29:85 (1990).
Murray et al., Nucleic Acids Res., 17:477 (1989).
Myers and Miller, CABIOS, 4:11 (1988).
Napoli et al., Plant Cell, 2:279 (1990).
Narasimhulu et al, Plant Cell, 8: 873-886, (1996).
Needleman and Wunsch, J. Mol. Biol., 48:443-453 (1970).
Newman et al., Plant Physiol., 106:1241 (1994).
Niedz et al., Plant Cell Reports, 14:403 (1995).
Odell et al., Mol. Gen. Genet., 113:369 (1990).
Odell et al., Homologous Recomb. Gene Silencing Plants, 219-70, Paszkowski & Jerzy (eds) (1994).
Odell et al., Nature, 313:810 (1985).
Ohtsuka et al., J. Biol. Chem., 260:2605 (1985).
Ow et al., Science, 234:856 (1986).
Pacciotti et al., Bio/Technology, 3:241 (1985).
Park et al., J. Plant Biol., 38:365 (1985).
Paszkowski et al., EMBO J., 3:2717 (1984).
Pear et al., Plant Molecular Biology, 13:639 (1989).
Pearson and Lipman, Proc. Natl. Acad. Sci., 85:2444 (1988).
Pearson et al., Meth. Mol. Biol., 24:307 (1994).
Perlak et al., Proc. Natl. Acad. Sci. USA, 88:3324 (1991).
Phillips et al., In Corn & Corn Improvement, 3rd Edition 10 Sprague et al. (Eds. pp. 345-387)(1988).
Phi-Van et al., Mol. Cell. Biol., 10:2302 (1990).
Piatkowski et al., Plant Physiol., 94:1682 (1990).
Potrykus, Trends Biotech., 7:269 (1989).
Poulsen et al., Mol. Gen. Genet., 205:193 (1986).
Prasher et al., Biochem. Biophys. Res. Comm., 126:1259 (1985).
Proudfoot, *Cell*, 64:671 (1991).
Quigley et al., J. Mol. Evol., 29:412 (1989).
Ralston et al., Genetics, 119:185 (1988).
Reed et al., J. Gen. Microbiol., 130:1 (1984).
Reina et al., Nucleic Acids Res., 18:6425 (1990).
Reina et al., Nucleic Acids Res., 18:7449 (1990).
Reymond et al., Plant Cell, 12:707 (200).
Richmond et al., Curr Opin Plant Biol., 3:108 (200).
Riggs et al., Proc. Natl. Acad. Sci. USA, 83:5602 (1986).
Rossi et al., Biophys. J., 80:480 (201).
Rossolini et al., Mol. Cell. Probes, 8:91 (1994).
Rothstein et al., Gene, 53:153 (1987).
Ruiz, Plant Cell, 10:937 (1998).
Safak et al., Mol. Cell. Biol., 19:2712 (1999).
Sambrook et al., Molecular Cloning: A Laboratory Manual (2d ed., Cold Spring Harbor Laboratory Press, Plainview, N.Y.) (1989).
Sanfacon et al., Genes Dev., 5:141 (1991).
Sanford et al., Particulate Science and Technology, 5:27 (1987).
Schaffer et al., Curr Opin Biotechnol., 11: 162 (200).
Schena et al., Science, 270:467 (1995).
Schenk et al., PNAS USA, 97:11655 (200).
Schmidhauser and Helinski, J. Bacteriol., 164:446 (1985).
Schwob et al., Plant J., 4:423 (1993).
Shagan et al., Plant Physiol., 101:1397 (1993).
Shapiro, Mobile Genetic Elements, Academic Press, N.Y. (1983).
Shimamoto et al., Nature, 338:274 (1989).
Simpson, Plant Mol. Biol., 19:699 (1985).
Skriver and Mundy, Plant Cell, 2:503 (1990).
Skuzeski et al., Plant Molec. Biol. 15: 65-79 (1990).
Slater et al., Plant Mol. Biol., 5:137 (1985).
Smith et al., Adv. Appl. Math., 2:482 (1981).
Smith et al., Mol. Gen. Genet., 224:447 (1990).
Smith et al., Planta, 168:94 (1986).
Southern et al., Nature Genet., 21:5-9 (1999).
Spencer et al., Theor. Appl. Genet, 79:625 (1990).
Stalker et al., Science, 242:419 (1988).
Staub et al., EMBO J., 12:601 (1993).
Staub et al., Plant Cell, 4:39 (1992).
Steifel et al., The Plant Cell, 2:785 (1990).
Stemmer, Nature, 370:389 (1994).
Stemmer, Proc. Natl. Acad. Sci. USA, 91:10747 (1994).
Stief et al., Nature, 341:343 (1989).
Stouggard, The Plant Journal, 3:755 (1993).
Sukhapinda et al., Plant Mol. Biol., 8:209 (1987).
Sullivan et al., Mol. Gen. Genet., 215:431 (1989).
Surles et al., Protein Sci., 3:198 (1994).
Sutcliffe, PNAS USA, 75:3737 (1978).
Svab et al., Proc. Natl. Acad. Sci. USA, 87:8526 (1990).
Svab et al., Proc. Natl. Acad. Sci. USA, 90:913 (1993).
Tamayo et al., PNAS USA, 96:2907 (1999).
Tarczynski et al., PNAS USA, 89:260 (1992).
Thillet et al., J. Biol. Chem., 263:1250 (1988).
Thompson et al., EMBO J, 6:2519 (1987).
Tijssen, Laboratory Techniques in Biochemistry and Molecular Biology-Hybridization with Nucleic Acid Probes, Elsevier, N.Y. (1993).
Tomes et al., Plant Cell, Tissue and Organ Culture: Fundamental Methods, Springer Verlag, Berlin (1995).
Tomic et al., NAR, 12:1656 (1990).
Tremousaygue et al., Plant J., 20:553 (1999).
Turner et al., Molecular Biotechnology, 3:225 (1995).
Twell et al., Plant Physiol., 91:1270 (1989).
Ugaki et al., Nucl. Acids Res., 19:371 (1991).
Ulmasov et al., Plant Mol. Biol., 35:417 (1997).
Upender et al., Biotechniques, 18:29 (1995).
Vaeck et al., Nature, 328:33 (1989).
van der Krol et al., Plant Cell, 2:291 (1990).
vanTunen et al., EMBO J., 7:1257 (1988).
Vasil et al., Biotechnology, 11:1553 (1993).
Vasil et al., Mol. Microbiol., 3:371 (1989).
Vasil et al., Plant Physiol., 91:1575 (1989).
Vernon and Bohnert, EMBO J., 11:2077 (1992).
Vodkin, Prog. Clin. Biol. Res., 138:87 (1983).
Vogel et al., EMBO J., 11:157 (1992).
Walker and Gaastra, eds., Techniques in Molecular Biology, MacMillan Publishing Company, New York (1983).
Wandelt et al., Nucleic Acids Res., 17:2354 (1989).
Wang et al., Mol. Cell. Biol., 12:3399 (1992).
Waterman, M. S. Introduction to Computational Biology: Maps, sequences and genomes. Chapman & Hall. London (1995).
Watson et al., Corn: Chemistry and Technology (1987).
Watrud et al., in Engineered Organisms and the Environment (1985).
Weeks et al., Plant Physiol., 102:1077 (1993).
Weissinger et al., Annual Rev. Genet., 22:421 (1988).
Wenzler et al., Plant Mol. Biol., 13:347 (1989).

White et al, Nucl Acids Res, 18, 1062 (1990).
Wolter et al., EMBO Journal, 11:4685 (1992).
Wyn-Jones and Storey, Physiology and Biochemistry of Drought Resistance in Plants, Paleg et al. (eds.), pp. 171-204 (1981).
Xiang and Guerra, Plant Physiol., 102:287 (1993).
Yamaguchi-Shinozaki et al., Plant Cell Physiol., 33:217 (1992).
Yamamoto et al., Nucleic Acids Res., 18:7449 (1990).
Yanagisawa and Schmidt, Plant J., 17:209 (1999).
Yanagisawa et al., Plant J., 21:281-288 (200).
Yuan et al., Plant J., 15:821 (1998).
Zhang et al., Proc. Natl. Acad. Sci. USA, 94:4504 (1997).
Zhu et al., Nat. Biotechnol., 18:555-558 (200).
Zhu et al., Plant Physiol., 124:1472 (200).
Zhu et al., Proc. Natl. Acad. Sci. USA, 96:8768-8773 (1999).
Zukowsky et al., PNAS USA, 80:1101 (1983).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

TABLE 13

| Promoter | SEQ ID No. | Expression Specificity |
| --- | --- | --- |
| 1B_syn299 | 1 | Constitutive |
| 1G2_syn300 | 2 | Constitutive |
| AC11_syn271 | 3 | Constitutive |
| AC12_syn272 | 4 | Constitutive |
| AC13_syn273 | 5 | Constitutive |
| AC20_syn278 | 6 | Constitutive |
| AC22_syn280 | 7 | Constitutive |
| AC24_syn282 | 8 | Constitutive |
| AC26_syn284 | 9 | Constitutive |
| AC31_syn286 | 10 | Constitutive |
| AC34_syn288 | 11 | Constitutive |
| AC38_syn290 | 12 | Constitutive |
| AC40_syn292 | 13 | Constitutive |
| AC7_syn267 | 14 | Constitutive |
| AC9_syn269 | 15 | Constitutive |
| AF3_syn312 | 16 | Fuitless |
| AR10_syn307 | 17 | Inducible by wounding |
| AR13_syn309 | 18 | Root-specific |
| AR1_syn301 | 19 | Root-specific |
| AR2_syn302 | 20 | Root-specific |
| AR5_syn303 | 21 | Root-specific |
| AR6_syn304 | 22 | Root-specific |
| AR8_syn305 | 23 | Root-specific |
| ATU56929_syn007 (AC32) | 24 | Constitutive |
| PR1_Syn018 | 25 | Inducible by SA, NA, BTJ, pathogens |
| UBQ3_Syn016 | 26 | Constitutive |

What is claimed is:

1. An isolated polynucleotide comprising a nucleotide sequence that directs transcription of an operably linked nucleic acid segment in a plant cell, wherein the nucleotide sequence is operably linked to a heterologous nucleic acid segment, and wherein said nucleotide sequence is SEQ ID NO: 11.

2. An expression cassette comprising the polynucleotide of claim 1, wherein the heterologous nucleic acid segment is an open reading frame.

3. The expression cassette of claim 2, wherein the open reading frame comprises a coding sequence which, when transcribed at the direction of the nucleotide sequence, imparts a phenotype selected from the group consisting of insect resistance, disease resistance, herbicide resistance, abiotic stress resistance, a modified enzyme expression profile, a modified oil content, and a modified nutrient content.

4. A transformed plant, the genome of which comprises the expression cassette of claim 3.

5. A cell of the transformed plant of claim 4.

6. The transformed plant of claim 5, wherein the plant is a monocot or a dicot plant.

7. The transformed monocot plan of claim 6, wherein the plant is a cereal plant.

8. The cereal plant of claim 7, wherein the plant s selected from the group consisting of maize, wheat, rice, sorghum, and barley.

9. The transformed dicot plant of claim 6, wherein the dicot is selected from the group consisting of soybean, cotton, canola, and sugarbeet.

10. An isolated polynucleotide sequence comprising SEQ ID NO: 9.

\* \* \* \* \*

SEQUENCE LISTING

```
<160> NUMBER OF SEQ ID NOS: 34

<210> SEQ ID NO 1
<211> LENGTH: 1270
<212> TYPE: DNA
<213> ORGANISM: Arabidopsis sp.

<400> SEQUENCE: 1
tacaaatcca aagagattcc agatgaagta aagaagttgt gccttatgct gatccaaacg      60
acagagatgt cgttatactt ggaactctgt gtagttcagg tttgcaggat ccatcctgta     120
tttgggcgtg tggataactt ctccaaagac ttgaaaaaac tagtgaaagg taacaagtgt     180
ttcttccata gtaatattga caagactatt ttgggatttg gtgcctttt taaaatacga      240 tttagttgca aggaaaaagt gaaaacggtt tcgtaacatt gctgcttctt ttgttttgtc     300
tcgatcagct gctgaggtgc atacctactt agaaccgtcc atagattcac tgaagaaaat     360
agctgcgttt ctgtatcctg gatcacttta gaaacaaaac aaacatgagg accatgcttg     420
aatgtggtac gtatgtatta gattccttcc ttgatgagtg attaaaccgg ctattgtacc     480
attggtatat gttagtcata taatagtatt attctcttta tttcatatca tagctttaaa     540
aaaatgttcg gctcatgctg tccactcctt ttgggccgct cgttgctttc attttttaa     600 attgcttacc tctcaacaaa ttcttttgat tggttctctc tctgactcta ggccgcagaa     660
agtgcagttc cgaataattc tcactcaact aacttttgat aatcacttat tctagattat     720 tctgatttt gaattccctc tactcttgaa cacgtttact tactatgagg aaaaatttaa      780
ccctaaaaag aaaaccactc attacagcta acatctatga ggggtggact attgcgcaaa     840
gcattgatag tgttaattga aagtcatgca tatagtatgc gttactacta aagtttaacg     900
gttcaatttt tttgaatttg aactgacagt aaataaaatt aatttttaag attaaaagac     960
gttgttttta gcaagttgtt tagaaattgt gggacacgtg tggcacgttg ctccaggagg    1020
```

```
ggcatatgcc aagtctgaga tactccaacg cactgactga ctgaccccta cttaaccggt    1080
ggtcaaactc ttaacctaac cacggttaag atcttaaagc cgttgagatt ttcccacatg    1140
taataatctt gtttatctgt gagatattcg ccgcttcccc ttggccggct ataaatcgat    1200
aacctcaccg ataaatcctc tattcatcat ccacaacaaa cctcttcttc agtctgatag    1260
agatctcacg                                                           1270

<210> SEQ ID NO 2
<211> LENGTH: 1116
<212> TYPE: DNA
<213> ORGANISM: Arabidopsis sp.

<400> SEQUENCE: 2
cctcagcaaa taagaggacg ataaggatcg gtcttcagct ataaacaagt aaagaaagtt      60
gagattcgaa gactctttat aagtcattgg atttgtagta ataacaaat taacaacaca     120 acaaattaac aacacatata ctacaaattc gagttaaaaa ccccaatata atatatgcat     180
cgactactaa acgcgtttca atgactggta acatatgta actatctctg ttacatattg     240
aatgaatgat gatgtaatag tagatgctaa cataagctca caattatttg aataattaaa     300
gtcataaata aaaatcatct ataatgcgtg taagcttgca taaaaataca gtatataact     360
tttatttaaa actattaagt atcaacatca atcggaaaat gatttgcttt tgaagttatt     420
acaactagtt tattaaaaaa attgttatca tcatctcgat tttaataatg ctatatatac     480
ttagtctttt atttattgtt attgtaatat gcgaaaatga cttgcaactg agttgcttac     540
gggcaaacct gaccaagatg tgggaagttc gaaactgcaa atatgtataa ttcttaataa     600
aaaaaaaata tatcctacat ttcttcattt ttttttttaaa atactaatat ttgcatactt     660
tgttgattga gtttctgaaa aatcataatt gagtttttaa attagttggt ttgtatgcat     720
ttgcaacttc ccaatttctt ttaaatatat cacttttcat atattcttgt agagctataa     780
ttttacaaca ataattgaaa tgtcgaccca aaaatataca tttaaaggca tttcgctgat     840
aaaaatccag tttagatgta tttgtattat agggggaaacc aattatatta ttggttaata     900
tttattagtc gatattgggt acatatgtat gttcttttac gattatgcca tcaaaaaatt     960
tattagccat tcgagaaaca aggcatctct atttttttgc ttcttctaat agacttcttc    1020
gtcactgatc tcccacgacg atctcccaaa ctcatttctc tacgttcatc gatctctctc    1080
tttctcgttt gctctacgaa aatcagccgt ttaaac                              1116

<210> SEQ ID NO 3
<211> LENGTH: 1358
<212> TYPE: DNA
<213> ORGANISM: Arabidopsis sp.
<220> FEATURE:
<221> NAME/KEY: misc_feature
<222> LOCATION: (979)..(979)
<223> OTHER INFORMATION: n is a, c, g, or t

<400> SEQUENCE: 3
ttaagtgatg tttgcaactt ttaatgcaac atttttttcc agcatatttt ataattggtt      60
gaaacaattt aatttaattt aaatttggtg ttttcttaac ttgtatataa aaaccttaaa     120
tgtcaattga aatgatagag agagacatta ctatattatt gtgaaaaagt atcactattt     180
ctaaagaatt gttctagtaa aaattggtat tagttaattt tcagaccatc ataaaaagat     240
gatttagatt agtgacaaag aataatcctt caaaaataca tatttcgaca caagtatact     300
tggtatcaaa atctgtaaaa aaaaaatcag agccatgacc aaatacaata tgttaagttc     360
```

```
atgtgacgtg agataataaa ttgatttgat tcactttcca attgtgttta taattaacgc    420
attaaaaaca ctaaaaagca aataaataaa tgtagccgaa taagccgatg gaagtaagaa    480
ttgaagtcca aaagcaaaaa cctatagatc cggtggacag tcaacagtgt catttaatcc    540
ctataaatag ctcactccct tgtcatccac aaatcgtccc cgtctcgttt ccttcttcgc    600
tcgctgttca gattttgctt tgaggcttta ggctccccag atctctaatc gccgcaggtt    660
tcgctcttct tctccgtctt attgatttcg agttttagg cgatgctttt acgggttttg     720
ttgttaaatc tgaaacgaaa tgagattttt ctatgggttt cgattcagat ttgataatat    780
tcgaaccttc tacgcctgtt attataatta gatctgcgat agtgtgtgac tattgaaatg    840
agattctcaa gttcttaggt tatatcgttt gtgatttata cagatttaaa acgtatgtgg    900
atccgttaat tttccagtgc tgtgtagcag atctgcttaa taggtttatc ttttttgcaa    960
atgattttga ttttcgcanc gatcgtgtac tctatgtagt agtagtagta tatgatttga   1020
taaatgtagt agtagtagta tatgatcgtg tactgagcca taaatgagcc ttcctcgtta   1080
attattgtcc atgaattgtt agttaagctt gaaagttcct taaacgttta attagatcct   1140
tatcactgac tgttccacta tgaatatcag aagaatcgaa tctctttgga tgagatgcgt   1200
ctgtttttat gctattccac aatgatttgg aatctttctt agcttttat gtcacttgag    1260 tgtggaatct ttttttttg ttctcttcct ttcaattgta aaagtttgt tatatgtgta     1320 tgattttat gtggttgctg attcaatttt tctttttg                            1358

<210> SEQ ID NO 4
<211> LENGTH: 1301
<212> TYPE: DNA
<213> ORGANISM: Arabidopsis sp.

<400> SEQUENCE: 4
tgtggagatc agtgcctgat aaagatagca ttgcaatgat aatgtatgat gtgcaacgca     60
taagacaaca attgacatca agcacacctc ttctggtgac tggaaatcaa actaataagt    120
tagcttatga acttgcacta gaaacactag tttcagaaat cagcataagt atcgaagaga    180
aagctctaac atgtgacaaa aattaaacgt ggaaagtacg taagctgcag gtatcatctc    240
taatcacatt ctctagactc tagctactat acattaattt taatttatcg tcgtggaatg    300
ttgattatgt ttacgcctaa tgttgtaatt tcatggttga tggatatata tagatgtggg    360
tattcctttt gctatatgtg tggagtcgaa tggaaacaac ggctaggagc tggtggttgc    420
attcatagca aagcagagat ttattttatc attatttgtt ttgcagtctt gtttggagtg    480
aacttttgtt tctttttgat tgctactttta atcaattggg ttgtgaattt attcaagtga   540
tttacccaga gacttgtaaa cgggacataa aaagaaataa aacctttcat ttctatgtct    600
tatgattgca tgagtagccc aaacatctat ggtctagtgg taggagaaga tttagggaat    660
agtgaaactt gtagatccga gttcgatcct ccctgaaaac aaaaatcata tttgttttga    720
gaagtctctc agttaggcct tgggtcaatt ggtttacctg gtagttagaa atgcagccgg    780
tctgactatc ccctttcatt agtcggaaaa catttcaaat tcagaacaga cagtatggta    840
gtccttcggt gagaagtcca ctctaaaata tttcggtgcg tttctgccga ggctgaccag    900
attagccggt agggtttatc aaaaaaaaag aaaaaatgat tgcatgagta cttctcaatt    960
cttcacgttg tcacaacaac ttgttacatg cgactaaaca aattatattg aatccatata   1020
cagatttgcc aaatactatt tctatttggt cccaattagt gatgtttata tggatttaat   1080
agcccattta gttatatggg tctgttgtta aaaaatagcc catgtagacc cgtttatgga   1140
```

| | |
|---|---|
| aaaagataaa tgggctttaa tttcgacccg gcccaaaatt acaacgtgtt caacaacaac | 1200 |
| tctattatac aaacagacta cgtcgttctc ttccactcat ctgaaaacaa atccaattc | 1260 |
| tctctctctc cctccagatt caaacgatcc gatccaaaac t | 1301 |

<210> SEQ ID NO 5
<211> LENGTH: 1368
<212> TYPE: DNA
<213> ORGANISM: Arabidopsis sp.

<400> SEQUENCE: 5

| | |
|---|---|
| acccatttgt ctgccaacat ctcttttggc tatatactca tgaaacttta aaaaatcttc | 60 |
| ttatttgtat gttcgaaact ccctgaaagt ttcagtcttc ttatgtatga caagaatcgc | 120 |
| gagagactat gcaatgaacc taatcaaata taactcttct caagaaatga tatgaaaaag | 180 |
| attcatgaac ataagagttg gtccttggaa agcgacctct tcaagtcttc attaattaga | 240 |
| cattgattca ggtgcttagg agttaggaca atgtaaatta ataaacaaag gtggtgctta | 300 |
| aggcggtcca tgacgttgta gaaagtattt ttttttcgta taagccgact atatacatat | 360 |
| gtgtttttca tttacttatc gcaaataaga aacacacact aatcaactat ttgtaaattc | 420 |
| aaattcacca aaattattta tgttatatgt tgaacctacg aaactcatag acacagaata | 480 |
| aaacataagt gaaagactg aattaaacac ttacttataa gtgaaagac tgaattaaaa | 540 |
| taacaaagaa ttatcaatag tattttaat aaaattaaac atttaaaaaa taaacttatt | 600 |
| tgaggacgta acctaaaaat ctctatatag ttgttttga cgaatatgag ttttattata | 660 |
| agactaattt ttccaagaga taaatttata aaaaatatta aatacgtaat attttttaac | 720 |
| tccaataaaa tattgtaatt tcaaaccaaa tatttattaa ttaaaatgtg taatgagata | 780 |
| cttacatatc atctagacaa gttgagattt tctttatagg gttttgtaaa aatttgatga | 840 |
| ttttttaacaa gaagaaatcc ataggaacta ataataaaaa atacaatgca atgatatta | 900 |
| aaaaaacaac aactgcattg cagtgaattt catcaaaatc cattaaaaca tttccaaact | 960 |
| caaatagaaa caacttcaaa accttaatcc aaaatgttat agatagatat gcaatagctc | 1020 |
| ttaggcctag tacatagcta gatcttgtaa ctcgtgaagg caaatgattg ggacgttggt | 1080 |
| tcggttctag tggtcgggct cagcctggcg gaaaaaattg ttatgggtct aaggcccata | 1140 |
| aagtggccca gaaataaact cgtcgtattt acacacgttg tcgtttctct tatcttctag | 1200 |
| aaaactgtat cccgttttg ttcttgtact ctacacaaac agacaacttc aaattactca | 1260 |
| acaccacgtc gtgaaaatcc gatctacgtc tctgtctctc tccaatctct ctgcgccaca | 1320 |
| gaattgtgcg atttacgaaa atctctgaaa cctccgatcg ttaacggc | 1368 |

<210> SEQ ID NO 6
<211> LENGTH: 1399
<212> TYPE: DNA
<213> ORGANISM: Arabidopsis sp.

<400> SEQUENCE: 6

| | |
|---|---|
| cttggaagca ttcaagagag tcgtggagag tgtggctcag cgtctcaatg aacagcccgt | 60 |
| gatcgttgct cacagcgaaa acacctttga tgggagcggt atcaggaggc tcttgtccaa | 120 |
| taaattcgaa ttcgataagg taaactacca tacatatata tgttatctag cttttatgct | 180 |
| aaaggaaaac ttttaaatg atggtaacga gtgatgatga tccggaacgg tttggtcgca | 240 |
| ggcgctaaac gttgccatgg agacgattcc aaaagaccgt cagggtaagg tgtctaaagg | 300 |
| atatctacga gctgtgcttg acactgttgc accatcggcc actttaccac caataggcgc | 360 |

```
tgtgtcccag gtaaataatg ccccgtctaa attattttgt cttttaaatt gtttattttg      420
cctttgaatt tacatgttac aattatttgt taaacaaatg aaaccagaat tagtgtttta      480
atcaaaaatt attagtgaat ttttattttt atttttttgaa cggcattgat tagttaagtt     540 tgttttttgtt tataagatgg ataatatgat aatggaagcg ttgaagatgg tgaatggaga    600
tgatggaaat gtggtgaagg aagaagagtt taagaaaaca atggcagaga tattggggag      660
tataatgttg cagctcgagg gtagtcccat atcggtttcc tctaactcgg tggttcacga     720
gccgctcacc tcggctacct ttctgccgtc aacttcgact gatacagagg agccttcaaa     780
ctaatcatag aagggaataa gcagcactag cagcaacaaa tgttatatgg ttttgacttt     840
tgagtgttta cccccaaaag ttttagatta atgaggaaaa ccgtctttac tttcagatgt     900
ataaaattga agtttgggg tttcctcttg ttggtgtggt gattctactc atgccttttt     960
tttttttttt ctaatgacca tgggatgcaa tgtttactct gttttttaat ttcgttaaaa    1020
tttgtttacg tttatgatgc ttgaatggct atgatgaaac atttgagtta tcttttaaaag   1080 tgtgaaataa atattctgaa gttaattgaa gaatttgaaa atttgattac aagagcttgg    1140
ctaaaactac aaggagacca gattagtaca aaaacttagc taaatttaat taattacggt    1200
cattagcaca aaaaaataat ttgtttttat tatattatta ttggtaagtg gaaacacaaa    1260
agaggaccaa aaggtccaaa aacgaataaa ctgtatctct cattcgccgg agtttccagc    1320
cgtttctttc cgattctcgg attttcctg ggaatcaaac gcatcgccga gaatcggaag    1380
agagggataa ggtacccag                                                  1399

<210> SEQ ID NO 7
<211> LENGTH: 1283
<212> TYPE: DNA
<213> ORGANISM: Arabidopsis sp.

<400> SEQUENCE: 7
tcaccagaaa aacaaaaact agaaaccagg aaaaacttag gaaaatcata gagttaagca      60
aagttaatca acgtcattaa gttattatat ataactacat tctatataat ctctgtttcg     120
tcattgtaca ttttggtgac tggaagtttt tgtcacgtgg taaacaagaa cgtattcgcc     180
aacctaaaga ctcaatcctc tttgtctaca aattaaatac attatcacga aaaaagcttt     240
atgtattata accaaactac tttattctct caaaactatt gcattggtgt gcaaatacgt    300
tttctcgaga tgtatcatc aatcttaata tcaacttcaa cttttaaagt aaagcaaacg     360
taaattaaca cggtcgttct agctttgtag catcgaaata gttttaaatg tcaaaaaaat    420
gagcgaaata atttattctt aattatcttt gccagatttt taaaaacctt taagcatata    480
taattcaact aaaagaattt taactatttg tgactatcta gacttgaagc aaaaagtcaa    540
aaatgagtag acataactca attcctgctg ttgatccata actcaacaaa tatgtgttta   600
acaatttttt ttttggtca aacaattctt tcagttgtaa gctagaatat tacaagatag    660
atgagattaa agaaatagtc ccaaatagca agcaacaaaa ctaaacatt aacacaaaca    720 aattctaaaa tagagacaca aacttaacaa agcttgatac aatgaaacct caatgaatta    780
atactcgata tactaatacc ttaaaatatt ttttctagtt ctaaattaat aatttaacct    840
aaaaatatca cttctataaa ttaataatta cgataattta atgaaattta gtaaccatt    900 aatctcaata ttcttaattt atagaggttt tactaaattg tagaaacaac taattcgagt    960
acatccctga attaataaat tttagaaatg tgaattaacg aatactttg ttcttgtgaa    1020 tggttaaaaa aagttactta tcaagacaag tatgaagtat cacgtgatta aacgtttaat  1080
```

```
gacaccaacc taatgacaat ttgtttgatt tatttgtcac ctaactagag actctctcac    1140
agtcaacgca gcttatgtgt catagtaaga ctttttgtct actatagtag aaagacgaat    1200
ttataacccc tttaggtttt ttctaacaca cgcctctaat ctccgcgcac acacacacac    1260
cctcacgaag aagaagaaga cga                                           1283
```

<210> SEQ ID NO 8
<211> LENGTH: 1367
<212> TYPE: DNA
<213> ORGANISM: Arabidopsis sp.

<400> SEQUENCE: 8

```
tcgtgaaccc atccatattc tttgcttgac cgcttccata aacaatccac cccgaagctt     60
ttacatcgtg atgtctttgt aaatttagga aaacacagac acagttggtc aatgataatc    120
attacagatt ctaaaagaat ttggtagcca ctagtcaaag aacttaaaag gcaagattta    180
tcgggacatt aggacaaggt aaatgaatgc attataagaa aataaaaaaa cccttttaaca   240 ttttgtttaa tagaaaagaa gtagaggttg attagttatt gttaaagtaa aatgtgttgg    300
gcttgtcttt tcctcaaatg tcgcgaagct caatggtata agcgaaagag aaagcatagc    360
atgatgggcc atatataaat aaaaactcga gtatgctaca aaaacaaggt ttcaatgcac    420
tcatatctcg tttaacattt tctaatttta ttcttttcat gtgtccccca ttggcttggc    480
aataaagttg aatttgtatt gatttatatc tcattctcag tacgagctaa aattcttaat    540
taaaatgaaa aatatgctat aaacaattta aatgattgca agtcccacct tgaacaacat    600
cagttaatat ttttccgtag catgttgcat atagcataat tttggtctta agtaacacca    660
ccacctcaca cgtacgtacg accaattatg catgtctcaa atccctccat gatttctata    720
tggaagacca aggtttcaag attagcaatt ttaacggatt aaaaccggtt caagatttta    780 tttttttattt attttttgcta atcctacaa tttggtctca tgacaaaaaa aatataaaaa    840
catagaaaca ataacaatg aatctatcga catcaacaaa agcaattaaa ctttccgaat      900
caatgaagcg ataaccggta gtatcttcga gacttcatat acgatcaaaa tgctaaagta    960
actattcata atcttttatt aataatgaat tatcaaagct tctataattc atacgacaaa   1020
gacaaaggaa tagcaacaag ttatgttcat ttcgctgtcg tttaattcaa caatgaaacg   1080
ttaacgaaac gattttgtcg agatttttaa acgtcttttt caggttctac ggctaaaatt   1140
cctaacattt catcacctgt cgttatcgtt aatatcgtcc ttgtcagcag aaaaaaattg   1200
aaatcaggat aagttgataa cttctatgaa aaaacatta tcttacaaaa atccaaatac    1260
tccgacttaa ccgggtcgga tcctggtgag tactagtatc tatctcatta caattcatat   1320
ccttccttca acattcgatc atcacgaagc caaagaacaa tttctcc                 1367
```

<210> SEQ ID NO 9
<211> LENGTH: 1343
<212> TYPE: DNA
<213> ORGANISM: Arabidopsis sp.

<400> SEQUENCE: 9

```
gtgaggtcat attcaggacc gatccaacaa tattgagggt tttactccaa gtaaaatttt     60
agttttattt ttaattatca taacgacat aaatataata tggaaagatc acaaatactg    120
attaaaaact aaaatcatca aaacgaaaag gaaaaaagaa aaaattgggt tcaactctca    180
tgagttatta aacattttag gttttaggct taaatctttta aaaaaaatca gaactgaaaa   240
acgaaaaatt ctaattttat tttggactct gattcatagc ttatgtcgct tatgtagtta    300
```

```
tgctagggat gaatctgtat ttcgttaccg taatgagagt tcgatactct cttacttgtt      360
acgattctgg agcatgttac attttttcct ttccgtcaac aacaacttta atatggtaaa      420
acaaaattta ttttatttg gctggtccta ctcaagacaa atcttctgcc gacatcacat       480
aatcatatta aaaccataa cttctgccac tctgtttttt ttttttttg taaccattaa        540 ctgattggat tttgatccat ctcatctgat ttttagctc aacaatttac ttgcacattt       600
tctatttggt tttatttata cttagttaca tatatgatta tcgaactagt atctctttat      660
aattaagtat ttttctattt tttttaatt tagattttg tgaattcatt tacagtagaa        720
aactgtaaaa ccatatggtc taattataga atgaaaactt caacgaatcc atacaactta     780
ttggctaaat ataataaatc tgcttgaagc atattgttat tatttagttg gatttgacga     840
tctctgactt taatgtatac cgacataccc tatgatttag atgttgatttt tcccattct     900 taatatatcc atgttaagag attccaccat aacatatcta attatttgca ttgtaataaa     960
tattatcatt aaaaaaaat acaactggac agctggctcg tcccattgtt tcttacgtcc      1020
accaattaca tttgttaaag caaacttatt agaacgttca tgtgtgagaa gttggtgtcg     1080
acatgtgtct aaggtctatg tcagaaatcg gattagctta ttaagtaaac tatactatat     1140
cattgttaat atagataaaa tatctagttc gtccaaatta aactattttc ataactgcca    1200
cgtggcgtaa acgtatccat cgagtcactt gtaatatctt tataaccaaa gtcttccaac    1260
acattcatca ccatctatct actctttact ctcttctctt ctcacatcaa ttattcatag    1320
ttctctcttc tccggcaaga aaa                                             1343

<210> SEQ ID NO 10
<211> LENGTH: 1296
<212> TYPE: DNA
<213> ORGANISM: Arabidopsis sp.

<400> SEQUENCE: 10
tcggaatctg ctggtaatct acgcaaagta tacttgtaat cagcgacagt gagagtgatc      60
tacaagtaga gaataagaga ttcaatgaat gaattgaat gaggaaatgg tgaaatcaat      120
agagagataa ggaagatacg aacggagtag atagcgcgag aagaacggac gacgccttct     180
acagccgtcg ctattttatt ggaaggtgag tctcggaaga tggacacggc ggtggcgctg     240
ccagtgacgg cggttagagc taggccggcg gtgactgtga aagcaaagat cggagacttg     300
gatctcccga gaattttgaa tttgcggaga atctccattt ttgtggattc tttgggtttc     360
gtattatttt tttcgtagta acgaagaaga ggacggagaa gctacacatt ttctaactta     420
cttgcaagtc gggtcggatc ggattgatgg acaatctaat gggccaggat ccggttagac     480
taatcgatgt gattttaatg ggctaagtaa gctgggcttg gcaaatagcc aaatataaaa     540
ggttaattta gtcaagaaaa tctctcaatt taaaattaac tgacgtaaat ccccttcag     600 tatcaatact gtaaaaattg gatagacaca gtaaaacgca gtgttttaca gaatctcttt    660
taatcgattt gacatcacac aaacttcaga gaatctcatt ttgataaatt aaagtttttt    720
ttccactttg tgaattttaa agcctaggta aattagtgca tatatgtaat ttaagtgtac    780
atactgtatc tctctgcaac gaatacaacc ttcttttta cccactacca cctgttttcg     840
ctaggcttgc tggactcaaa taatgtattt ttatacggca aaattattca ttaaatttca    900
actttacgtt atatacaaca ttttttacaa aaaattacta acatatatgg aacctcaaac    960
ctcttaatgt agaaatatta ataaattttt atttaaccat tggactaagg agcttccaca    1020
atctactcta atctaataaa gtgtatatct catgggtatc aatttttttt ttcaataggt    1080
```

-continued

| | |
|---|---|
| aagaaatcaa atcgttctac atatctttac gatcttgtga tattttacga gcgaatatcg | 1140 |
| tcgacataat ataaaactca caaaaaataa aataataatg atactccata taaggaaaaa | 1200 |
| agacagcaaa tatgtagggt caatataaac gcagcctcgt cgtctcttca tatattcgtc | 1260 |
| tctttgtgtt cttcttcctc ctcagattct ctttca | 1296 |

<210> SEQ ID NO 11
<211> LENGTH: 1359
<212> TYPE: DNA
<213> ORGANISM: Arabidopsis sp.

<400> SEQUENCE: 11

| | |
|---|---|
| ggatcgaaca ctctctcgta cgtcaaggaa agcactgtga tgccagtgag gatgacctgg | 60 |
| ctcgcgacgg aaaggttgct gagccgagtc ggtacgagaa acgagtccgc atagaaacaa | 120 |
| gagaaacgcg acgaatagga gagaagaaaa cgaactcgat cgcgaatccg atctcaactc | 180 |
| catgactgaa aaaaacaac cggagatttc gctcacctcc cgattttgga ctggactggc | 240 |
| gagagtcgct acaagtcgct tacggcgagg gagcagaaat gggaaaatta aggctaatta | 300 |
| ctaatttacc ctcaagtttt attattaagg tgacctgacc tgctctgtct atatgtgata | 360 |
| ttgtgacctg ctttgcctat atggctatat gtgatacctg taatcacaag gatatttcag | 420 |
| gtggagaatc agagaaagaa attgaagctg aataagacac tatatgggag agattgaaag | 480 |
| gaagctgttg ggccattttg gtgtagcggg tcgcaagtcg agcgtgagac ttattgctgt | 540 |
| gccattgcag gaatgcaaac agaggaaaga tttcacaaat gggaaacgga tacatgctca | 600 |
| gatggttgtt ttgttgtagg aaatgccttt caatgagtat gttaaacgct agctgtcctg | 660 |
| tttaatggac cggtgtatgt catcttgtct tgcactgtgt gagcacaaca acttgcaatg | 720 |
| tttccattga tgctgtagca gtctctcaca ttaagctctg gtttggatgg ctatgaacaa | 780 |
| gttgattggt agataagtta aaatgttgtg atttgaatct ggaatgaata gaaagatgtg | 840 |
| attggtactg atgtaaattc aatgctttag agaatgtata caggcaataa tataccaatc | 900 |
| attatgttta ttgctgacta agagccactc ctctttgctg ttgcaattcg gcaatcgttc | 960 |
| tagatatggt ttccatttca aatcatgata tgcattgact ttttccatgt ggcgttcgga | 1020 |
| aatctttcat ctatactacg tctacgttgc aagttttgca aaatgtttaa attagtagaa | 1080 |
| tctcacgtat ataaaaactt tagtcgccaa attgaaaatg gagaatgaat ggtaaactac | 1140 |
| tagtttaccc tcatatttta gctgaaaaat atcgtcacag ctgacgaaga aattagaaac | 1200 |
| aacaagcaac gtgtcacttc tcatgtcgtc gttttcccca agaaatatcc aaactaacac | 1260 |
| ccaattacct aatgccacgt gtttactcac actcctttaa acaagctcgt aactgtttca | 1320 |
| tcttcttgtc cccaaagtct cctcttcctt atctcttgg | 1359 |

<210> SEQ ID NO 12
<211> LENGTH: 1385
<212> TYPE: DNA
<213> ORGANISM: Arabidopsis sp.

<400> SEQUENCE: 12

| | |
|---|---|
| aagattttcc gctacgggaa tttgaacctg aaaatgctga ttttttaaaga aaatttagct | 60 |
| aatgtgctac atgagatgtt ttttttgcta agtatgagt ttaaattgga tatatacatc | 120 |
| attcaattta ttttttctaat ctagaatttg ctttcctagg acaaatatag gtactgaatt | 180 |
| attaaagaac atattttttg gtaagatata agtgagtttt tatataattt tgatgatttt | 240 |
| aggtaagttg atgtgattta ctgtaaagtc ttttcaaatt ctatctaaaa ctatgagatt | 300 |

| | |
|---|---:|
| tagatttctg tatttttaac taaagaagtc ttttcaaatc ctttcaaatc cttcaaaatt | 360 |
| aataagaatc aaatccacta actattttca gtaacagtaa aaaggttgat ttttaaattt | 420 |
| ttaatttaat aacactcaat ttcatttaaa aatttaaaat ccataattaa ataacataaa | 480 |
| atttataaat tttacataaa ttattagatt gaatacaccg ctctaaatat acacaatgta | 540 |
| aaaagtctgt ttaagatcaa ttatagattt aacttaaatc taaaggccca taataccgtc | 600 |
| ctgtacatca tatagttatc tcaagttgta atactgtaat acccgttggg cccagtggcc | 660 |
| catttatcag atttcaaata acagatctca acactagcat ggctacacac gtgtcagatt | 720 |
| caatgcatca gtcatatctt cagcatccaa cacttgtcaa ccttccattg gatctcttaa | 780 |
| ctctacgcct cgaaaacagt ttttatttat ttatcattcc atttctcatt gtatcttcat | 840 |
| cagtctcttc ttattccatt ttttcaaacc acttgcaaaa ttcgaatcag atcttctctt | 900 |
| caatcgaaaa aaaagaaagg taatctctc tctctctaat catcgttcgt ttcgtagttt | 960 |
| cttcttctac gtgtagatct gatctttgat tgtatgtttc tggagatctc gatctcatcg | 1020 |
| attctctgtt cttatcactg attcagtgtg tttgatatct aaatccgatt tgtgtgtagg | 1080 |
| atgttaaaat ttaggtttcg gttttgtttc tgcttttgaa cgattttgct ctagattcgt | 1140 |
| tatccgtgaa gaacatagac gagtatgtag atcttacttc ggattcgcgt tgaagaattt | 1200 |
| tctctagatt cgtcacctat gaagaagatt cattgtgttc ttaatctaga tgattaggtt | 1260 |
| attgtttcga ctcatttgtt tatgcctatt ttctctatgt tcttaatcgg tgaagaaatg | 1320 |
| tatcaatgtg tgtatgtttt gggttctgat tttgtaggat ttgctctaga ttgttgaatc | 1380 |
| gaaga | 1385 |

<210> SEQ ID NO 13
<211> LENGTH: 1356
<212> TYPE: DNA
<213> ORGANISM: Arabidopsis sp.

<400> SEQUENCE: 13

| | |
|---|---:|
| cgcaacgata ggtgcctatg gaaactgaat caacagattt ggttttgata tcatatatca | 60 |
| tcagctgtct actatttgat ctaggacaac acaaaagctt attcttctcc aaaatggcta | 120 |
| ctggtaatga ttgcgtaaca ctacgattca ctatcgaata tatttgttcc caggtcttgt | 180 |
| tctctgaatt gaacgaccat attatcattt gttggagagg tttactaacc gataagcaca | 240 |
| aacggttatt caggctgcgt gtgataatgt ttctatgatc tgcttccgca aaaggagctt | 300 |
| tagagataac ttgaaaagtt tcggtgtgga gatctaacgc taaaacttta atttctttct | 360 |
| tcccggttaa ccaataaagc gatccatcta catacagagc atgccccga gacgaggaag | 420 |
| tattaatccg ataaggagaa gaaggattga tatacctcca agtgttggtg ctaaaatcaa | 480 |
| aaacttcaca tgtagtagcg ttttctaggc caagttcgga agagttatac ataaccaaac | 540 |
| cggtttgtat atgccactga ttttgtcttt gccaaatcca aatttaacgt gactaaaata | 600 |
| acttggctgc tcaagacaga tttgttgcaa cctggaaaca gggaaacgtc gatgccatcg | 660 |
| agtggcggga ttataaacaa tgttgtttaa ggtttggtaa tcaagaggc aaacaagacc | 720 |
| gtcacaacta ttgtggaaaa gttggtaaat atgatatcgt tctgatgata tcaacaacac | 780 |
| gttagtttta agtggaggag aatcagcagt aacatgatgg gcaacacca acgtactggg | 840 |
| tacttcagac accaatacaa gatttagatc tttcccgcca gctgagcaga tcaactgttt | 900 |
| cgcctgaaa tattgagatt cgattgtcaa cttccattgt tgcaagcag acttgaatct | 960 |
| gagcagagat ttcaccggaa ctctctcaag aatatcctca acggtgtcgt ggggaagcaa | 1020 |

-continued

| | |
|---|---|
| ttgcattatt tctctgtcta ttgagaggat tttgttctga gtgatggata acatgaaaga | 1080 |
| tatgcttatt tgtatcaatt caatccaatg ttgatttttt ccttgaggag gaagataaaa | 1140 |
| aaaaaaaaac gtatatacaa tcgatgggcc ctaaccctat ccctaacaaa tctctttaat | 1200 |
| atgtaatgcg ctttaatagt taaagcccat tagttaaaaa cccagagcta tattgttgac | 1260 |
| ctagcaaatt tcggatctat aaattgaagc cattttctag gtcattagtt ttttcgtcga | 1320 |
| gcagccgcgc ttttggccg aggaaggata aagaga | 1356 |

<210> SEQ ID NO 14
<211> LENGTH: 1343
<212> TYPE: DNA
<213> ORGANISM: Arabidopsis sp.

<400> SEQUENCE: 14

| | |
|---|---|
| atgtgtgtag cgaaaaccaa tgacaacgtt aattgactca tacactgcac aatgttgaaa | 60 |
| gtgtttcaaa gtgagatata gagagtcaca agaagagtac gaaaagaatc aaagtaaaac | 120 |
| tccgaaaaaa gtcttttgaa tgcaagagat gtgaaaaatc tagagatgtg gttgtgaact | 180 |
| ttgattcccc tattgtgcgt tggtttcagg atggacatgg tatacccaac accctcaag | 240 |
| gtttgaagag ggttttgatc gtcagaacaa gctgcgagaa agccgatgtt aatatgaaa | 300 |
| cattagctcc taaacgaaag agactaaata ctgtgaagaa agtcactaag tttattgaag | 360 |
| acaatgaaca attcaaagac atgaagattg aagaggtttc ttttaccgca cccaaacagc | 420 |
| tgaaagggaa aaagttctaa ataatgatgt tatagttgtt gatattaaaa cttgaaaaat | 480 |
| caacaagtta aggaaactaa agagacagaa taaaccttaa cttgttgatc ttttcaagtt | 540 |
| ttgttatcgg taactacaac atccttactt atatttttt cttttcagcc gtttgggtgc | 600 |
| gacaagagaa acctcttcaa tcttcatgtc tttaaattgt ttattgtctt caataaactt | 660 |
| agcaacttcc ttcacagtct ttagtctctt tcgtttagga gatactgttt cataataaac | 720 |
| atcggctttc tcgtagcttg ttctgacgat taaaaccttt tataaacttt gaagggtttt | 780 |
| gggtattacc atgcccatcc cgaaaccaac gcacagtatg gaatcaaagt tcaaacacat | 840 |
| ctccaggttc ttcacatctc ttgcattcaa aagacttttt cggtgtttta cttcgaatct | 900 |
| ctttgcattg gatcttaata atgtttgagc cgaccatgtt ctacatatga tgaacaaaac | 960 |
| tcaagcacta gcgattatta aggcttttt tttatttcta tcgatctttt tttttacct | 1020 |
| attgataatg ttgatgttga aatactcaaa catggaagtg gaattcaaaa atacaactaa | 1080 |
| agatctgttt tcttagtaca tacagaattg agaaacagag atgaaaaa tgccaagagt | 1140 |
| gtgaacaaaa gtccacaaaa caaaagcctc tgacggagaa ggaggctttt aggtgttacc | 1200 |
| caaacaaaac gcacacaata cggcgtcgtt tagaatcaga aaagacattt ctttatggtc | 1260 |
| acttgattct ctcttccttc atcaatcaat ctcgtctcct ggaaaacatt agggagcctc | 1320 |
| tcagatcctc aagaaaaccc taa | 1343 |

<210> SEQ ID NO 15
<211> LENGTH: 1319
<212> TYPE: DNA
<213> ORGANISM: Arabidopsis sp.

<400> SEQUENCE: 15

| | |
|---|---|
| tttgtcacca aaatcagaca ggcaaagctg gctcaagcat cgcttaaatc cctgtaaaac | 60 |
| gcaactatgt aattaatatt gagatatact tgttgctttc tgactctgat ttcattcact | 120 |
| cggcagcatt ctcgtgctct cggctgctgt tgccaaatct tatggtatct ttctcaaaaa | 180 |

```
gctcatagta ccgttgtgtc tccaacagac tttcattgat gtaagtctta taggtactac      240
taagatccat aatatgtaag gcctcacttg cttctttccc atcataccat atggctcttt      300 ctcttttttcc acctcccggt actgaataac agcatgttgc ttgctacaaa atgtgtgatt     360
agtaggaatg tcggatcttt ctctcacgtc caaagaggta gcaaatttgg taatgaatgc      420
aaagtgtctc tttcagtggt tcaccatcct taaaatgata aagtctccat ctttcttttgg    480 gttttctatt atctacggga ttattgaaga ggagtgtgat acctttgtat atgttggttt     540
cttcagcaag tttcctcgat agctcaaaac atcgcacacc atgttttttca atcatcaaac    600 atgaatgaag tagcagctat cgagattctc tctctcgtcc ggtacttagc caacacccctt   660 cctccgaatc tctgaatgtc agattgatgt ctcctggcac ttggaggata atctaagcag    720
acatggatgg gtcctaatcg atcaagatag tatcttccat ataggtctca agagtttgag    780
aagatgtctt tcaccgtttc atgcggaagt tgactcctta ctttaagcaa ttgaatgcat    840
gatcgtaatt agtgatatat ttggagtttt cgcttccggt tactctgata tgatatcttt   900
cctcgacaac tataacgaat gaccaatatt tgtaatagag atagtctatt ttcgatctct   960
catttgtttc tttctttttt taacattaca ttttttcata gaattctaat actcacagat   1020
tgtttaatga ttttttctta caaaaagtat cattcagata atttaataaa aatggtatcg   1080
cagtgccttt atttaccttt aggagtaagt tttctttctt ccgatatcct aaattgttcg   1140
acacgtgtca atcacgaaac cacaaccaaa aaaccttgtc gtcttctcca atcataaaaa   1200
aaaaaaaaaa acagtgtccc aatttgatca aacaaaacaa attcataaat tcggagaaga   1260
gaacgaaaaa tcttcttgtt ggcaaatctc cggcgagatc atctttctta ttttgttcc    1319

<210> SEQ ID NO 16
<211> LENGTH: 1140
<212> TYPE: DNA
<213> ORGANISM: Arabidopsis sp.

<400> SEQUENCE: 16
gcgagtaaga cttatttgaa acatcgtcaa atttacttct tttggtgtat atttctcatt       60
atatggcgta tatctgtt tatgtaagaa attgttttcca aaaattactg tatactgact      120
ttgtaatctt gttttgatat caatgaattt ataaggaaaa aaataaaata aaaatataaa     180
gtatgatgta catgtaaaaa aagttgtttc aagcgtaatt gttttttggc tagagaatga      240
atatacagca acagtaaact aataaacttg cgatgaacta aaatttctgg tattcctaca      300
atcaatgaat cactaatttta tctataagtt ttagctatat ccgcttaaac cccgcctcaa    360
cttgctctct ggtctgggta tagttgggct acaacagtga aaccgtaatt aggaaagaaa     420
tgataaaaac ccaatccaga agcttactgc aagataaaga gaaagatcat gaagaggtag    480
gagtgattca tataacaaac agggtcacgt tgtcactttc tcccagaaaa atacaaattt    540
agactaacta tataaggaga cgacttcaga gtcttctaat gggttagtat aactcgggtc    600
atcttttaat ctctggcttt aaagacatgg taagattcca tatatatgaa aactctgtgt    660
gtggtggatt gctttttttca tttaaggcaa agataggttt taaggcagaa gacaagaacg   720
acctttggct tatttataqg agaccaccac tttcacttga gtcgagacag taacgacatt    780
tagaatttgc attactcatc ttgtcacttt ctcccaggaa aaaaaaatac aaatttagac   840
caactatatt aggagacgac ttcaaagtct tctaatgagt tagtaactgg ggtcatcttt   900
taatcgccgg ctttcaagac atgtacaatt tcatatgaaa actctgtgtg tggtggattg    960
catccaagac agttttaaga cagaagataa gaacggcctt tgcttatttta taggagacca    1020
```

```
ccactcctct cgataaccat gactcgagac attaacgact tttaaaacta agggacgaac     1080
cttaagcaaa agctcttgca ttactcaaat tcttctgcca cttggtaagt cttttctct     1140
```

<210> SEQ ID NO 17
<211> LENGTH: 1331
<212> TYPE: DNA
<213> ORGANISM: Arabidopsis sp.

<400> SEQUENCE: 17

```
ccaatacatt cgaacacgtg attgttcgtt aattttcttg attctgtaag agaaacaaaa       60
aatatagatg tccaactttt tttttcgggt gggaatatag acgtccagct tagctacgta      120
ctgaataatt caaagttcca aactagtata tattaataca attgacgata aggtcataag      180
gatcgatgga ttccaacgat tcgatacaag tattaatgaa ataagataac acgattgtga      240
cagcaaactc tatattgata tttctatttt ttaattagcc atgcgttgca cgatcaattt      300 acaaataat aaaagaaaat gatcgatcaa agagcattcc attgaaattt aattccatcc       360
tgtaatcaca taattttggg cccaatccta ttttttcaaat gtaacatgct attacatagt     420
cacatagaac atcctaaaat aggggttaaaa tgtacttttta tctatttgca atttgatat    480 tttcctttct gaaaagatt agtatatggc aaattatctt ttagataaaa gatcttttgt      540
tctgactata cattaattta ttttaaaaaa aaacttaac agatatattt gcaaatacaa      600
aatgatgaaa ataaaaggg ataccataat ctaaaatctg acaagaaaa tatacaaaaa       660 gtcaattacg atacttagaa aaagaactat atattttgg gtagggaagt tcaaaaacaa      720
attaccgatt tgctgactat atgagcaatt attacatact tttatttatt tgtacaacaa      780
ttattacaca tacttgtgtg gaccaacatg attaattta tattggccat atggtgcgta     840
gtaaatgtta taataacttg aaattaaata ataactaagc tcgactcgat atatagatcc      900
aaccagtagc ctctcttatt cacacctaat cttcatcttc atcttcgcat tcatagtctc      960
tacgatcagg taatccccct ctctctatct atctttcata tatgtgtgta tgtgtaaact    1020
atctatattc tgaaaataga tcaatcaatt gatcttttcc tatctcaatt gttttcacaa    1080
ccatcagttt gacttttgat cgtttaaggc tcgagagaat tatcattcac tgtagtaaag    1140
atagtttata ccaacaaacc catttggtgt tgaccagctt tcaacataag tatgagttag    1200
agctagaacc ggattagtat taatgttact tgtacctgtt catagtacta accaaaaatg    1260
atccaaaaaa atgaaaataa caaataaacc atttatggtt atcacagata gataaaagaa    1320
gtcaacaacg a                                                         1331
```

<210> SEQ ID NO 18
<211> LENGTH: 1272
<212> TYPE: DNA
<213> ORGANISM: Arabidopsis sp.

<400> SEQUENCE: 18

```
cattttgaat gacattggtt tccagattta acttcatatg tcttgccaag taaaatttgt       60
acgcattgat atagtatcat ggtcctgact ttaagcattg gcgatgggta atgatattaa      120
tgaaatatcg gcgaaatttc ttggataaaa agaaagatt cgtacgcatg aaaccaatat       180
gtgatgttgg ttccatattc acatagcatt tgtaaaattt agaataaaat cgagtttacg      240
tcagagccat ccaaccatta ccattaaaaa ttggatgaac tgatgaacag gttgaaccag      300
aaattgtcac tcaaagttag agcttggttg ataggttctt aagactaaac agttcctcat      360
cagtatgtaa tataatgaaa taatttaatc tctttgtgtg taaggtgtta actggactac      420
```

```
cactagactg aatttttaat taagtcttat cctatagtct tttcaataag ttcacaattg      480
caagtactta ataaacaaaa taattaatca gttaattatg acaaattagt caacatccga      540
tcacattcca cgttgtaaag ttaaatttta aggtagatac taatcatact tgtaaaatga      600
ataagatgag ttcttcttct tgtcacctct cgatcttgtt ttaagtagtt ggtgagatgt      660
gataaacttg taacatgcca ctgagttgtc aaagacaagc atctatacag ttattaaaaa      720
aaaaggttaa gcatgtaaaa atacacacac atgtcgtagt aaatatacac cttttatataa     780
ttaattatat tgtaacgaat tgttgttttt gttataatat atagattaat gcatgatgtt      840
ttgcgattaa agccagacga gttgtaatat ccacagcctt gataagctct acatgcagtg      900
aacaattttta tacatttaga aaaaataatc actatctcga ccatatagac caggccacta     960
cattacagct aatctctgga tttacttgat aattaagaca atatagaac attaaaatac      1020
taactcgatg cctcacctta gcctcctctc aaattgtcaa tatctagatg gagtgttaca     1080
tccacattcc taacagtttt tactctttat tttaatatat ccttcaacag atcatcatca     1140
gaataatcat caaatcatta ttatatattt aactagccca aattgtacca tacctatcaa     1200
tttaaatttc tctttctatc tactataaaa agtgactctc taagaactcc aaagattaga     1260
acattgaatt ga                                                         1272

<210> SEQ ID NO 19
<211> LENGTH: 1371
<212> TYPE: DNA
<213> ORGANISM: Arabidopsis sp.

<400> SEQUENCE: 19 ctctttatttt gtcgtgactc gcgaaccct tttttattaa cgttttagtc aacacaacat       60
ttcattaatg ataattctac tactattagt ttgcaatgtt aactaaactc tttttacgtg      120
agaaaactta agattatcat ttccagacca ccgcaagttc cttgaaaaga ttgttatata      180
tataacagct gcatatctta atacggattt atgggcttta atttgaaatc aattgtatca     240
aataggtttg aaaaaaaatc gtatcacata cctttatttt ttgagtgtag tataagcaag     300
caatattgat gaatgcgtga gtctgcaaaa tttaaccccca aaaaaaagta agcaacaata     360
tatattcagc aatcatgtta gaaagtattt taatcatgtt gaactgaacg atctccgcgc     420
taattagtat tcctaagaga caccaatcag aaactattgg atagttcgac ggtttagaat     480
ttgtccagtt gagaatggtt ttcaaactat tttataaaat ttttttagcg aatttctaaa     540
gttaagttga ccggcacatc ttgtggttaa atgtttcact cgtcgttgaa aaagtctttt     600
caacaaaatc ttactttctg gatataatta atatcatatg tacaaaaatt gattaatggg     660
tcttaaacta tttcatgtat ttactattta gatagagacg tttaaaaaaa aactattttc     720
gtgtctttac tatttagata gagattacac gacatggaaa taatagtaca tggtcaagtt     780
tatatacgga cgactctcat gaaatcctac aacaagaaaa caaagcaaca tatagtataa     840
tgtgaaatat acactgttaa gcaacatatt acgtattata gttatttttaa tgttaatgac    900
gtacaatgta caaattctag tattcttcac ctgaattatt tgatgctaaa ctacgtacgt     960
cgtggttatt ttcattgttc tttaattagc catctcgaaa tataattatt tcaatgttac    1020
aagatttttag tcgctctaat aggatgttta tgaatttaaa ccgacccaat ccgacttgtt    1080
ttttcttcta aaaatattta tcttgaaaat gatttttatta aattcgtttt cgtcttagtc   1140
taattcagct ataagtata aacgttatga ccaagtccat aatcaaatca tcatagtatt    1200
tctccttaat cacaactaca agaaaaggaa atgggtcatg actttcttat aaaacattaa   1260
```

```
ctaagatttg accaaacata attttgtatt atcaatatta caccataaat acggccacat    1320
atcctcctag tttcttcaca caactctccc ctcaaaacat tccatcaaag g            1371
```

<210> SEQ ID NO 20
<211> LENGTH: 1400
<212> TYPE: DNA
<213> ORGANISM: Arabidopsis sp.

<400> SEQUENCE: 20

```
acttccacca gaaaggcgaa aaccaagagc tttgaattga atagtcaaaa ataattgctt     60
ctactcttca ttcttcaacg tatgcaacgt aacttgtatg attgtgcatt tatcattttt    120
tatcggcaaa ttttagcctt acacaaaaga cataataaag tatcatggcc ttttttgttg    180
acattgtcct tctcttgtca acaatcttcc tggttttaag atacatatgg atggttcaga    240
atgtcatata gtataatcta ttactctaca ctttgattga tgacattctt attccgattt    300
ttatccaagt cttttattag atgaaaatca actgttattt tataaaaaaa ataaatagtg    360
gatttaaagt gatttgagtg acatacatta ggtgaaattt gaaggaattt cttagttaaa    420
aaatcaaaga tgcaaatctt atagttttag gtgagatttt agagaatgtt aatagcaatt    480
tcctaaagtt cactaaaacc atctcaaaac tcatcaaaac taaaatcact ctcaattcat    540
ccttcaatac agcccctaaa actgagaatc attttttgtc aactaaaact gaaattcata    600
catttgatgg aatttgagta gccgccgggt aatggaccca accaaaggct cacatagtca    660
catggtacca agatttatag tgatatatg cgacatctct ctaccacata gtcacatggc    720
accaagattt atagtgacaa tatgcgactt ctctacttag ggccggcttt cagaaactct    780
agaagaacta gccactgatc gactatatta gagtagttaa ttttatcaat tacatttgaa    840
atgtttatct ctagtaagat aaatatcaaa caaacaaaac ttaatccaag gacttgtctt    900
catatcgtct attaagagtc gaatttaaga aatgaaaaat aaacgattca agcttaagtt    960
agttttagga aaaagacata ctgtttgctc catatagttt gtacatgtat taaatataga   1020
ataacaaaat attttaatgt ttgctccatt gacattacat gtattaaaca gtttaataga   1080
aaaacgaaca tttttgtttg ttcaatcatt gggaaatcat agaattgttc aaaatatgaa   1140
acaaaagtga gaaatatcaa ttaatataat agttctgttt aacaagaaaa ttgaatttag   1200
accaagtcca caatattcat cttgagtaag aacacgacca aaagtcaaac tcgtttcgaa   1260
atacataaat atgtacoccg ctatacaaaa agaaaaaga catttacatc cacttatccc   1320
aatagacaaa tgaccaaact acccaacatc taccectata tatacctcac cacctttgcc   1380
ctctcaacca caaacaataa                                               1400
```

<210> SEQ ID NO 21
<211> LENGTH: 1307
<212> TYPE: DNA
<213> ORGANISM: Arabidopsis sp.

<400> SEQUENCE: 21

```
cggatggttg aggtagtatg agtgaccgtg acgatcaaac gttctccaaa gaaatcgatg     60
tagcggtttt cgtggatatg gcgcttttgg attcttcttc tgatcctagc catttaatct    120
gcataaaagt gagtatgaga gagaagatta aatagatatc aatcctaact aatattcaag    180
aaaacataat atagatcaat aaattgatga gagtaaaaac acaagatgt ttagaaataa    240 ttattgtcaa gactcaagtt tcttcaaaat atcaagaggc gcttggaata agacccttat    300
tctacaatac atcaatctat atagagataa agactaagca taattttaa aatagaaaaa    360
```

```
atataaacgt aaataacact tttttgaggt aatactaaat tttctaaaca tgaaatgtta      420
caaatccaca atatttccat ataaatttgt aaataatatt ttgttagata atgttaaatt      480
ttctaaactg aaatattaac aaatccgtag tatttccatt attaaatctc gattttgttt      540
caatgggaga tttgaatttt gaaccaaaaa aaaaaaaaaa gatttcatca agatatctag      600
ggggatattt tgctggaata tagctttgat gagaatattt atattttgta tctctgaaaa      660
tcaagtttaa aggggaaatg attatgggtt gaaattttgc aatcaaaagc cctaatttgc      720
aaaaactaca taagttttttt gtttgggctg gcgctatcgg atccttttag cttacatttt     780
aacatctggt ccacttagaa agagtcacgt agtatatggt aattgtcaac ttgatttttc      840
aagttaaaag aaatatgtat caaaatgact aaaaagtagt gaaatattat gtatctaatt      900
tgtttattta ccaaattaat gctataaaaa tgttcaactg tacaattggc atggaataat      960
atgaacataa atcatacatt attaagcact tttgcctacg aagggatacc aacttcatta     1020
gtttacattt tcttttgtgt tcaattgtta gctcaaaccc aattaagtgg ggaaagtaag     1080
aagcaacaac tcctcttccc ggaccectaa caaatcaact aaactcaata tcaaaccatt     1140
ttaaaagagc tcatcattaa ctagctacta attattctta atcaatcact gcttaataca     1200
aagcactata tatacacttg tatcttccat tagtttccca ccacaactac aaaacattcc     1260
aatacacaac acacaaagca cacactttttt ctttctttta aacccca                  1307

<210> SEQ ID NO 22
<211> LENGTH: 1324
<212> TYPE: DNA
<213> ORGANISM: Arabidopsis sp.

<400> SEQUENCE: 22
ttccctccaa tgtcctactg tctccttctc tgtgtgttac catggtttta cttcaccatg       60
taagtctctc tcattatcaa aattcatctt ctctgttttc ttcctcctct gaatcaatcc      120
tttgtttatt tcttgtgttg tgtgtgatgc agttagagca agggatgcgt ccgatttcac      180
gatgttacaa tccaaccgcg tattcgacaa caatgggaag aagtttcttc gcaggtgcag      240
ccacaagcag caagctattc tccagaggtt tctcagtcac aaagccaaaa tctaaaaccg      300
aatctaaaga agttgctgca aagaaacata gtgacgcaga gagaaggaga cggcttcgga      360
ttaattccca gtttgcaact ctccgcacca ttcttccaaa cttagtcaaa gtaagtttag      420
ctctgcattc aattacacaa aatgtttcac cagagaagta acacttttttg tattatgttc     480 aatgaaacta aacagcaaga taaagcatct gtgcttggag agactgtcag gtacttcaat      540
gaattgaaaa agatggttca agacatacca accacaccat ctttagaaga caacttgaga      600
ttggaccact gtaataacaa cagagacttg gcaagagtcg tgttcagttg tagcgacaga      660
gaagggctaa tgtcggaggt tgcagagtca atgaaagcag tgaaagcaaa ggcggtgaga      720
gctgagatca tgacagtagg tggaagaacc aagtgtgcct tgtttgttca aggtgtcaat      780
gggaatgaag gattggtgaa gctcaagaaa tcgttgaaac ttgtagtgaa tggtaaatca      840
tcatcagagg cgaaaaacaa caacaatgga ggatcgttgt taattcagca gcaatgagta      900
ttttgtttat atacttgtac atctctgttt ctcctagtcc attagagaag gtagatgtaa      960
aggtataaaa gcccatgtgt tattgaaatt gggtggatac ttacaagagt ctatatgaat     1020
aaaaatgatg caattctttc tttggagatg gtgtggatgt tataacaaaa tatgaatcat     1080
gtgaaatttt ttgtcccatc tttgttctta cccaattgta cctttttgaga tgaaatccca     1140 tggttgcttc tagtagatag ctttcttctg ggaaacaaag atttggttta ataagttgaa     1200
```

```
ccaacgaata actcttcaaa cattccccac ctacttctca tcaaacctcc ttataaatag      1260
aggattccag cacaagtctc ttcatcactc aaaccaacaa gaagtagtca aagcacaata      1320
cagc                                                                  1324

<210> SEQ ID NO 23
<211> LENGTH: 1276
<212> TYPE: DNA
<213> ORGANISM: Arabidopsis sp.

<400> SEQUENCE: 23
ttgcttgttt tctgaatctg tgcgtgtctt ttttgaaatc gacagcgcac tccaatcagg        60
ttgcccatgc tccttccagt caggttgcgc agatcaattg tgggcattgt cggacgaccc       120
tcatgtatcc ttacggtgca tcatccgtca aatgcgctgt tgtcaattc gtaactaacg        180 ttaatgtgat tattcctatc tattaagcca cctctgcatg gttgagttaa gtatagagat       240
ctttctgttg gaaattttca tttctgattc attttgcatc cttagatgag caatggaagg       300
gtacctctcc caactaaccg gccaaatgga acagcttgtc cccctctac atcaactgtg        360 agttatcaaa ttatgaattt gtaatagttc tgtatattct tatggaactg gtacttactc       420
tgttcatcga tttttcattt taccaacagt caacaccacc ctctcagacc caaaccgttg       480
ttgtagaaaa ccccatgtcc gttgatgaaa gcggaaagtt ggtgagtatt tctatcacct       540
gtgttcttct tcttatttac cacattagag gaagatatga caaagtgact gaaacacaca       600
aattgcaggt gagcaatgtt gttgttggag tgacaactga caaaagtaa tcaagaatga        660 gtgagatctt gaagatcaaa tccaaattct tcctctattc ctgcgtttgg tttgtgcata       720
ttacatacgc ggaaaaactg tatgttatat atctcttgac tccttttaa cccaagagaa        780 aaagcttatc agaatctctt gttactgcat tattggggtt tattcaaagt tgaagacaca       840 aggttttgc tcgaataatt tggcattctt ttgctccatg gaacttgacc ttctcttctg        900
tttgttgact tctaaaactc catcggccct tgtggcattg ttaatgtatg tatgaatata       960
atctgataca ccaaccaatc attaagattt gggtttgaaa tctgtctctt ccgtggatga      1020
gatatgctac atgtcacaag aactggtctt agctttggta gataagactt gtcttagagc      1080
aagtcttgaa atctggaaat ctattttgca gtaatcttgt cacaacaacc ataacctaat      1140
cagtcagtac cctccaagaa cattaaagtt agatgatccg acaaaacctc tcaacaagac      1200
caaactcttt ccatataaat actctttaac actgacacaa agtttcatca ctttctcttg      1260
atcactcact gcatca                                                     1276

<210> SEQ ID NO 24
<211> LENGTH: 1290
<212> TYPE: DNA
<213> ORGANISM: Arabidopsis sp.

<400> SEQUENCE: 24
tctcccaaat aaaatgaga gcaaacacta atctaatatt aaattgaatt aaaaactttt        60
aaatagtgga aatatatacc ctaaattgga aataaaaaac ccaaatataa tattacaaac       120
taattttaaa ataaaaaatc tcttttaaat ggtgaaaata tataccctaa attggaaata       180
ggaaacccaa atataatacc ataaacttat attaaaatga atcaatatt cttttaaata        240 gttgaaatat ataccctata ttggaaatag aaaactcaaa tataatattt aaatttatt        300 ctaattatt ttggttgaat agattttata taaacttgtg gtattattat tgtccataaa       360
acttgtttta gtgttacttt taagaattttt tcaaataatc atttgagtgc taattatgtg    420
```

```
taaacaactt ttttaatgcta tttttgtcca aaaaacttaa aaatgtgcta tttgtgggaa      480
tttttcaata agatataaat ttaaaactga gttgattaat taaaagtgtc acacaaaaaa      540
aagtttaatg tgaacaacaa cattaattct tttttaaaaa attttgtttt atactattat      600
tctattaaca tgttaattaa tataactaga aaaaaaaatc aatctactaa aactaggttt      660
tttagcattt tataaatatt tgtatgagaa ctttctctaa ttcagttcat ccagttaacc      720
attgttcgct tattctgcaa ttcatttatt tatctgatat accagttaac cttaaatgtt      780
gtgtaatcag tcgtaaaatt gttttgtgta atgttacata aattaataga atcaaattta      840
aaatgtgttc taattatgct atgacgttat aaacaaacga taaattccga ttcatgatta      900
tgaagtattt caattgaaaa cacaaaaatc gacaaaattt taaaaatatt ttagatctta      960
cattacatac ctgtattgtc gcaaaggaaa atttatttct tgtcctaaaa ggccatttgg     1020
aacttgagct aatgtaaata tataaatggg cttattgggt cctctaatgg gcttgccttt     1080
gacgtagaag acagaagcat cgttgtgact cccgtttgtg atttaggaat ccgcactgct     1140
tgccgttttc cgtttctact ttacttttca attcagaaac gcctctctcg tcgtcttcaa     1200
agctaaatta gaaacctgac gatctctctc tctctctctc tctcgatcgg ataatatttg     1260
agctttgtgg ttggaggatc tgagttagtc                                      1290
```

<210> SEQ ID NO 25
<211> LENGTH: 1260
<212> TYPE: DNA
<213> ORGANISM: Arabidopsis sp.

<400> SEQUENCE: 25

```
ggttattgtt gtgttatgat tttggggttc gtaaacatcg cttatataga gatttgaaaa       60 ctatttttt cttttttttt ttgttaacta tagatctcac gttttttgtaa atacatggtc      120 catgtgtgag tattttagta atattcattg caattgtcca aatgaataga agttgttttc      180
gtaactattt ttttgtcaat cttgtcctta cacacatttt tcctaatatt gtttcgtatc      240
ggtagctttg ccattgttga tatatttttt tagtatatat gtaagtatac cctaaatgaa      300
gtttattaag aaacattgta tatagttgtt tcatgtcatt cagttgtttt gtgttttttt      360
ttcttcatga ttctaattta agtcttctat ttcaaatttg aatttcatat attacttcat      420
tcaaaatgtt gtgaagatat cttcctgtaa ataatacaga aaaatcgtat cggacagttt      480
ggcaattaag attatattta cagtcagaaa aaataaaagt ttatatctac agtcaatttt      540
caaataaaag aaaaaaagtc aagaattatt tgtttcttag tgtttcatgc atatgagtat      600
ctctatcact cttgcctatg gctgaaaagt cctgaagaat atatgccgcc acatctatga      660
cgtaagtaaa atagtgacgt agagaaacag tcaatagatc acccattgag atttatccaa      720
aaagaaaaaa aaaaaaaaaa aaaaaaaaaa agatcaccga ttgacattgt atacactttg      780
tttttttttt ccaaacacta atacgcagtt taaattgaaa aactctaggt gaccgatcta      840
cttttgtgtt cttctatctt cagtatacct aatttttgtac cgccttcgta tatcatttac      900
caattttgac tactgatatg cactggcttt aaaattttcc aatcctgata tgaatctgtg      960
attctaagca ataacatata ctccctccga atcagaaaaa ttgattttttt aaagtttttt     1020 tgtattaaaa agattgagtt tatgtatatt tttatcaatc aatattaaaa ggttatgaat     1080
ttcaagaatc aattaattga gaattttaaa atttgatgaa ttactattgg ttaatagtta     1140
cgagaaatag tttagcatga ataaatagta aatttataact aagcattatt attttttttaa   1200 tcggtataaa cattctataa aatcaaactt ttttatatgg agggagaatc attttataag     1260
```

<210> SEQ ID NO 26
<211> LENGTH: 1335
<212> TYPE: DNA
<213> ORGANISM: Arabidopsis sp.

<400> SEQUENCE: 26

```
ggtaccggat tggagccaa gtctcataaa cgccattgtg gaagaaagtc ttgagttggt      60
ggtaatgtaa cagagtagta agaacagaga agagagagag tgtgagatac atgaattgtc     120
gggcaacaaa aatcctgaac atcttatttt agcaaagaga aagagttccg agtctgtagc     180
agaagagtga ggagaaattt aagctcttgg acttgtgaat tgttccgcct cttgaatact     240
tcttcaatcc tcatatattc ttcttctatg ttacctgaaa accggcattt aatctcgcgg     300
gtttattccg gttcaacatt ttttttgttt tgagttatta tctgggctta ataacgcagg     360
cctgaaataa attcaaggcc caactgtttt ttttttttaag aagttgctgt taaaaaaaaa    420
aaaagggaat taacaacaac aacaaaaaaa gataaagaaa ataataacaa ttactttaat     480
tgtagactaa aaaacatag attttatcat gaaaaaaaga gaaagaaat aaaaacttgg       540
atcaaaaaaa aaacatacag atcttctaat tattaacttt tcttaaaaat taggtccttt     600
ttcccaacaa ttaggtttag agttttggaa ttaaaccaaa aagattgttc taaaaaatac     660
tcaaatttgg tagataagtt tccttatttt aattagtcaa tggtagatac tttttttttct    720
tttctttatt agagtagatt agaatctttt atgccaagta ttgataaatt aaatcaagaa     780
gataaactat cataatcaac atgaaattaa aagaaaaatc tcatatatag tattagtatt     840
ctctatatat attatgattg cttattctta atgggttggg ttaaccaaga catagtctta     900
atggaaagaa tcttttttga acttttttcct tattgattaa attcttctat agaaaagaaa    960
gaaattattt gaggaaaagt atatacaaaa agaaaaatag aaaaatgtca gtgaagcaga    1020
tgtaatggat gacctaatcc aaccaccacc ataggatgtt tctacttgag tcggtctttt    1080
aaaaacgcac ggtggaaaat atgacacgta tcatatgatt ccttccttta gtttcgtgat    1140
aataatcctc aactgatatc ttccttttt tgttttggct aaagatattt tattctcatt    1200
aatagaaaag acggttttgg cttttggtt tgcgatataa agaagacctt cgtgtggaag    1260
ataataattc atcctttcgt cttttctga ctcttcaatc tctcccaaag cctaaagcga    1320
tctctgcaaa tctct                                                   1335
```

<210> SEQ ID NO 27
<211> LENGTH: 39
<212> TYPE: DNA
<213> ORGANISM: Artificial Sequence
<220> FEATURE:
<223> OTHER INFORMATION: Synthetic T7-d(T)24 oligonucleotide primter

<400> SEQUENCE: 27

```
ggccagtgaa ttgtaatacg actcactata gggaggcgg                            39
```

<210> SEQ ID NO 28
<211> LENGTH: 11
<212> TYPE: DNA
<213> ORGANISM: Artificial Sequence
<220> FEATURE:
<223> OTHER INFORMATION: Putative promoter element

<400> SEQUENCE: 28

```
tggttcggac c                                                          11
```

```
<210> SEQ ID NO 29
<211> LENGTH: 26
<212> TYPE: DNA
<213> ORGANISM: Artificial Sequence
<220> FEATURE:
<223> OTHER INFORMATION: Synthetic PCR Primer

<400> SEQUENCE: 29
agacttcact gcaacatggt gcccac                                          26

<210> SEQ ID NO 30
<211> LENGTH: 24
<212> TYPE: DNA
<213> ORGANISM: Artificial Sequence
<220> FEATURE:
<223> OTHER INFORMATION: Synthetic PCR primer

<400> SEQUENCE: 30
gtgtggaaat gacacagatt gtga                                            24

<210> SEQ ID NO 31
<211> LENGTH: 19
<212> TYPE: DNA
<213> ORGANISM: Artificial Sequence
<220> FEATURE:
<223> OTHER INFORMATION: Synthetic PCR primer

<400> SEQUENCE: 31
agacgggtgc aatgaaacg                                                  19

<210> SEQ ID NO 32
<211> LENGTH: 28
<212> TYPE: DNA
<213> ORGANISM: Artificial Sequence
<220> FEATURE:
<223> OTHER INFORMATION: Synthetic PCR primer

<400> SEQUENCE: 32
cgcgaacaag aactgtgctc ctatcatg                                        28

<210> SEQ ID NO 33
<211> LENGTH: 18
<212> TYPE: DNA
<213> ORGANISM: Artificial Sequence
<220> FEATURE:
<223> OTHER INFORMATION: Synthetic PCR primer

<400> SEQUENCE: 33
gccgtgagct ccgttctc                                                   18

<210> SEQ ID NO 34
<211> LENGTH: 17
<212> TYPE: DNA
<213> ORGANISM: Artificial Sequence
<220> FEATURE:
<223> OTHER INFORMATION: Synthetic PCR primer

<400> SEQUENCE: 34
tcgtgccatg ccaatcg                                                    17
```